US009096855B2

(12) United States Patent
Gu et al.

(10) Patent No.: US 9,096,855 B2
(45) Date of Patent: Aug. 4, 2015

(54) TRANSLOCATION AND MUTANT ROS KINASE IN HUMAN NON-SMALL CELL LUNG CARCINOMA

(75) Inventors: Ting-Lei Gu, Woburn, MA (US); Ailan Guo, Lexington, MA (US)

(73) Assignee: CELL SIGNALING TECHNOLOGY, INC., Danvers, MA (US)

( * ) Notice: Subject to any disclaimer, the term of this patent is extended or adjusted under 35 U.S.C. 154(b) by 965 days.

(21) Appl. No.: 12/738,210

(22) PCT Filed: Oct. 20, 2008

(86) PCT No.: PCT/US2008/011968
§ 371 (c)(1),
(2), (4) Date: Apr. 15, 2010

(87) PCT Pub. No.: WO2009/051846
PCT Pub. Date: Apr. 23, 2009

(65) Prior Publication Data

US 2010/0221737 A1 Sep. 2, 2010

Related U.S. Application Data

(60) Provisional application No. 60/999,668, filed on Oct. 18, 2007.

(51) Int. Cl.

| | |
|---|---|
| ***C12Q 1/68*** | (2006.01) |
| ***C12N 15/11*** | (2006.01) |
| ***C12N 15/12*** | (2006.01) |
| ***C12N 15/113*** | (2010.01) |
| ***C07K 14/74*** | (2006.01) |
| ***C07K 14/82*** | (2006.01) |
| ***C07K 16/40*** | (2006.01) |
| ***C12N 9/99*** | (2006.01) |
| *A61K 39/00* | (2006.01) |

(52) U.S. Cl.
CPC ...... *C12N 15/1137* (2013.01); *C07K 14/70539* (2013.01); *C07K 14/82* (2013.01); *C07K 16/40* (2013.01); *C12N 9/99* (2013.01); *C12Q 1/6813* (2013.01); *C12Q 1/6883* (2013.01); *C12Q 1/6886* (2013.01); *A61K 2039/505* (2013.01); *C12Q 1/68* (2013.01)

(58) Field of Classification Search
None
See application file for complete search history.

(56) References Cited

U.S. PATENT DOCUMENTS

| | | | |
|---|---|---|---|
| 2007/0042381 | A1 | 2/2007 | Bentwich et al. |
| 2007/0136825 | A1 | 6/2007 | Frommer et al. |

FOREIGN PATENT DOCUMENTS

| | | | |
|---|---|---|---|
| JP | H09-503125 | | 3/1997 |
| JP | H10-75794 | A | 3/1998 |
| WO | 01/92523 | A2 | 12/2001 |
| WO | 2006116688 | A2 | 11/2006 |
| WO | 2007084631 | A2 | 7/2007 |

OTHER PUBLICATIONS

Charest, A. et al., "Fusion of FIG to the Receptor Tyrosine Kinase ROS in a Glioblastoma with an Interstitial del(6)(q21 Q21)" Genes Chromosomes and Cancer (May 2003) pp. 58-71, vol. 37, No. 1.*

Massarelli et al. Clinical Cancer Research May 15, 2007 vol. 13 No. 10 pp. 2890-2896.*

Charest, A. et al., "Fusion of FIG to the Receptor Tyrosine Kinase ROS in a Glioblastoma with an Interstitial del(6) (q21Q21)" Genes Chromosomes and Cancer (May 2003) pp. 58-71, vol. 37, No. 1.

Acquaviva, J. et al., "The Multifaceted Roles of the Receptor Tyrosine Kinase ROS in Development and Cancer" Biochimica et Biophysica Acta (Jan. 1, 2009) pp. 37-52, vol. 1795, No. 1.

Lue, H. et al., "Macrophage Migration Inhibitory Factor (MIF) Promotes Cell Survival by Activation of the Akt Pathway and Role for CSN5/JAB1 in the Control of Autocrine MIF Activity" Oncogene (Aug. 2, 2007) pp. 5046-5059, vol. 26, No. 35.

Leng, L. et al., "MIF Signal Transduction Initiated by Binding to CD74" The Journal of Experimental Medicine (Jun. 2, 2003) pp. 1467-1476, vol. 197, No. 11.

Supplementary European Search Report dated Oct. 10, 2011 issued in corresponding European Application No. EP 08 83 9285.

Rickove, K. et al., "Global Survey of Phosphotyrosine Signaling Identifed Oncogenic Kinase in Lung Cancer" Cell (Dec. 14, 2007) pp. 1190-1203, vol. 131.

International Search Report dated May 1, 2009 issued in corresponding International Publication No. WO 2009/051846 A3.

Lepetit, D. et al., "The cloning and characterization of a cDNA encoding *Xenopus laevis* DNA ligase I" Gene (Jun. 26, 1996) pp. 273-277, vol. 172, No. 2.

Scheffter, S.M. et al., "The Complete Sequence of Leishmania RNA Virus LRV2-1, a Virus of an Old World Parasite Strain" Virology (Sep. 10, 1995) pp. 84-90, vol. 212, No. 1.

(Continued)

*Primary Examiner* — James Martinell

(74) *Attorney, Agent, or Firm* — Scully, Scott, Murphy & Presser, P.C.

(57) ABSTRACT

In accordance with the invention, a novel gene translocation, (5q32, 6q22), in human non-small cell lung carcinoma (NSCLC) that results in a fusion proteins combining part of CD74 with Proto-oncogene Tyrosine Protein Kinase ROS Precursor (ROS) kinase has now been identified. The CD74-ROS fusion protein is anticipated to drive the proliferation and survival of a subgroup of NSCLC tumors. The invention therefore provides, in part, isolated polynucleotides and vectors encoding the disclosed mutant ROS kinase polypeptides, probes for detecting it, isolated mutant polypeptides, recombinant polypeptides, and reagents for detecting the fusion and truncated polypeptides. The disclosed identification of the new fusion protein enables new methods for determining the presence of these mutant ROS kinase polypeptides in a biological sample, methods for screening for compounds that inhibit the proteins, and methods for inhibiting the progression of a cancer characterized by the mutant polynucleotides or polypeptides, which are also provided by the invention.

21 Claims, 9 Drawing Sheets

(56) References Cited

OTHER PUBLICATIONS

Taillardat-Bisch, A.V. et al., "RNA polymerase beta-subunit-based phylogeny of *Ehrlichia* spp., *Anaplasma* spp., *Neorickettsia* spp. and *Wolbachia pipientis*" Int J Syst Evol Microbiol (Mar. 2003) pp. 455-458, vol. 53 part 2.

Official Action dated Jun. 4, 2013, issued in corresponding Japanese Patent Application No. 2010-529983, received from the Japanese Patent Office, together with full English-translation.

Official Action dated Jan. 28, 2015 received from the Canadian Patent Office in CA Application No. 2,702,686.

* cited by examiner

1A
Chr. 5
Chr. 6
CD74 (5q32)
ROS (6q22)
q34
q14.3
q11.2
p22.3
q27
q21
q14.1
q13
q12
1B
CD74
TM
ROS
Kinase Domain
TM
Extracellular Domain
1C
CD74
TM
TM
ROS
Kinase Domain
CD74 exon 7
ROS exon 34
FEMSRHSLEQKPTDAPPKDDFWIPETSFILTIIV

Figure 2

MHRRRSRSCREDQKPVMDDQRDLISNNEQLPMLGRRPGAPESKCSRGALYT
GFSILVTLLLAGQATTAYFLYQQQGRLDKLTVTSQNLQLENLRMKLPKPPKPVS
KMRMATPLLMQALPMGALPQGPMQNATKYGNMTEDHVMHLLQNADPLKVYP
PLKGSFPENLRHLKNTMETIDWKVFESWMHHWLLFEMSRHSLEQKPTDAPPK
DDFWIPETSFILTIIVGIFLVVTIPLTFVWHRRLKNQKSAKEGVTVLINEDKELAEL
RGLAAGVGLANACYAIHTLPTQEEIENLPAFPREKLTLRLLLGSGAFGEVYEGT
AVDILGVGSGEIKVAVKTLKKGSTDQEKIEFLKEAHLMSKFNHPNILKQLGVCL
LNEPQYIILELMEGGDLLTYLRKARMATFYGPLLTLVDLVDLCVDISKGCVYLE
RMHFIHRDLAARNCLVSVKDYTSPRIVKIGDFGLARDIYKNDYYRKRGEGLLPV
RWMAPESLMDGIFTTQSDVWSFGILIWEILTLGHQPYPAHSNLDVLNYVQTGG
RLEPPRNCPDDLWNLMTQCWAQEPDQRPTFHRIQDQLQLFRNFFLNSIYKSR
DEANNSGVINESFEGEDGDVICLNSDDIMPVALMETKNREGLNYMVLATECGQ
GEEKSEGPLGSQESESCGLRKEEKEPHADKDFCQEKQVAYCPSGKPEGLNYA
CLTHSGYGDGSD

ATGCACAGGAGGAGAAGCAGGAGCTGTCGGGAAGATCAGAAGCCAGTCAT
GGATGACCAGCGCGACCTTATCTCCAACAATGAGCAACTGCCCATGCTGGG
CCGGCGCCCTGGGGCCCCGGAGAGCAAGTGCAGCCGCGGAGCCCTGTAC
ACAGGCTTTTCCATCCTGGTGACTCTGCTCCTCGCTGGCCAGGCCACCACC
GCCTACTTCCTGTACCAGCAGCAGGGCCGGCTGGACAAACTGACAGTCAC
CTCCCAGAACCTGCAGCTGGAGAACCTGCGCATGAAGCTTCCCAAGCCTCC
CAAGCCTGTGAGCAAGATGCGCATGGCCACCCCGCTGCTGATGCAGGCGC
TGCCCATGGGAGCCCTGCCCCAGGGGCCCATGCAGAATGCCACCAAGTAT
GGCAACATGACAGAGGACCATGTGATGCACCTGCTCCAGAATGCTGACCCC
CTGAAGGTGTACCCGCCACTGAAGGGGAGCTTCCCGGAGAACCTGAGACA
CCTTAAGAACACCATGGAGACCATAGACTGGAAGGTCTTTGAGAGCTGGAT
GCACCATTGGCTCCTGTTTGAAATGAGCAGGCACTCCTTGGAGCAAAAGCC
CACTGACGCTCCACCGAAAGATGATTTTTGGATACCAGAAACAAGTTTCATA
CTTACTATTATAGTTGGAATATTTCTGGTTGTTACAATCCCACTGACCTTTGT
CTGGCATAGAAGATTAAAGAATCAAAAAAGTGCCAAGGAAGGGGTGACAGT
GCTTATAAACGAAGACAAAGAGTTGGCTGAGCTGCGAGGTCTGGCAGCCG
GAGTAGGCCTGGCTAATGCCTGCTATGCAATACATACTCTTCCAACCCAAGA
GGAGATTGAAAATCTTCCTGCCTTCCCTCGGGAAAAACTGACTCTGCGTCT
CTTGCTGGGAAGTGGAGCCTTTGGAGAAGTGTATGAAGGAACAGCAGTG
GACATCTTAGGAGTTGGAAGTGGAGAAATCAAAGTAGCAGTGAAGACTTT
GAAGAAGGGTTCCACAGACCAGGAGAAGATTGAATTCCTGAAGGAGGCA
CATCTGATGAGCAAATTTAATCATCCCAACATTCTGAAGCAGCTTGGAGTT
TGTCTGCTGAATGAACCCCAATACATTATCCTGGAACTGATGGAGGGAGG
AGACCTTCTTACTTATTTGCGTAAAGCCCGGATGGCAACGTTTTATGGTCC
TTTACTCACCTTGGTTGACCTTGTAGACCTGTGTGTAGATATTTCAAAAGG

Fig. 2 (cont.)

CTGTGTCTACTTGGAACGGATGCATTTCATTCACAGGGATCTGGCAGCTAG
AAATTGCCTTGTTTCCGTGAAAGACTATACCAGTCCACGGATAGTGAAGAT
TGGAGACTTTGGACTCGCCAGAGACATCTATAAAAATGATTACTATAGAAA
GAGAGGGGAAGGCCTGCTCCCAGTTCGGTGGATGGCTCCAGAAAGTTTG
ATGGATGGAATCTTCACTACTCAATCTGATGTATGGTCTTTTGGAATTCTGA
TTTGGGAGATTTTAACTCTTGGTCATCAGCCTTATCCAGCTCATTCCAACCT
TGATGTGTTAAACTATGTGCAAACAGGAGGGAGACTGGAGCCACCAAGAA
ATTGTCCTGATGATCTGTGGAATTTAATGACCCAGTGCTGGGCTCAAGAAC
CCGACCAAAGACCTACTTTTCATAGAATTCAGGACCAACTTCAGTTATTCA
GAAATTTTTTCTTAAATAGCATTTATAAGTCCAGAGATGAAGCAAACAACAGT
GGAGTCATAAATGAAAGCTTTGAAGGTGAAGATGGCGATGTGATTTGTTTGA
ATTCAGATGACATTATGCCAGTTGCTTTAATGGAAACGAAGAACCGAGAAGG
GTTAAACTATATGGTACTTGCTACAGAATGTGGCCAAGGTGAAGAAAAGTCT
GAGGGTCCTCTAGGCTCCCAGGAATCTGAATCTTGTGGTCTGAGGAAAGAA
GAGAAGGAACCACATGCAGACAAAGATTTCTGCCAAGAAAAACAAGTGGCT
TACTGCCCTTCTGGCAAGCCTGAAGGCCTGAACTATGCCTGTCTCACTCAC
AGTGGATATGGAGATGGGTCTGATTAA

Figure 3

MHRRRSRSCREDQKPVMDDQRDLISNNEQLPMLGRRPGAPESKCSRGALY
TGFSILVTLLLAGQATTAYFLYQQQGRLDKLTVTSQNLQLENLRMKLPKP
PKPVSKMRMATPLLMQALPMGALPQGPMQNATKYGNMTEDHVMHLLQNAD
PLKVYPPLKGSFPENLRHLKNTMETIDWKVFESWMHHWLLFEMSRHSLEQ
KPTDAPPKVLTKCQEEVSHIPAVHPGSFRPKCDENGNYLPLQCYGSIGYC
WCVFPNGTEVPNTRSRGHHNCSESLELEDPSSGLGVTKQDLGPAPL

CAGGGTCCCAGATGCACAGGAGGAGAAGCAGGAGCTGTCGGGAAGATCAG
AAGCCAGTCATGGATGACCAGCGCGACCTTATCTCCAACAATGAGCAACT
GCCCATGCTGGGCCGGCGCCCTGGGGCCCCGGAGAGCAAGTGCAGCCGCG
GAGCCCTGTACACAGGCTTTTCCATCCTGGTGACTCTGCTCCTCGCTGGC
CAGGCCACCACCGCCTACTTCCTGTACCAGCAGCAGGGCCGGCTGGACAA
ACTGACAGTCACCTCCCAGAACCTGCAGCTGGAGAACCTGCGCATGAAGC
TTCCCAAGCCTCCCAAGCCTGTGAGCAAGATGCGCATGGCCACCCCGCTG
CTGATGCAGGCGCTGCCCATGGGAGCCCTGCCCCAGGGGCCCATGCAGAA
TGCCACCAAGTATGGCAACATGACAGAGGACCATGTGATGCACCTGCTCC
AGAATGCTGACCCCCTGAAGGTGTACCCGCCACTGAAGGGGAGCTTCCCG
GAGAACCTGAGACACCTTAAGAACACCATGGAGACCATAGACTGGAAGGT
CTTTGAGAGCTGGATGCACCATTGGCTCCTGTTTGAAATGAGCAGGCACT
CCTTGGAGCAAAAGCCCACTGACGCTCCACCGAAAGTACTGACCAAGTGC
CAGGAAGAGGTCAGCCACATCCCTGCTGTCCACCCGGGTTCATTCAGGCC
CAAGTGCGACGAGAACGGCAACTATCTGCCACTCCAGTGCTATGGGAGCA
TCGGCTACTGCTGGTGTGTCTTCCCCAACGGCACGGAGGTCCCCAACACC
AGAAGCCGCGGGCACCATAACTGCAGTGAGTCACTGGAACTGGAGGACCC
GTCTTCTGGGCTGGGTGTGACCAAGCAGGATCTGGGCCCAGCTCCTTTG

Figure 4A

MKNIYCLIPKLVNFATLGCLWISVVQCTVLNSCLKSCVTNLGQQLDLGTPHNLSEPCIQG
CHFWNSVDQKNCALKCRESCEVGCSSAEGAYEEEVLENADLPTAPFASSIGSHNMTLRWK
SANFSGVKYIIQWKYAQLLGSWTYTKTVSRPSYVVKPLHPFTEYIFRVVWIFTAQLQLYS
PPSPSYRTHPHGVPETAPLIRNIESSSPDTVEVSWDPPQFPGGPILGYNLRLISKNQKLD
AGTQRTSFQFYSTLPNTIYRFSIAAVNEVGEGPEAESSITTSSSAVQQEEQWLFLSRKTS
LRKRSLKHLVDEAHCLRLDAIYHNITGISVDVHQQIVYFSEGTLIWAKKAANMSDVSDLR
IFYRGSGLISSISIDWLYQRMYFIMDELVCVCDLENCSNIEEITPPSISAPQKIVADSYN
GYVFYLLRDGIYRADLPVPSGRCAEAVRIVESCTLKDFAIKPQAKRIIYFNDTAQVFMST
FLDGSASHLILPRIPFADVKSFACENNDFLVTDGKVIFQQDALSFNEFIVGCDLSHIEEF
GFGNLVIFGSSSQLHPLPGRPQELSVLFGSHQALVQWKPPALAIGANVILISDIIELFEL
GPSAWQNWTYEVKVSTQDPPEVTHIFLNISGTMLNVPELQSAMKYKVSVRASSPKRPGPW
SEPSVGTTLVPASEPPFIMAVKEDGLWSKPLNSFGPGEFLSSDIGNVSDMDWYNNSLYYS
DTKGDVFVWLLNGTDISENYHLPSIAGAGALAFEWLGHFLYWAGKTYVIQRQSVLTGHTD
IVTHVKLLVNDMVVDSVGGYLYWTTLYSVESTRLNGESSLVLQTQPWFSGKKVIALTLDL
SDGLLYWLVQDSQCIHLYTAVLRGQSTGDTTITEFAAWSTSEISQNALMYYSGRLFWING
FRIITTQEIGQKTSVSVLEPARFNQFTIIQTSLKPLPGNFSFTPKVIPDSVQESSFRIEG
NASSFQILWNGPPAVDWGVVFYSVEFSAHSKFLASEQHSLPVFTVEGLEPYALFNLSVTP
YTYWGKGPKTSLSLRAPETVPSAPENPRIFILPSGKCCNKNEVVVEFRWNKPKHENGVLT
KFEIFYNISNQSITNKTCEDWIAVNVTPSVMSFQLEGMSPRCFIAFQVRAFTSKGPGPYA
DVVKSTTSEINPFPHLITLLGNKIVFLDMDQNQVVWTFSAERVISAVCYTADNEMGYYAE
GDSLFLLHLHNRSSSELFQDSLVFDITVITIDWISRHLYFALKESQNGMQVFDVDLEHKV
KYPREVKIHNRNSTIISFSVYPLLSRLYWTEVSNFGYQMFYYSIISHTLHRILQPTATNQ
QNKRNQCSCNVTEFELSGAMAIDTSNLEKPLIYFAKAQEIWAMDLEGCQCWRVITVPAML
AGKTLVSLTVDGDLIYWIITAKDSTQIYQAKKGNGAIVSQVKALRSRHILAYSSVMQPFP
DKAFLSLASDTVEPTILNATNTSLTIRLPLAKTNLTWYGITSPTPTYLVYYAEVNDRKNS
SDLKYRILEFQDSIALIEDLQPFSTYMIQIAVKNYYSDPLEHLPPGKEIWGKTKNGVPEA
VQLINTTVRSDTSLIISWRESHKPNGPKESVRYQLAISHLALIPETPLRQSEFPNGRLTL
LVTRLSGGNIYVLKVLACHSEEMWCTESHPVTVEMFNTPEKPYSLVPENTSLQFNWKAPL
NVNLIRFWVELQKWKYNEFYHVKTSCSQGPAYVCNITNLQPYTSYNVRVVVVYKTGENST
SLPESFKTKAGVPNKPGIPKLLEGSKNSIQWEKAEDNGCRITYYILEIRKSTSNNLQNQN
LRWKMTFNGSCSSVCTWKSKNLKGIFQFRVVAANNLGFGEYSGISENIILVGDDFWIPET
SFILTIIVGIFLVVTIPLTFVWHRRLKNQKSAKEGVTVLINEDKELAELRGLAAGVGLAN
ACYAIHTLPTQEEIENLPAFPREKLTLRLLLGSGAFGEVYEGTAVDILGVGSGEIKVAVK
TLKKGSTDQEKIEFLKEAHLMSKFNHPNILKQLGVCLLNEPQYIILELMEGGDLLTYLRK
ARMATFYGPLLTLVDLVDLCVDISKGCVYLERMHFIHRDLAARNCLVSVKDYTSPRIVKI
GDFGLARDIYKNDYYRKRGEGLLPVRWMAPESLMDGIFTTQSDVWSFGILIWEILTLGHQ
PYPAHSNLDVLNYVQTGGRLEPPRNCPDDLWNLMTQCWAQEPDQRPTFHRIQNQLQLFRN
FFLNSIYQCRDEANNSGVINESFEGEDGDVICLNSDDIMPVVLMETKNREGLNYMVLATE
CGQGEEKSEGPLGSQESESCGLRKEEKEPHADKDFCQEKQVAYCPSGKPEGLNYACLTHS
GYGDGSD

Figure 4B

```
   1 caagctttca agcattcaaa ggtctaaatg aaaaaggcta agtattattt caaaaggcaa
  61 gtatatccta atatagcaaa acaaacaaag caaaatccat cagctactcc tccaattgaa
 121 gtgatgaagc ccaaataatt catatagcaa aatggagaaa attagaccgg ccatctaaaa
 181 atctgccatt ggtgaagtga tgaagaacat ttactgtctt attccgaagc ttgtcaattt
 241 tgcaactctt ggctgcctat ggatttctgt ggtgcagtgt acagttttaa atagctgcct
 301 aaagtcgtgt gtaactaatc tgggccagca gcttgacctt ggcacaccac ataatctgag
 361 tgaaccgtgt atccaaggat gtcacttttg gaactctgta gatcagaaaa actgtgcttt
 421 aaagtgtcgg gagtcgtgtg aggttggctg tagcagcgcg gaaggtgcat atgaagagga
 481 agtactggaa aatgcagacc taccaactgc tccctttgct tcttccattg gaagccacaa
 541 tatgacatta cgatggaaat ctgcaaactt ctctggagta aaatacatca ttcagtggaa
 601 atatgcacaa cttctgggaa gctggactta tactaagact gtgtccagac cgtcctatgt
 661 ggtcaagccc ctgcacccct tcactgagta cattttccga gtggtttgga tcttcacagc
 721 gcagctgcag ctctactccc ctccaagtcc cagttacagg actcatcctc atggagttcc
 781 tgaaactgca cctttgatta ggaatattga gagctcaagt cccgacactg tggaagtcag
 841 ctgggatcca cctcaattcc caggtggacc tattttgggt tataacttaa ggctgatcag
 901 caaaaatcaa aaattagatg cagggacaca gagaaccagt ttccagtttt actccacttt
 961 accaaatact atctacaggt tttctattgc agcagtaaat gaagttggtg agggtccaga
1021 agcagaatct agtattacca cttcatcttc agcagttcaa caagaggaac agtggctctt
1081 tttatccaga aaaacttctc taagaaagag atctttaaaa catttagtag atgaagcaca
1141 ttgccttcgg ttggatgcta tataccataa tattacagga atatctgttg atgtccacca
1201 gcaaattgtt tatttctctg aaggaactct catatgggcg aagaaggctg ccaacatgtc
1261 tgatgtatct gacctgagaa ttttttacag aggttcagga ttaatttctt ctatctccat
1321 agattggctt tatcaaagaa tgtatttcat catggatgaa ctggtatgtg tctgtgattt
1381 agagaactgc tcaaacatcg aggaaattac tccaccctct attagtgcac ctcaaaaaat
1441 tgtggctgat tcatacaatg ggtatgtctt ttacctcctg agagatggca tttatagagc
1501 agaccttcct gtaccatctg gccggtgtgc agaagctgtg cgtattgtgg agagttgcac
1561 gttaaaggac tttgcaatca agccacaagc caagcgaatc atttacttca atgacactgc
1621 ccaagtcttc atgtcaacat ttctggatgg ctctgcttcc catctcatcc tacctcgcat
1681 cccctttgct gatgtgaaaa gttttgcttg tgaaaacaat gactttcttg tcacagatgg
1741 caaggtcatt ttccaacagg atgctttgtc ttttaatgaa ttcatcgtgg gatgtgacct
1801 gagtcacata gaagaatttg ggtttggtaa cttggtcatc tttggctcat cctcccagct
1861 gcaccctctg ccaggccgcc cgcaggagct ttcggtgctg tttggctctc accaggctct
1921 tgttcaatgg aagcctcctg cccttgccat aggagccaat gtcatcctga tcagtgatat
1981 tattgaactc tttgaattag gcccttctgc ctggcagaac tggacctatg aggtgaaagt
2041 atccacccaa gaccctcctg aagtcactca tattttcttg aacataagtg gaaccatgct
2101 gaatgtacct gagctgcaga gtgctatgaa atacaaggtt tctgtgagag caagttctcc
2161 aaagaggcca ggcccctggt cagagccctc agtgggtact accctggtgc cagctagtga
2221 accaccattt atcatggctg tgaaagaaga tgggctttgg agtaaaccat taaatagctt
2281 tggcccagga gagttcttat cctctgatat aggaaatgtg tcagacatgg attggtataa
2341 caacagcctc tactacagtg acacgaaagg cgacgttttt gtgtggctgc tgaatgggac
2401 ggatatctca gagaattatc acctacccag cattgcagga gcaggggctt tagcttttga
2461 gtggctgggt cactttctct actgggctgg aaagacatat gtgatacaaa ggcagtctgt
2521 gttgacggga cacacagaca ttgttaccca cgtgaagcta ttggtgaatg acatggtggt
2581 ggattcagtt ggtggatatc tctactggac cacactctat tcagtggaaa gcaccagact
2641 aaatggggaa agttcccttg tactacagac acagccttgg ttttctggga aaaaggtaat
2701 tgctctaact ttagacctca gtgatgggct cctgtattgg ttggttcaag acagtcaatg
2761 tattcacctg tacacagctg ttcttcgggg acagagcact ggggatacca ccatcacaga
2821 atttgcagcc tggagtactt ctgaaatttc ccagaatgca ctgatgtact atagtggtcg
2881 gctgttctgg atcaatggct ttaggattat cacaactcaa gaaataggtc agaaaaccag
2941 tgtctctgtt ttggaaccag ccagatttaa tcagttcaca attattcaga catcccttaa
3001 gcccctgcca gggaactttt cctttacccc taaggttatt ccagattctg ttcaagagtc
3061 ttcatttagg attgaaggaa atgcttcaag ttttcaaatc ctgtggaatg gtccccctgc
3121 ggtagactgg ggtgtagttt tctacagtgt agaatttagt gctcattcta agttcttggc
3181 tagtgaacaa cactctttac ctgtatttac tgtggaagga ctggaacctt atgccttatt
3241 taatctttct gtcactcctt atacctactg ggaaagggc cccaaaacat ctctgtcact
3301 tcgagcacct gaaacagttc catcagcacc agagaacccc agaatattta tattaccaag
3361 tggaaaatgc tgcaacaaga atgaagttgt ggtggaattt aggtggaaca aacctaagca
3421 tgaaaatggg gtgttaacaa aatttgaaat tttctacaat atatccaatc aaagtattac
3481 aaacaaaaca tgtgaagact ggattgctgt caatgtcact ccctcagtga tgtcttttca
3541 acttgaaggc atgagtccca gatgctttat tgccttccag gttagggcct ttacatctaa
3601 ggggccagga ccatatgctg acgttgtaaa gtctacaaca tcagaaatca acccatttcc
```

Fig. 4B (cont.)

```
3661 tcacctcata actcttcttg gtaacaagat agttttttta gatatggatc aaaatcaagt
3721 tgtgtggacg ttttcagcag aaagagttat cagtgccgtt tgctacacag ctgataatga
3781 gatgggatat tatgctgaag ggactcact ctttcttctg cacttgcaca atcgctctag
3841 ctctgagctt ttccaagatt cactggtttt tgatatcaca gttattacaa ttgactggat
3901 ttcaaggcac ctctactttg cactgaaaga atcacaaaat ggaatgcaag tatttgatgt
3961 tgatcttgaa cacaaggtga aatatcccag agaggtgaag attcacaata ggaattcaac
4021 aataatttct ttttctgtat atcctctttt aagtcgcttg tattggacag aagtttccaa
4081 ttttggctac cagatgttct actacagtat tatcagtcac accttgcacc gaattctgca
4141 acccacagct acaaaccaac aaaacaaaag gaatcaatgt tcttgtaatg tgactgaatt
4201 tgagttaagt ggagcaatgg ctattgatac ctctaaccta gagaaaccat tgatatactt
4261 tgccaaagca caagagatct gggcaatgga tctggaaggc tgtcagtgtt ggagagttat
4321 cacagtacct gctatgctcg caggaaaaac ccttgttagc ttaactgtgg atggagatct
4381 tatatactgg atcatcacag caaaggacag cacacagatt tatcaggcaa agaaaggaaa
4441 tggggccatc gtttcccagg tgaaggccct aaggagtagg catatcttgg cttacagttc
4501 agttatgcag ccttttccag ataaagcgtt tctgtctcta gcttcagaca ctgtggaacc
4561 aactatactt aatgccacta acactagcct cacaatcaga ttacctctgg ccaagacaaa
4621 cctcacatgg tatggcatca ccagccctac tccaacatac ctggtttatt atgcagaagt
4681 taatgacagg aaaaacagct ctgacttgaa atatagaatt ctggaatttc aggacagtat
4741 agctcttatt gaagatttac aaccattttc aacatacatg atacagatag ctgtaaaaaa
4801 ttattattca gatcctttgg aacatttacc accaggaaaa gagatttggg gaaaaactaa
4861 aaatggagta ccagaggcag tgcagctcat taatacaact gtgcggtcag acaccagcct
4921 cattatatct tggagagaat ctcacaagcc aaatggacct aaagaatcag tccgttatca
4981 gttggcaatc tcacacctgg ccctaattcc tgaaactcct ctaagacaaa gtgaatttcc
5041 aaatggaagg ctcactctcc ttgttactag actgtctggt ggaaatattt atgtgttaaa
5101 ggttcttgcc tgccactctg aggaaatgtg gtgtacagag agtcatcctg tcactgtgga
5161 aatgtttaac acaccagaga aaccttattc cttggttcca gagaacacta gtttgcaatt
5221 taattggaag gctccattga atgttaacct catcagattt tgggttgagc tacagaagtg
5281 gaaatacaat gagttttacc atgttaaaac ttcatgcagc caaggtcctg cttatgtctg
5341 taatatcaca aatctacaac cttatacttc atataatgtc agagtagtgg tggtttataa
5401 gacgggagaa aatagcacct cacttccaga aagctttaag acaaaagctg gagtcccaaa
5461 taaaccaggc attcccaaat tactagaagg gagtaaaaat tcaatacagt gggagaaagc
5521 tgaagataat ggatgtagaa ttacatacta tatccttgag ataagaaaga gcacttcaaa
5581 taatttacag aaccagaatt taaggtggaa gatgacattt aatggatcct gcagtagtgt
5641 ttgcacatgg aagtccaaaa acctgaaagg aatatttcag ttcagagtag tagctgcaaa
5701 taatctaggg tttggtgaat atagtggaat cagtgagaat attatattag ttggagatga
5761 tttttggata ccagaaacaa gtttcatact tactattata gttggaatat ttctggttgt
5821 tacaatccca ctgacctttg tctggcatag aagattaaag aatcaaaaaa gtgccaagga
5881 aggggtgaca gtgcttataa acgaagacaa agagttggct gagctgcgag gtctggcagc
5941 cggagtaggc ctggctaatg cctgctatgc aatacatact cttccaaccc aagaggagat
6001 tgaaaatctt cctgccttcc ctcgggaaaa actgactctg cgtctcttgc tgggaagtgg
6061 agcctttgga gaagtgtatg aaggaacagc agtggacatc ttaggagttg gaagtggaga
6121 aatcaaagta gcagtgaaga ctttgaagaa gggttccaca gaccaggaga agattgaatt
6181 cctgaaggag gcacatctga tgagcaaatt taatcatccc aacattctga agcagcttgg
6241 agtttgtctg ctgaatgaac cccaatacat tatcctggaa ctgatggagg gaggagacct
6301 tcttacttat ttgcgtaaag cccggatggc aacgttttat ggtcctttac tcaccttggt
6361 tgaccttgta gacctgtgtg tagatatttc aaaaggctgt gtctacttgg aacggatgca
6421 tttcattcac aggatctgg cagctagaaa ttgccttgtt tccgtgaaag actataccag
6481 tccacggata gtgaagattg gagactttgg actcgccaga gacatctata aaaatgatta
6541 ctatagaaag agaggggaag gcctgctccc agttcggtgg atggctccag aaagtttgat
6601 ggatggaatc ttcactactc aatctgatgt atggtctttt ggaattctga tttgggagat
6661 tttaactctt ggtcatcagc cttatccagc tcattccaac cttgatgtgt taaactatgt
6721 gcaaacagga gggagactgg agccaccaag aaattgtcct gatgatctgt ggaatttaat
6781 gacccagtgc tgggctcaag aacccgacca aagacctact tttcatagaa ttcaggacca
6841 acttcagtta ttcagaaatt ttttcttaaa tagcatttat aagtccagag atgaagcaaa
6901 caacagtgga gtcataaatg aaagctttga aggtgaagat ggcgatgtga tttgtttgaa
6961 ttcagatgac attatgccag ttgctttaat ggaaacgaag aaccgagaag ggttaaacta
7021 tatggtactt gctacagaat gtggccaagg tgaagaaaag tctgagggtc ctctaggctc
7081 ccaggaatct gaatcttgtg gtctgaggaa agaagagaag gaaccacatg cagacaaaga
7141 tttctgccaa gaaaaacaag tggcttactg cccttctggc aagcctgaag gcctgaacta
7201 tgcctgtctc actcacagtg gatatggaga tgggtctgat taatagcgtt gtttgggaaa
7261 tagagagttg agataaacac tctcattcag tagttactga aagaaaactc tgctagaatg
7321 ataaatgtca tggtggtcta taactccaaa taaacaatgc aacgttcc
```

CD74-ROS

CD74-F1: GCAGAATGCCACCAAGTATGGCAA
ROS-GSP3: TGCCAGACAAAGGTCAGTGGGATT

TRANSLOCATION AND MUTANT ROS KINASE IN HUMAN NON-SMALL CELL LUNG CARCINOMA

RELATED APPLICATIONS

This is a National Stage Entry of International Application No. PCT/US2008/011968 filed Oct. 20, 2008, which itself claims priority to U.S. Ser. No. 60/999,668 Filed Oct. 18, 2007, the entire contents of both of which are incorporated by reference herein.

FIELD OF THE INVENTION

The invention relates generally to proteins and genes involved in cancer, and to the detection, diagnosis and treatment of cancer.

BACKGROUND OF THE INVENTION

Many cancers are characterized by disruptions in cellular signaling pathways that lead to aberrant control of cellular processes, or to uncontrolled growth and proliferation of cells. These disruptions are often caused by changes in the activity of particular signaling proteins, such as kinases. Among these cancers is non-small cell lung carcinoma (NSCLC). NSCLC is the leading cause of cancer death in the United States, and accounts for about 87% of all lung cancers. There are about 151,000 new cases of NSCLC in the United States annually, and it is estimated that over 120,000 patients will die annually from the disease in the United States alone. See "*Cancer Facts and Figures* 2005," American Cancer Society. NSCLC, which comprises three distinct subtypes, is often only detected after it has metastasized, and thus the mortality rate is 75% within two years of diagnosis.

It is known that gene translocations resulting in kinase fusion proteins with aberrant signaling activity can directly lead to certain cancers. For example, it has been directly demonstrated that the BCR-ABL oncoprotein, a tyrosine kinase fusion protein, is the causative agent in human chronic myelogenous leukemia (CML). The BCR-ABL oncoprotein, which is found in at least 90-95% of CML cases, is generated by the translocation of gene sequences from the c-ABL protein tyrosine kinase on chromosome 9 into BCR sequences on chromosome 22, producing the so-called Philadelphia chromosome. See, e.g. Kurzock et al., *N. Engl. J. Med.* 319: 990-998 (1988). The translocation is also observed in acute lymphocytic leukemia and AML cases.

Gene translocations leading to mutant or fusion proteins implicated in a variety of other cancers have been described. For example, Falini et al., *Blood* 99(2): 409-426 (2002), review translocations known to occur in hematological cancers. To date, only a limited number of gene translocations and mutant proteins occurring in lung cancers have been described, including the t(15; 19) translocation involving Notch3. See Dang et al., *J. Natl. Can. Instit.* 92(16): 1355-1357 (2000). Defects in RNA Binding Protein-6 (RBM-6) expression and/or activity have been found in small cell and non-small cell lung carcinomas. See Drabkin et al., *Oncogene* 8(16): 2589-97 (1999). However, to date, no translocations in human NSCLC cancer that involve protein kinases have been described.

CD74 is an integral membrane protein that functions as a MHC class II chaperone protein. Defects in ROS kinase expression resulting from the FIG-ROS del(6)(q21,q21) translocation in glioblastoma have been described. See Charest et al., *Genes Chromos. Canc.* 37(1): 58-71 (2003). A truncated form of ROS kinase able to drive tumor growth in mice has also been described. See Birchmeier et al., *Mol. Cell. Bio.* 6(9): 3109-3115 (1986). To date, there are no known activating point mutations that occur in ROS kinase.

Identifying translocations and mutations in human cancers is highly desirable because it can lead to the development of new therapeutics that target such fusion or mutant proteins, and to new diagnostics for identifying patients that have such gene translocations. For example, BCR-ABL has become a target for the development of therapeutics to treat leukemia. Most recently, Gleevec® (Imatinib mesylate, STI-571), a small molecule inhibitor of the ABL kinase, has been approved for the treatment of CML. This drug is the first of a new class of anti-proliferative agents designed to interfere with the signaling pathways that drive the growth of tumor cells. The development of this drug represents a significant advance over the conventional therapies for CML and ALL, chemotherapy and radiation, which are plagued by well known side-effects and are often of limited effect since they fail to specifically target the underlying causes of the malignancies. Likewise, reagents and methods for specifically detecting BCR-ABL fusion protein in patients, in order to identify patients most likely to respond to targeted inhibitors like Gleevec®, have been described.

Accordingly, there remains a need for the identification of novel gene translocations or mutations resulting in fusion or mutant proteins implicated in the progression of human cancers, including lung cancers like NSCLC, and the development of new reagents and methods for the study and detection of such fusion proteins. Identification of such fusion proteins will, among other things, desirably enable new methods for selecting patients for targeted therapies, as well as for the screening of new drugs that inhibit such mutant/fusion proteins.

SUMMARY OF THE INVENTION

In accordance with the invention, a novel gene translocation, (5q32, 6q22), in human non-small cell lung carcinoma (NSCLC) that results in fusion proteins combining part of CD74 with Proto-Oncogene Tyrosine Protein Kinase ROS precursor (ROS) kinase have now been identified. The CD74-ROS fusion proteins are expected to retain ROS tyrosine kinase activity and to drive the proliferation and survival of NSCLC in a subset of such cancers in which the fusion protein is expressed.

The invention therefore provides, in part, isolated polynucleotides and vectors encoding the disclosed mutant ROS polypeptides, probes and assays for detecting them, isolated mutant ROS polypeptides, recombinant mutant polypeptides, and reagents for detecting the mutant ROS polynucleotides and polypeptides. The disclosed identification of the new mutant ROS kinase proteins and CD74 translocation enables new methods for determining the presence of mutant ROS polynucleotides or polypeptides in a biological sample, methods for screening for compounds that inhibit the mutant kinase proteins, and methods for inhibiting the progression of a cancer characterized by the expression of mutant ROS polynucleotides or polypeptides, which are also provided by the invention. The aspects and embodiments of the invention are described in more detail below.

BRIEF DESCRIPTION OF THE DRAWINGS

FIG. 2—is the amino acid sequence (1 letter code) of the human CD74-ROS fusion protein (SEQ ID NO: 1) (top panel) with coding DNA sequence also indicated (SEQ ID NO: 2) (bottom panel); the residues of the CD74 moiety are underlined, while the residues of the kinase domain of ROS are in bold.

FIG. 3—is the amino acid sequence (1 letter code) of human CD74 protein (SEQ ID NO: 3) (SwissProt Accession No. P04233) (top panel) with coding DNA sequence also indicated (SEQ ID NO: 4) (GeneBank Accession No. NM_001025159) (bottom panel); the residues involved in the translocation are underlined.

FIG. 4A—is the amino acid sequence (1 letter code) of human
ROS kinase (SEQ ID NO: 5) (SwissProt Accession No. P08922); the residues involved in the translocation are underlined.

FIG. 4B—is the coding DNA sequence of human ROS kinase (SEQ ID NO: 6) (GeneBank Accession No. NM_002944); the residues involved in the translocation are underlined.

DETAILED DESCRIPTION OF THE INVENTION

Figure 1:
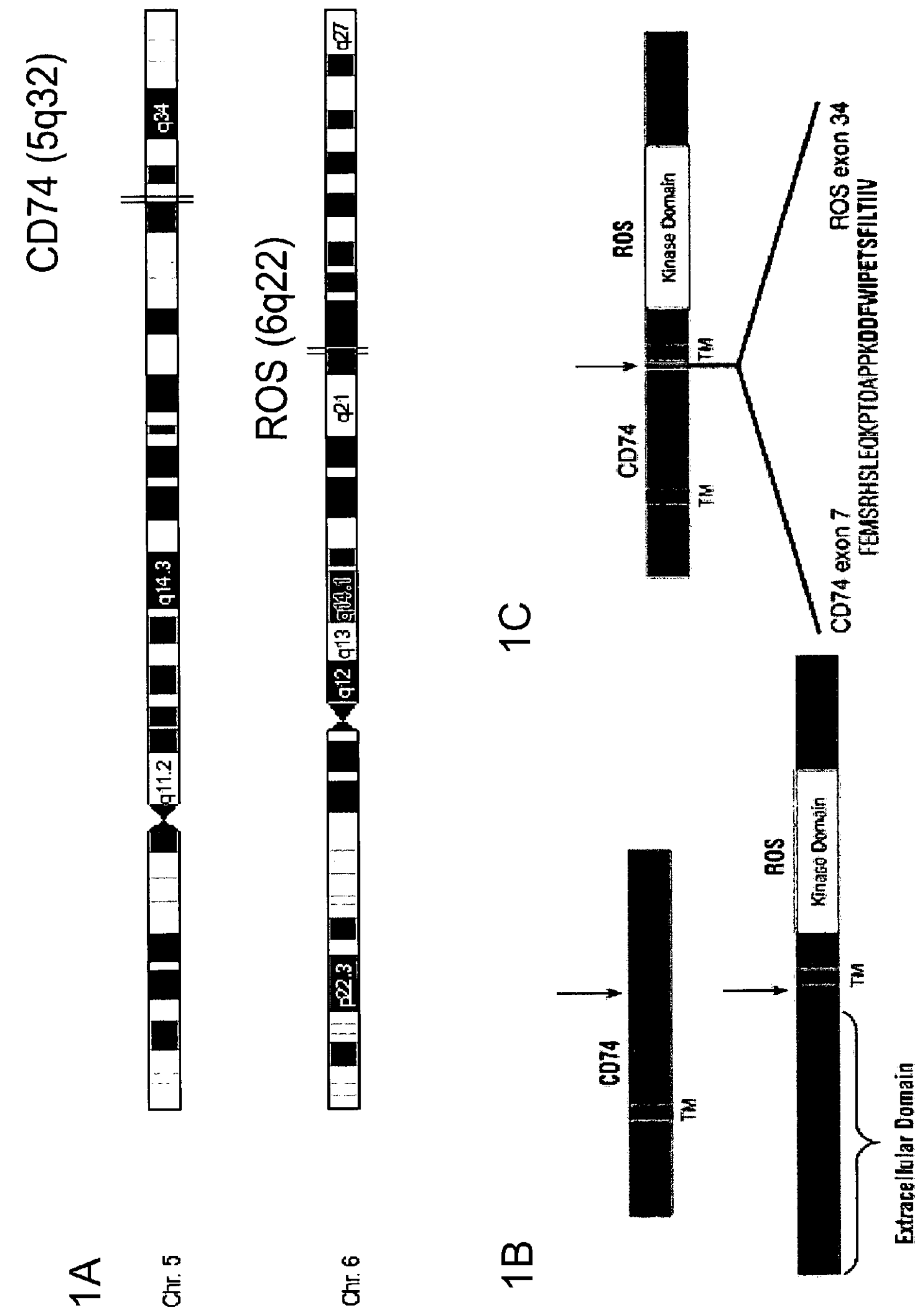
FIG. 1—shows the location of the CD74 gene and ROS gene on chromosomes 5q and 6q respectively (FIG. 1A), and the domain locations of full length CD74 and ROS proteins as well as those CD74-ROS fusion protein (FIG. 1B and FIG. 1C). The fusion junction occurs at residue 1853 upstream of the transmembrane domain of ORS.

In accordance with the invention, a previously unknown gene translocation that results in a mutant kinase fusion protein, CD74-ROS, has now been identified in human non-small cell lung carcinoma (NSCLC), a subtype of lung carcinoma. The translocation, which occurs between chromosome (5q32) and chromosome (6q22), produces a fusion protein that combines the N-terminus of CD74, with the transmembrane and kinase domains of Proto-Oncogene Tyrosine Protein Kinase ROS precursor (ROS) kinase, a 2347 amino acid receptor tyrosine kinase. The resulting CD74-ROS fusion protein, a 703 amino acid protein, is expected to retain kinase activity and to drive the proliferation and survival of a subset of human NSCLC tumors in which the fusion protein is expressed.

Although a few gene translocations that result in aberrant fusion proteins involving ROS kinase have been described, including the FIG-ROS del(6)(q21,q21) translocation in glioblastoma (see Charest et al., (2003), supra.) and a truncated, active form of ROS (see Birchmeier et al., supra.), the presently disclosed CD74-ROS translocation and fusion protein is novel, and this fusion kinase is the first reported in primary human NSCLC patient. CD74 is an integral membrane protein that functions as a MHC class II chaperone protein. ROS is a transmembrane receptor tyrosine kinase that belongs to the insulin receptor subfamily, and is involved in cell proliferation and differentiation processes. ROS is expressed, in humans, in epithelial cells of a variety of different tissues. Defects in ROS expression and/or activation have been found in glioblastoma, as well as tumors of the central nervous system. See e.g. Charest et al. (2003), supra.

As further described below, the CD74-ROS translocation gene and fusion protein have presently been isolated and sequenced, and cDNAs for expressing the mutant kinase protein produced. Accordingly, the invention provides, in part, isolated polynucleotides that encode CD74-ROS fusion polypeptides, nucleic acid probes that hybridize to such polynucleotides, and methods, vectors, and host cells for utilizing such polynucleotides to produce recombinant mutant ROS polypeptides. The invention also provides, in part, isolated polypeptides comprising amino acid sequences encoding CD74-ROS fusion polypeptides, recombinant mutant polypeptides, and isolated reagents that specifically bind to and/or detect CD74-ROS fusion polypeptides, but do not bind to or detect either wild type CD74 or wild type ROS. These aspects of the invention, which are described in further detail below, will be useful, inter alia, in further studying the mechanisms of cancers driven by mutant ROS kinase expression/activity, for identifying lung carcinomas and other cancers characterized by the CD74-ROS translocation and/or fusion proteins, and in practicing methods of the invention as further described below.

The identification of the novel ROS kinase mutants and translocation has important implications for the potential diagnosis and treatment of diseases, such as NSCLC, that are characterized by this translocation and/or fusion protein. NSCLC is the leading cause of cancer death in the United States, and is often difficult to diagnose until after it has metastasized, increasing the difficulty of effectively treating or curing this disease. The mortality rate of NSCLC is therefore 75% within two years of diagnosis. See American Cancer Society, supra. Although targeted EGFR-inhibitors are presently approved for the treatment of NSCLC, it is anticipated that this therapy may be partially or wholly ineffective against those patients having tumors in which mutant ROS kinase (rather than or in addition to EGFR) is expressed and driving the disease, in whole or in part.

Therefore, the present discovery of the CD74-ROS fusion proteins resulting from gene translocation in NSCLC, which is expected to drive proliferation and survival in a subset of NSCLC tumors, enables important new methods for accurately identifying mammalian lung cancers (such as NSCLC), as well as other cancers, in which CD74-ROS fusion protein or truncated ROS kinase is expressed. These tumors are most likely to respond to inhibitors of the kinase activity of the mutant ROS kinases. The ability to identify, as early as possible, cancers that are driven by a mutant ROS kinase will greatly assist in clinically determining which therapeutic, or combination of therapeutics, will be most appropriate for a particular patient, thus helping to avoid prescription of inhibitors targeting other kinases that are not, in fact, the primary signaling molecule driving the cancer.

Accordingly, the invention provides, in part, methods for detecting the presence of a CD74-ROS translocation (t(5,6) (q32, q22) and/or fusion polypeptide in a cancer using fusion-specific and mutant-specific reagents of the invention. Such methods may be practiced, for example, to identify a cancer, such as a NSCLC tumor, that is likely to respond to an inhibitor of the ROS kinase activity of the mutant protein. The invention also provides, in part, methods for determining whether a compound inhibits the progression of a cancer characterized by a CD74-ROS fusion polypeptide. Further provided by the invention is a method for inhibiting the progression of a cancer that expresses a CD74-ROS fusion polypeptide by inhibiting the expression and/or activity of the mutant polypeptide. Such methods are described in further detail below. Any suitable materials and/or methods known to those of skill can be utilized in carrying out the present invention. However, preferred materials and methods are described. Materials, reagents and the like to which reference is made in the following description and examples are obtainable from commercial sources, unless otherwise noted.

The further aspects, advantages, and embodiments of the invention are described in more detail below. The patents, published applications, and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter. As used herein, the following terms have the meanings indicated. As used in this specification, the singular forms "a," "an" and "the" specifically also encompass the plural forms of the terms to which they refer, unless the content clearly dictates otherwise. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%. "Antibody" or "antibodies" refers to all types of immunoglobulins, including IgG, IgM, IgA, IgD, and IgE, including $F_{ab}$ or antigen-recognition fragments thereof, including chimeric, polyclonal, and monoclonal antibodies. Peptide antigens suitable for producing antibodies of the invention may be designed, constructed and employed in accordance with well-known techniques. See, e.g., ANTIBODIES: A LABORATORY MANUAL, Chapter 5, p. 75-76, Harlow & Lane Eds., Cold Spring Harbor Laboratory (1988); Czernik, *Methods In Enzymology,* 201: 264-283 (1991); Merrifield, *J. Am. Chem. Soc.* 85: 21-49 (1962)). Also within the invention are antibody molecules with fewer than 4 chains, including single chain antibodies, Camelid antibodies and the like and components of the antibody, including a heavy chain or a light chain. In some embodiments an immunoglobulin chain may comprise in order from 5' to 3', a variable region and a constant region. The variable region may comprise three complementarity determining regions (CDRs), with interspersed framework (FR) regions for a structure FR1, CDR1, FR2, CDR2, FR3, CDR3 and FR4. Also within the invention are heavy or light chain variable regions, framework regions and CDRs. An antibody of the invention may comprise a heavy chain constant region that comprises some or all of a CH1 region, hinge, CH2 and CH3 region. An antibody of the invention may have an binding affinity ($K_D$) of $1\times10^{-7}$M or less. In other embodiments, the antibody binds with a $K_D$ of $1\times10^{-8}$ M, $1\times10^{-9}$ M, $1\times10^{10}$ M, $1\times10^{-11}$ M, $1\times10^{-12}$M or less. In certain embodiments, the $K_D$ is 1 pM to 500 pM, between 500 pM to 1 μM, between 1 μM to 100 nM, or between 100 mM to 10 nM. Antibodies of the invention can be derived from any species of animal, preferably a mammal. Non-limiting exemplary natural antibodies include antibodies derived from human, chicken, goats, and rodents (e.g., rats, mice, hamsters and rabbits), including transgenic rodents genetically engineered to produce human antibodies (see, e.g., Lonberg et al., WO93/12227; U.S. Pat. No. 5,545,806; and Kucherlapati, et al., WO91/10741; U.S. Pat. No. 6,150,584, which are herein incorporated by reference in their entirety). Natural antibodies are the antibodies produced by a host animal, however the invention contemplates also genetically altered antibodies wherein the amino acid sequence has been varied from that of a native antibody. Because of the relevance of recombinant DNA techniques to this application, one need not be confined to the sequences of amino acids found in natural antibodies; antibodies can be redesigned to obtain desired characteristics. The possible variations are many and range from the changing of just one or a few amino acids to the complete redesign of, for example, the variable or constant region. Changes in the constant region will, in general, be made in order to improve or alter characteristics, such as complement fixation, interaction with membranes and other effector functions. Changes in the variable region will be made in order to improve the antigen binding characteristics. The term "humanized antibody", as used herein, refers to antibody molecules in which amino acids have been replaced in the non-antigen binding regions in order to more closely resemble a human antibody, while still retaining the original binding ability. Other antibodies specifically contemplated are oligoclonal antibodies. As used herein, the phrase "oligoclonal antibodies" refers to a predetermined mixture of distinct monoclonal antibodies. See, e.g., PCT publication WO 95/20401; U.S. Pat. Nos. 5,789,208 and 6,335,163. In one embodiment, oligoclonal antibodies consisting of a predetermined mixture of antibodies against one or more epitopes are generated in a single cell. In other embodiments, oligoclonal antibodies comprise a plurality of heavy chains capable of pairing with a common light chain to generate antibodies with multiple specificities (e.g., PCT publication WO 04/009618). Oligoclonal antibodies are particularly useful when it is desired to target multiple epitopes on a single target molecule. In view of the assays and epitopes disclosed herein, those skilled in the art can generate or select antibodies or mixtures of antibodies that are applicable for an intended purpose and desired need. Recombinant antibodies against the phosphorylation sites identified in the invention are also included in the present application. These recombinant antibodies have the same amino acid sequence as the natural antibodies or have altered amino acid sequences of the natural antibodies in the present application. They can be made in any expression systems including both prokaryotic and eukaryotic expression systems or using phage display methods (see, e.g., Dower et al., WO91/17271 and McCafferty et al., WO92/01047; U.S. Pat. No. 5,969,108, which are herein incorporated by reference in their entirety). Antibodies can be engineered in numerous ways. They can be made as single-chain antibodies (including small modular immunopharmaceuticals or SMIPs™), Fab and $F(ab')_2$ fragments, etc. Antibodies can be humanized, chimerized, deimmunized, or fully human. Numerous publications set forth the many types of antibodies and the methods of engineering such antibodies. For example, see U.S. Pat. Nos. 6,355,245; 6,180,370; 5,693,762; 6,407,213; 6,548,640; 5,565,332; 5,225,539; 6,103,889; and 5,260,203. The genetically altered antibodies should be functionally equivalent to the above-mentioned natural antibodies. In certain embodiments, modified antibodies provide improved stability or/and therapeutic efficacy. Examples of modified antibodies include those with conservative substitutions of amino acid residues, and one or more deletions or additions of amino acids that do not significantly deleteriously alter the antigen binding utility. Substitutions can range from changing or modifying one or more amino acid residues to complete redesign of a region as long as the therapeutic utility is maintained. Antibodies of this application can be modified post-translationally (e.g., acetylation, and/or phosphorylation) or can be modified synthetically (e.g., the attachment of a labeling group). Antibodies with engineered or variant constant or Fc regions can be useful in modulating effector functions, such as, for example, antigen-dependent cytotoxicity (ADCC) and complement-dependent cytotoxicity (CDC). Such antibodies with engineered or variant constant or Fc regions may be useful in instances where a parent singling protein (Table 1) is expressed in normal tissue; variant antibodies without effector function in these instances may elicit the desired therapeutic response while not damaging normal tissue. Accordingly, certain aspects and methods of the present disclosure relate to antibodies with altered effector functions that comprise one or more amino acid substitutions, insertions, and/or deletions. The term "biologically active" refers to a protein having structural, regulatory, or biochemical functions of a naturally occurring molecule. Likewise, "immunologically active" refers to the capability of the natural, recombinant, or synthetic CD74-ROS fusion polypeptide or truncated ROS polypeptide, or any oligopeptide thereof, to induce a specific immune response in appropriate animals or cells and to bind with specific antibodies.

The term "biological sample" is used in its broadest sense, and means any biological sample suspected of containing CD74-ROS fusion or truncated ROS polynucleotides or polypeptides or fragments thereof, and may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells, blood, urine, marrow, or a tissue, and the like.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of recombinant DNA technology include Sambrook et al., Molecular Cloning: A Laboratory Manual, 2nd Ed., Cold Spring Harbor Laboratory Press, New York (1989); Kaufman et al., Eds., Handbook of Molecular and Cellular Methods in Biology in Medicine, CRC Press, Boca Raton (1995); McPherson, Ed., Directed Mutagenesis: A Practical Approach, IRL Press, Oxford (1991). Standard reference works setting forth the general principles of pharmacology include Goodman and Gilman's The Pharmacological Basis of Therapeutics, 11th Ed., McGraw Hill Companies Inc., New York (2006).

"Characterized by" with respect to a cancer and mutant ROS polynucleotide or polypeptide is meant a cancer in which the CD74-ROS gene translocation and/or expressed fusion polypeptide are present, as compared to a cancer in which such translocation and/or fusion polypeptide are not present. The presence of such fusion polypeptide may drive, in whole or in part, the growth and survival of such cancer.

"Consensus" refers to a nucleic acid sequence which has been re-sequenced to resolve uncalled bases, or which has been extended using XL-PCR™ (Perkin Elmer, Norwalk, Conn.) in the 5' and/or the 3' direction and re-sequenced, or which has been assembled from the overlapping sequences of more than one Incyte clone using the GELVIEW™ Fragment Assembly system (GCG, Madison, Wis.), or which has been both extended and assembled.

"ROS kinase-inhibiting therapeutic" means any composition comprising one or more compounds, chemical or biological, which inhibits, either directly or indirectly, the expression and/or activity of wild type or truncated ROS, either alone and/or as part of the CD74-ROS fusion proteins.

"Derivative" refers to the chemical modification of a nucleic acid sequence encoding CD74-ROS fusion polypeptide or the encoded polypeptide itself. Illustrative of such modifications would be replacement of hydrogen by an alkyl, acyl, or amino group. A nucleic acid derivative would encode a polypeptide that retains essential biological characteristics of the natural molecule.

"Detectable label" with respect to a polypeptide, polynucleotide, or reagent disclosed herein means a chemical, biological, or other modification, including but not limited to fluorescence, mass, residue, dye, radioisotope, label, or tag modifications, etc., by which the presence of the molecule of interest may be detected.

"Expression" or "expressed" with respect to CD74-ROS fusion polypeptide in a biological sample means significantly expressed as compared to control sample in which this fusion polypeptide is not significantly expressed.

"Heavy-isotope labeled peptide" (used interchangeably with AQUA peptide) means a peptide comprising at least one heavy-isotope label, which is suitable for absolute quantification or detection of a protein as described in WO/03016861, "Absolute Quantification of Proteins and Modified Forms Thereof by Multistage Mass Spectrometry" (Gygi et al.), further discussed below. The term "specifically detects" with respect to such an AQUA peptide means the peptide will only detect and quantify polypeptides and proteins that contain the AQUA peptide sequence and will not substantially detect polypeptides and proteins that do not contain the AQUA peptide sequence.

"Isolated" (or "substantially purified") refers to nucleic or amino acid sequences that are removed from their natural environment, isolated or separated. They preferably are at least 60% free, more preferably 75% free, and most preferably 90% or more free from other components with which they are naturally associated.

"Mimetic" refers to a molecule, the structure of which is developed from knowledge of the structure of CD74-ROS fusion polypeptide or portions thereof and, as such, is able to effect some or all of the actions of translocation associated protein-like molecules.

"Mutant ROS" polynucleotide or polypeptide means a CD74-ROS fusion polynucleotide or polypeptide as described herein.

"Polynucleotide" (or "nucleotide sequence") refers to an oligonucleotide, nucleotide, or polynucleotide, and fragments or portions thereof, and to DNA or RNA of genomic or synthetic origin, which may be single- or double-stranded, and represent the sense or anti-sense strand.

"Polypeptide" (or "amino acid sequence") refers to an oligopeptide, peptide, polypeptide, or protein sequence, and fragments or portions thereof, and to naturally occurring or synthetic molecules. Where "amino acid sequence" is recited herein to refer to an amino acid sequence of a naturally occurring protein molecule, "amino acid sequence" and like terms, such as "polypeptide" or "protein", are not meant to limit the amino acid sequence to the complete, native amino acid sequence associated with the recited protein molecule.

"CD74-ROS fusion polynucleotide" refers to the nucleic acid sequence of a substantially purified CD74-ROS translocation gene product or fusion polynucleotide as described herein, obtained from any species, particularly mammalian, including bovine, ovine, porcine, murine, equine, and preferably human, from any source whether natural, synthetic, semi-synthetic, or recombinant.

"CD74-ROS fusion polypeptide" refers to the amino acid sequence of a substantially purified CD74-ROS fusion polypeptide described herein, obtained from any species, particularly mammalian, including bovine, ovine, porcine, murine, equine, and preferably human, from any source whether natural, synthetic, semi-synthetic, or recombinant.

The terms "specifically binds to" (or "specifically binding" or "specific binding") in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. The term "does not bind" with respect to an antibody's binding to sequences or antigenic determinants other than that for which it is specific means does not substantially react with as compared to the antibody's binding to antigenic determinant or sequence for which the antibody is specific.

The term "stringent conditions" with respect to sequence or probe hybridization conditions is the "stringency" that occurs within a range from about $T_m$ minus 5° C. (5° C. below the melting temperature ($T_m$) of the probe or sequence) to about 20° C. to 25° C. below $T_m$. Typical stringent conditions are: overnight incubation at 42° C. in a solution comprising: 50% formamide, 5×.SSC (750 mM NaCl, 75 mM trisodium citrate), 50 mM sodium phosphate (pH 7.6), 5× Denhardt's solution, 10% dextran sulfate, and 20 micrograms/ml denatured, sheared salmon sperm DNA, followed by washing the filters in 0.1×SSC at about 65° C. As will be understood by those of skill in the art, the stringency of hybridization may be altered in order to identify or detect identical or related polynucleotide sequences.

A "variant" of CD74-ROS fusion polypeptide refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A. Identification Mutant ROS Kinase in Human NSCLC.

The novel human gene translocation disclosed herein, which occurs between chromosome (5q32) and chromosome (6q22) in human NSCLC and results in expression of two variant fusion proteins that combine the N-terminus (exons 1-6) of CD74 with the transmembrane and kinase domains (exons 34-43) of ROS, was surprisingly identified during examination of global phosphorylated peptide profiles in extracts from a human non-small cell lung carcinoma (NSCLC) patient, a subtype of lung cancers. The chromosomes, genes, and product involved in this translocation are shown in FIG. 1.

Figure 5:
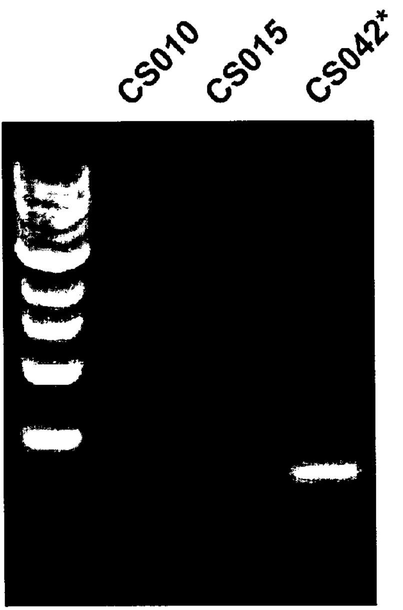
FIG. 5—is the gel depicting the detection of the fusion gene formed by the CD74 and ROS translocation by RT-PCR; with primer sequences shown for CD74-F1 (top) and ROS-GSP3 (bottom) (SEQ ID NOs: 9 and 10, respectively).
Figure 6:
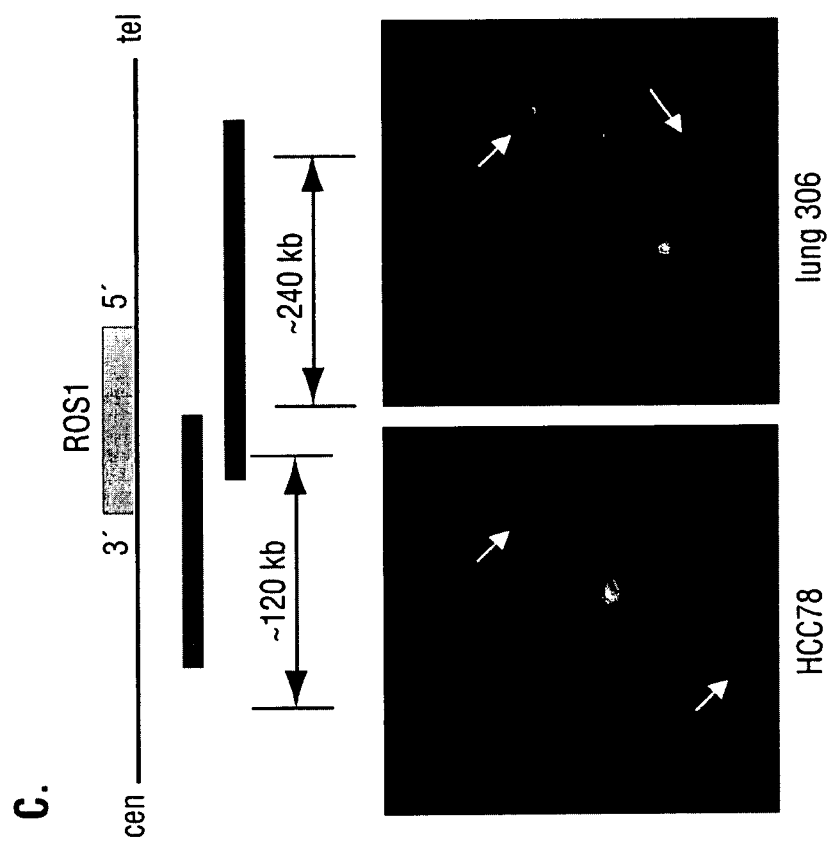
FIG. 6—is an image showing specific detection of the ROS fusion/translocation (in a human NSCLC cell line and patient) by FISH using a 2-color break-a-part probe

The phosphorylation profile of this cell line was elucidated using a recently described technique for the isolation and mass spectrometric characterization of modified peptides from complex mixtures (see U.S. Patent Publication No. 20030044848, Rush et al., "Immunoaffinity Isolation of Modified Peptides from Complex Mixtures" (the "IAP" technique), as further described in Example 1 herein. Application of the IAP technique using a phosphotyrosine-specific antibody (Cell Signaling Technology, Inc., Beverly, Mass., 2003/04 Cat. #9411), identified that the a NSCLC patient expresses ROS kinase (in contrast to most of the other NSCLC patients, which do not). The screen identified many other activated kinases in this patient including ROS. Analysis of the sequence 5' to ROS by 5' RACE then identified that the kinase was fused to the N-terminus of CD74 (see FIG. 5).

As shown in panel B of FIG. 1, the CD74-ROS translocation combines the N-terminus of CD74 (amino acids 1-208) with the transmembrane and kinase domains of ROS (amino acids 1853-2347) (see also SEQ ID NOs:1), to produce a fusion (see panel C of FIG. 1). The translocation retains the 5'-most transmembrane domain of CD74. The resulting CD74-ROS fusion proteins, which comprise 703 amino acids, (see panel C of FIG. 1 and FIG. 2 (SEQ ID NOs: 1) and are expected to retain kinase activity of ROS.

Global phosphopeptide profiling and FISH analysis of human NSCLC tumors indicate that a small percentage of patients do in fact harbor this mutation (see Examples 1 and 3), and these patients may benefit from ROS inhibitor therapy.

B. Isolated Polynucleotides.

The present invention provides, in part, isolated polynucleotides that encode CD74-ROS fusion polypeptides, nucleotide probes that hybridize to such polynucleotides, and methods, vectors, and host cells for utilizing such polynucleotides to produce recombinant fusion polypeptides. Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were determined using an automated peptide sequencer. As is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion. Unless otherwise indicated, each nucleotide sequence set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U). For instance, reference to an RNA molecule having the sequence of SEQ ID NOs: 2 or set forth using deoxyribonucleotide abbreviations is intended to indicate an RNA molecule having a sequence in which each deoxyribonucleotide A, G or C of SEQ ID NOs: 2 has been replaced by the corresponding ribonucleotide A, G or C, and each deoxyribonucleotide T has been replaced by a ribonucleotide U.

In one embodiment, the invention provides an isolated polynucleotide comprising a nucleotide sequence at least 95% identical to a sequence selected from the group consisting of: (a) a nucleotide sequence encoding a CD74-ROS fusion polypeptide comprising the amino acid sequence of SEQ ID NO: 1; (b) a nucleotide sequence encoding a CD74-ROS fusion polypeptide comprising the N-terminal amino acid sequence of CD74 (residues 1-208 of SEQ ID NO: 3) and the kinase domain of ROS (residues 1945-2222 of SEQ ID NO: 5); (c) a nucleotide sequence comprising the N-terminal nucleotide sequence of CD74 (residues 1-624 of SEQ ID NO: 4) and the kinase domain nucleotide sequence of ROS (residues 6032-6865 of SEQ ID NO: 6); (d) a nucleotide sequence comprising at least six contiguous nucleotides encompassing the fusion junction (residues 622-627 of SEQ ID NO: 2) of a CD74-ROS fusion polynucleotide; (e) a nucleotide sequence encoding a polypeptide comprising at least six contiguous amino acids encompassing the fusion junction (residues 208-209 of SEQ ID NO: 1 of a CD74-ROS fusion polypeptide; and (f) a nucleotide sequence complementary to any of the nucleotide sequences of (a)-(e).

Using the information provided herein, such as the nucleotide sequences in FIG. 2 (SEQ ID NOs: 2), a nucleic acid molecule of the present invention encoding a mutant ROS polypeptide of the invention may be obtained using standard cloning and screening procedures, such as those for cloning cDNAs using mRNA as starting material. The fusion gene can also be identified in cDNA libraries in other lung carcinomas or cancers in which the CD74-ROS translocation (5q32, 6q22) occurs, or in which a deletion or alternative translocation results in expression of a truncated ROS kinase lacking the extracellular domain of the wild type kinase.

The determined nucleotide sequence of the CD74-ROS translocation gene products (SEQ ID NO: 2) encode kinase fusion protein 703 amino acids (see FIG. 2 (SEQ ID NO: 1) and FIG. 1). The CD74-ROS fusion polynucleotides comprise the portion of the nucleotide sequence of wild type CD74 (see FIG. 3 (SEQ ID NO: 3) that encodes the N-terminus of that protein (exons 1-6) with the portion of the nucleotide sequence of wild type ROS (see FIG. 4 (SEQ ID NO: 5) that encodes the transmembrane and kinase domains of that protein (exons 34-43). See FIG. 1.

As indicated, the present invention provides, in part, the mature form of the CD74-ROS fusion proteins. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide. Therefore, the present invention provides, in part, nucleotide sequences encoding a mature CD74-ROS fusion polypeptide having the amino acid sequence encoded by the cDNA clone, which was deposited with the American Type Culture Collection (Manassas, Va., U.S.A.) on Sep. 20, 2006 in accordance with the provisions of the Budapest Treaty.

By the mature CD74-ROS polypeptide having the amino acid sequence encoded by the deposited cDNA clone is meant the mature form of this fusion protein produced by expression in a mammalian cell (e.g., COS cells, as described below) of the complete open reading frame encoded by the human DNA sequence of the clone contained in the vector in the deposited host cell.

As indicated, polynucleotides of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

Isolated polynucleotides of the invention are nucleic acid molecules, DNA or RNA, which have been removed from their native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated polynucleotides of the invention include the DNA molecules shown in FIG. 2 (SEQ ID NOs: 2), DNA molecules comprising the coding sequence for the mature CD74-ROS fusion proteins shown in FIG. 1 (SEQ ID NOs: 1), and DNA molecules that comprise a sequence substantially different from those described above but which, due to the degeneracy of the genetic code, still a mutant ROS polypeptide of the invention. The genetic code is well known in the art, thus, it would be routine for one skilled in the art to generate such degenerate variants.

In another embodiment, the invention provides an isolated polynucleotide encoding the CD74-ROS fusion polypeptide comprising the CD74-ROS translocation nucleotide sequence contained in the above-described deposited cDNA clone. Preferably, such nucleic acid molecule will encode the mature fusion polypeptide encoded by the deposited cDNA clone. In another embodiment, the invention provides an isolated nucleotide sequence encoding a CD74-ROS fusion polypeptide comprising the N-terminal amino acid sequence of CD74 (residues 1-208 of SEQ ID NO: 3) and the kinase domain of ROS (residues 1945-2222 of SEQ ID NO: 5). In one embodiment, the polypeptide comprising the kinase domain of ROS comprises residues 1853-2347 of SEQ ID NO: 5 (see FIG. 1, panel B). In another embodiment, the aforementioned N-terminal amino acid sequence of CD74 and kinase domain of ROS are encoded by nucleotide sequences comprising nucleotides 1-624 of SEQ ID NO: 4 and nucleotides 6032-6865 of SEQ ID NO: 6, respectively.

The invention further provides isolated polynucleotides comprising nucleotide sequences having a sequence complementary to one of the mutant ROS fusion polypeptides of the invention. Such isolated molecules, particularly DNA molecules, are useful as probes for gene mapping, by in situ hybridization with chromosomes, and for detecting expression of the CD74-ROS fusion protein or truncated ROS kinase polypeptide in human tissue, for instance, by Northern blot analysis.

The present invention is further directed to fragments of the isolated nucleic acid molecules described herein. By a fragment of an isolated CD74-ROS polynucleotide or truncated ROS polynucleotide of the invention is intended fragments at least about 15 nucleotides, and more preferably at least about 20 nucleotides, still more preferably at least about 30 nucleotides, and even more preferably, at least about 40 nucleotides in length, which are useful as diagnostic probes and primers as discussed herein. Of course, larger fragments of about 50-1500 nucleotides in length are also useful according to the present invention, as are fragments corresponding to most, if not all, of the CD74-ROS nucleotide sequence of the deposited cDNA or as shown in FIG. 2 (SEQ ID NOs: 2). By a fragment at least 20 nucleotides in length, for example, is intended fragments that include 20 or more contiguous bases from the respective nucleotide sequences from which the fragments are derived.

Generation of such DNA fragments is routine to the skilled artisan, and may be accomplished, by way of example, by restriction endonuclease cleavage or shearing by sonication of DNA obtainable from the deposited cDNA clone or synthesized according to the sequence disclosed herein. Alternatively, such fragments can be directly generated synthetically.

Preferred nucleic acid fragments or probes of the present invention include nucleic acid molecules encoding the fusion junction of the CD74-ROS translocation gene products (see FIG. 1, panels B and C). For example, in certain preferred embodiments, an isolated polynucleotide of the invention comprises a nucleotide sequence/fragment comprising at least six contiguous nucleotides encompassing the fusion junction (residues 622-627 of SEQ ID NO: 2) of a CD74-ROS fusion polynucleotide. In another preferred embodiment, an isolated polynucleotide of the invention comprises a nucleotide sequence/fragment that encodes a polypeptide comprising at least six contiguous amino acids encompassing the fusion junction (residues 208-209 of SEQ ID NO: 1) of a CD74-ROS fusion polypeptide.

In another aspect, the invention provides an isolated polynucleotide that hybridizes under stringent hybridization conditions to a portion of an mutant ROS kinase polynucleotide of the invention as described herein. By "stringent hybridization conditions" is intended overnight incubation at 42° C. in a solution comprising: 50% formamide, 5×.SSC (750 mM NaCl, 75 mM trisodium citrate), 50 mM sodium phosphate (pH 7.6), 5× Denhardt's solution, 10% dextran sulfate, and 20 micrograms/ml denatured, sheared salmon sperm DNA, followed by washing the filters in 0.1×SSC at about 65° C.

By a polynucleotide that hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30-70 nt of the reference polynucleotide. These are useful as diagnostic probes and primers (e.g. for PCR) as discussed above and in more detail below.

Of course, polynucleotides hybridizing to a larger portion of the reference polynucleotide (e.g. the mature CD74-ROS fusion polynucleotides described in FIG. 2 (SEQ ID NOs: 2), for instance, a portion 50-750 nt in length, or even to the entire length of the reference polynucleotide, are also useful as probes according to the present invention, as are polynucleotides corresponding to most, if not all, of the nucleotide sequence of the deposited cDNA or the nucleotide sequences shown in FIG. 2 (SEQ ID NOs: 2).

By a portion of a polynucleotide of "at least 20 nucleotides in length," for example, is intended 20 or more contiguous nucleotides from the nucleotide sequence of the reference polynucleotide. As indicated, such portions are useful diagnostically either as a probe according to conventional DNA hybridization techniques or as primers for amplification of a target sequence by the polymerase chain reaction (PCR), as described, for instance, in MOLECULAR CLONING, A LABORATORY MANUAL, 2nd. edition, Sambrook, J., Fritsch, E. F. and Maniatis, T., eds., Cold Spring Harbor Laboratory Press, Cold Spring Harbor, N.Y. (1989), the entire disclosure of which is hereby incorporated herein by reference. Of course, a polynucleotide which hybridizes only to a poly A sequence (such as the 3' terminal poly(A) tract of the CD74-ROS sequences shown in FIG. 2 (SEQ ID NOs: 2) or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention, which encode a mutant ROS kinase polypeptide of the invention, may include but are not limited to those encoding the amino acid sequence of the mature polypeptide, by itself; the coding sequence for the mature polypeptide and additional sequences, such as those encoding the leader or secretory sequence, such as a pre-, or pro- or pre-pro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities.

Thus, the sequence encoding the polypeptide may be fused to a marker sequence, such as a sequence encoding a peptide that facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al., *Proc. Natl. Acad. Sci. USA* 86: 821-824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37: 767 (1984). As discussed below, other such fusion proteins include the CD74-ROS fusion polypeptide itself fused to Fc at the N- or C-terminus.

The present invention further relates to variants of the nucleic acid molecules of the present invention, which encode portions, analogs or derivatives of a CD74-ROS fusion polypeptide or truncated ROS kinase polypeptide disclosed herein. Variants may occur naturally, such as a natural allelic variant. By an "allelic variant" is intended one of several alternate forms of a gene occupying a given locus on a chromosome of an organism. See, e.g. GENES H, Lewin, B., ed., John Wiley & Sons, New York (1985). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities (e.g. kinase activity) of the mutant ROS kinase polypeptides disclosed herein. Also especially preferred in this regard are conservative substitutions.

Further embodiments of the invention include isolated polynucleotides comprising a nucleotide sequence at least 90% identical. In some embodiments of the invention the nucleotide is at least 95%, 96%, 97%, 98% or 99% identical, to a mutant ROS polynucleotide of the invention (for example, a nucleotide sequence encoding the RB-ROS fusion polypeptide having the complete amino acid sequence shown in FIG. 2 (SEQ ID NOs: 1; or a nucleotide sequence encoding the N-terminal of CD74 and the kinase domain of ROS (see FIG. 1, panel B; and FIGS. 3 and 4); or a nucleotide complementary to such exemplary sequences).

By a polynucleotide having a nucleotide sequence at least, for example, 95% "identical" to a reference nucleotide sequence encoding a mutant ROS kinase polypeptide is intended that the nucleotide sequence of the polynucleotide is identical to the reference sequence except that the polynucleotide sequence may include up to five point mutations per each 100 nucleotides of the reference nucleotide sequence encoding the mutant ROS polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5" terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequences shown in FIG. 2 (SEQ ID NOs: 2) or to the nucleotide sequence of the deposited cDNA clone described above can be determined conventionally using known computer programs such as the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman, *Advances in Applied Mathematics* 2: 482-489 (1981), to find the best segment of homology between two sequences. When using Bestfit or any other sequence alignment program to determine whether a particular sequence is, for instance, 95% identical to a reference CD74-ROS fusion polynucleotide sequence according to the present invention, the parameters are set, of course, such that the percentage of identity is calculated over the full length of the reference nucleotide sequence and that gaps in homology of up to 5% of the total number of nucleotides in the reference sequence are allowed.

The present invention includes in its scope nucleic acid molecules at least 90%, 95%, 96%, 97%, 98% or 99% identical to the nucleic acid sequences shown in FIG. 2 (SEQ ID NOs: 2), or to nucleotides 625-2172 of SEQ ID NO: 2, or to the nucleic acid sequence of the deposited cDNA, irrespective of whether they encode a polypeptide having ROS kinase activity. This is because even where a particular nucleic acid molecule does not encode a fusion polypeptide having ROS kinase activity, one of skill in the art would still know how to use the nucleic acid molecule, for instance, as a hybridization probe or a polymerase chain reaction (PCR) primer. Uses of the nucleic acid molecules of the present invention that do not encode a polypeptide having kinase include, inter alia, (1) isolating the CD74-ROS translocation gene or allelic variants thereof in a cDNA library; (2) in situ hybridization (e.g., "FISH") to metaphase chromosomal spreads to provide precise chromosomal location of the CD74-ROS translocation gene, as described in Verma et al., Human Chromosomes: A Manual of Basic Techniques, Pergamon Press, New York (1988); and Northern Blot analysis for detecting CD74-ROS fusion protein mRNA expression in specific tissues.

Within the invention are also nucleic acid molecules having sequences at least 95% identical to a mutant ROS kinase polypeptide of the invention or to the nucleic acid sequence of the deposited cDNA, which do, in fact, encode a fusion polypeptide having ROS kinase activity. Such activity may be similar, but not necessarily identical, to the activity of the CD74-ROS fusion protein disclosed herein (either the full-length protein, the mature protein, or a protein fragment that retains kinase activity), as measured in a particular biological assay. For example, the kinase activity of ROS can be examined by determining its ability to phosphorylate one or more tyrosine containing peptide substrates, for example, "Src-related peptide" (RRLIEDAEYAARG), which is a substrate for many receptor and nonreceptor tyrosine kinases.

Due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA or the nucleic acid sequence shown in FIG. 2 (SEQ ID NOs: 2) will encode a fusion polypeptide having ROS kinase activity. In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide that retains ROS kinase activity. This is because the skilled artisan is fully aware of amino acid substitutions that are either less likely or not likely to significantly effect protein function (e.g., replacing one aliphatic amino acid with a second aliphatic amino acid). For example, guidance concerning how to make phenotypically silent amino acid substitutions is provided in Bowie et al., "Deciphering the Message in Protein Sequences: Tolerance to Amino Acid Substitutions," *Science* 247: 1306-1310 (1990), which describes two main approaches for studying the tolerance of an amino acid sequence to change. Skilled artisans familiar with such techniques also appreciate which amino acid changes are likely to be permissive at a certain position of the protein. For example, most buried amino acid residues require nonpolar side chains, whereas few features of surface side chains are generally conserved. Other such phenotypically silent substitutions are described in Bowie et al., supra., and the references cited therein.

Methods for DNA sequencing that are well known and generally available in the art may be used to practice any polynucleotide embodiments of the invention. The methods may employ such enzymes as the Klenow fragment of DNA polymerase I, SEQUENASE® (US Biochemical Corp, Cleveland, Ohio), Taq polymerase (Perkin Elmer), thermostable T7 polymerase (Amersham, Chicago, Ill.), or combinations of recombinant polymerases and proofreading exonucleases such as the ELONGASE Amplification System marketed by Gibco BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI 377 DNA sequencers (Perkin Elmer).

Polynucleotide sequences encoding a mutant ROS polypeptide of the invention may be extended utilizing a partial nucleotide sequence and employing various methods known in the art to detect upstream sequences such as promoters and regulatory elements. For example, one method that may be employed, "restriction-site" PCR, uses universal primers to retrieve unknown sequence adjacent to a known locus (Sarkar, G., *PCR Methods Applic.* 2: 318-322 (1993)). In particular, genomic DNA is first amplified in the presence of primer to linker sequence and a primer specific to the known region. Exemplary primers are those described in Example 4 herein. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia et al., *Nucleic Acids Res.* 16: 8186 (1988)). The primers may be designed using OLIGO 4.06 Primer Analysis software (National Biosciences Inc., Plymouth, Minn.), or another appropriate program, to be 22-30 nucleotides in length, to have a GC content of 50% or more, and to anneal to the target sequence at temperatures about 68-72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom et al., *PCR Methods Applic.* 1: 111-119 (1991)). In this method, multiple restriction enzyme digestions and ligations may also be used to place an engineered double-stranded sequence into an unknown portion of the DNA molecule before performing PCR. Another method which may be used to retrieve unknown sequences is that described in Parker et al., *Nucleic Acids Res.* 19: 3055-3060 (1991)). Additionally, one may use PCR, nested primers, and PROMOTERFINDER® libraries to walk in genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences that contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions.

Capillary electrophoresis systems, which are commercially available, may be used to analyze the size or confirm the nucleotide sequence of sequencing or PCR products. In particular, capillary sequencing may employ flowable polymers for electrophoretic separation, four different fluorescent dyes (one for each nucleotide) that are laser activated, and detection of the emitted wavelengths by a charge coupled device camera. Output/light intensity may be converted to electrical signal using appropriate software (e.g. GENOTYPER™ and SEQUENCE NAVIGATOR™, Perkin Elmer) and the entire process from loading of samples to computer analysis and electronic data display may be computer controlled. Capillary electrophoresis is especially preferable for the sequencing of small pieces of DNA that might be present in limited amounts in a particular sample.

C. Vectors and Host Cells.

The present invention also provides recombinant vectors that comprise an isolated polynucleotide of the present invention, host cells which are genetically engineered with the recombinant vectors, and the production of recombinant CD74-ROS polypeptides or fragments thereof by recombinant techniques.

Recombinant constructs may be introduced into host cells using well-known techniques such infection, transduction, transfection, transvection, electroporation and transformation. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells. The invention may be practiced with vectors comprising cis-acting control regions to the polynucleotide of interest. Appropriate trans-acting factors may be supplied by the host, supplied by a complementing vector or supplied by the vector itself upon introduction into the host. In certain preferred embodiments in this regard, the vectors provide for specific expression, which may be inducible and/or cell type-specific (e.g., those inducible by environmental factors that are easy to manipulate, such as temperature and nutrient additives).

The DNA insert comprising a CD74-ROS polynucleotide or truncated ROS polynucleotide of the invention should be operatively linked to an appropriate promoter, such as the phage lambda PL promoter, the *E. coli* lac, trp and tac promoters, the SV40 early and late promoters and promoters of retroviral LTRs, to name a few. Other suitable promoters are known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells; insect cells such as *Drosophila* S2 and *Spodoptera* Sf9 cells; animal cells such as CHO, COS and Bowes melanoma cells; and plant cells. Appropriate culture mediums and conditions for the above-described host cells are known in the art.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Among known bacterial promoters suitable for use in the present invention include the *E. coli* lad and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

In the yeast, *Saccharomyces cerevisiae*, a number of vectors containing constitutive or inducible promoters such as alpha factor, alcohol oxidase, and PGH may be used. For reviews, see Ausubel et al. (1989) Current Protocols in Molecular Biology, John Wiley & Sons, New York, N.Y., and Grant et al., *Methods Enzymol.* 153: 516-544 (1997).

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., Basic Methods in Molecular Biology (1986).

Transcription of DNA encoding a CD74-ROS fusion polypeptide of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at basepairs 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein (e.g. a GST-fusion), and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins.

For example, EP-A-0 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL5—has been fused with Fc portions for the purpose of high-throughput screening assays to identify antagonists of hIL-5. See Bennett et al., *Journal of Molecular Recognition* 8: 52-58 (1995) and Johanson et al., *The Journal of Biological Chemistry* 270(16): 9459-9471 (1995).

CD74-ROS polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Accordingly, in one embodiment, the invention provides a method for producing a recombinant CD74-ROS fusion polypeptide by culturing a recombinant host cell (as described above) under conditions suitable for the expression of the fusion polypeptide and recovering the polypeptide. Culture conditions suitable for the growth of host cells and the expression of recombinant polypeptides from such cells are well known to those of skill in the art. See, e.g., Current Protocols in Molecular Biology, Ausubel F M et al., eds., Volume 2, Chapter 16, Wiley Interscience.

D. Isolated Polypeptides.

The invention also provides, in part, isolated CD74-ROS fusion polypeptides and fragments thereof. In one embodiment, the invention provides an isolated polypeptide comprising an amino acid sequence at least 95% identical to a sequence selected from the group consisting of: (a) an amino acid sequence encoding a CD74-ROS fusion polypeptide comprising the amino acid sequence of SEQ ID NO: 1; (b) an amino acid sequence encoding a CD74-ROS fusion polypeptide comprising the N-terminal amino acid sequence of CD74 (residues 1-208 of SEQ ID NO: 3) and the kinase domain of ROS (residues 1945-2222 of SEQ ID NO: 5); and (c) an amino acid sequence encoding a polypeptide comprising at least six contiguous amino acids encompassing the fusion junction (residues 208-209 of SEQ ID NO: 1 or residues 208-209 of SEQ ID NO: 3) of a CD74-ROS fusion polypeptide;

In one preferred embodiment, the invention provides an isolated CD74-ROS fusion polypeptide having the amino acid sequence encoded by the deposited cDNA described above. In another preferred embodiment, recombinant mutant polypeptides of the invention are provided, which may be produced using a recombinant vector or recombinant host cell as described above.

It will be recognized in the art that some amino acid sequences of a CD74-ROS fusion polypeptide can be varied without significant effect of the structure or function of the mutant protein. If such differences in sequence are contemplated, it should be remembered that there will be critical areas on the protein which determine activity (e.g. the kinase domain of ROS). In general, it is possible to replace residues that form the tertiary structure, provided that residues performing a similar function are used. In other instances, the type of residue may be completely unimportant if the alteration occurs at a non-critical region of the protein.

Thus, the invention further includes variations of a CD74-ROS fusion polypeptide that show substantial ROS kinase activity or that include regions of CD74 and ROS proteins, such as the protein portions discussed below. Such mutants include deletions, insertions, inversions, repeats, and type substitutions (for example, substituting one hydrophilic residue for another, but not strongly hydrophilic for strongly hydrophobic as a rule). Small changes or such "neutral" amino acid substitutions will generally have little effect on activity.

Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Examples of conservative amino acid substitutions known to those skilled in the art are: Aromatic: phenylalanine tryptophan tyrosine; Hydrophobic: leucine isoleucine valine; Polar: glutamine asparagines; Basic: arginine lysine histidine; Acidic: aspartic acid glutamic acid; Small: alanine serine threonine methionine glycine. As indicated in detail above, further guidance concerning which amino acid changes are likely to be phenotypically silent (i.e., are not likely to have a significant deleterious effect on a function) can be found in Bowie et al., Science 247, supra.

The polypeptides of the present invention are preferably provided in an isolated form, and preferably are substantially purified. A recombinantly produced version of a CD74-ROS fusion polypeptide of the invention can be substantially purified by the one-step method described in Smith and Johnson, *Gene* 67: 31-40 (1988).

The polypeptides of the present invention include the CD74-ROS fusion polypeptides of FIG. 2 (SEQ ID NOs: 1) (whether or not including a leader sequence), the fusion polypeptide encoded by the deposited cDNA clone, an amino acid sequence encoding a CD74-ROS fusion polypeptide comprising the N-terminal amino acid sequence of CD74 (residues 1-208 of SEQ ID NO: 5) and the kinase domain of ROS (residues 1945-2222 of SEQ ID NO: 7), and an amino acid sequence encoding a polypeptide comprising at least six contiguous amino acids encompassing the fusion junction (residues 208-209 of SEQ ID NO: 1) of a CD74-ROS fusion polypeptide, as well as polypeptides that have at least 90% similarity, more preferably at least 95% similarity, and still more preferably at least 96%, 97%, 98% or 99% similarity to those described above.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (*Advances in Applied Mathematics* 2: 482-489 (1981)) to find the best segment of similarity between two sequences.

By a polypeptide having an amino acid sequence at least, for example, 95% "identical" to a reference amino acid sequence of a mutant ROS polypeptide of the invention is intended that the amino acid sequence of the polypeptide is identical to the reference sequence except that the polypeptide sequence may include up to five amino acid alterations per each 100 amino acids of the reference amino acid sequence of the CD74-ROS fusion polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

A CD74-ROS fusion polypeptide of the present invention could be used as a molecular weight marker on SDS-PAGE gels or on molecular sieve gel filtration columns, for example, using methods well known to those of skill in the art.

As further described in detail below, the polypeptides of the present invention can also be used to generate fusion polypeptide specific reagents, such as polyclonal and monoclonal antibodies, which are useful in assays for detecting mutant ROS polypeptide expression as described below or as agonists and antagonists capable of enhancing or inhibiting mutant ROS protein function/activity. Further, such polypeptides can be used in the yeast two-hybrid system to "capture" CD74-ROS fusion polypeptide binding proteins, which are also candidate agonist and antagonist according to the present invention. The yeast two hybrid system is described in Fields and Song, *Nature* 340: 245-246 (1989).

In another aspect, the invention provides a peptide or polypeptide comprising an epitope-bearing portion of a polypeptide of the invention, namely an epitope comprising the fusion junction of a CD74-ROS fusion polypeptide variant The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998-4002 (1983). The production of fusion polypeptide-specific antibodies of the invention is described in further detail below.

The antibodies raised by antigenic epitope-bearing peptides or polypeptides are useful to detect a mimicked protein, and antibodies to different peptides may be used for tracking the fate of various regions of a protein precursor which undergoes post-translational processing. The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, for instance, Wilson et al., *Cell* 37: 767-778 (1984) at 777. The anti-peptide antibodies of the invention also are useful for purification of the mimicked protein, for instance, by adsorption chromatography using methods well known in the art. Immunological assay formats are described in further detail below.

Recombinant mutant ROS kinase polypeptides are also within the scope of the present invention, and may be producing using fusion polynucleotides of the invention, as described in Section B above. For example, the invention provides a method for producing a recombinant CD74-ROS fusion polypeptide by culturing a recombinant host cell (as described above) under conditions suitable for the expression of the fusion polypeptide and recovering the polypeptide. Culture conditions suitable for the growth of host cells and the expression of recombinant polypeptides from such cells are well known to those of skill in the art.

E. Mutant-Specific Reagents

Mutant ROS polypeptide-specific reagents useful in the practice of the disclosed methods include, among others, fusion polypeptide specific antibodies and AQUA peptides (heavy-isotope labeled peptides) corresponding to, and suitable for detection and quantification of, CD74-ROS fusion polypeptide expression in a biological sample. A fusion polypeptide-specific reagent is any reagent, biological or chemical, capable of specifically binding to, detecting and/or quantifying the presence/level of expressed CD74-ROS fusion polypeptide in a biological sample. The term includes, but is not limited to, the preferred antibody and AQUA peptide reagents discussed below, and equivalent reagents are within the scope of the present invention.

Antibodies.

Reagents suitable for use in practice of the methods of the invention include a CD74-ROS fusion polypeptide-specific antibody. A fusion-specific antibody of the invention is an isolated antibody or antibodies that specifically bind(s) a CD74-ROS fusion polypeptide of the invention (e.g. SEQ ID NO: 1) but does not substantially bind either wild type CD74 or wild type ROS. Other suitable reagents include epitope-specific antibodies that specifically bind to an epitope in the extracelluar domain of wild type ROS protein sequence (which domain is not present in the truncated ROS kinase disclosed herein), and are therefore capable of detecting the presence (or absence) of wild type ROS in a sample.

Human CD74-ROS fusion polypeptide-specific antibodies may also bind to highly homologous and equivalent epitopic peptide sequences in other mammalian species, for example murine or rabbit, and vice versa. Antibodies useful in practicing the methods of the invention include (a) monoclonal antibodies, (b) purified polyclonal antibodies that specifically bind to the target polypeptide (e.g. the fusion junction of CD74-ROS fusion polypeptide, (c) antibodies as described in (a)-(b) above that bind equivalent and highly homologous epitopes or phosphorylation sites in other non-human species (e.g. mouse, rat), and (d) fragments of (a)-(c) above that bind to the antigen (or more preferably the epitope) bound by the exemplary antibodies disclosed herein.

The term “antibody” or “antibodies” as used herein refers to all types of immunoglobulins, including IgG, IgM, IgA, IgD, and IgE. The antibodies may be monoclonal or polyclonal and may be of any species of origin, including (for example) mouse, rat, rabbit, horse, or human, or may be chimeric antibodies. See, e.g., M. Walker et al., *Molec. Immunol.* 26: 403-11 (1989); Morrision et al., *Proc. Nat'l. Acad. Sci.* 81: 6851 (1984); Neuberger et al., *Nature* 312: 604 (1984)). The antibodies may be recombinant monoclonal antibodies produced according to the methods disclosed in U.S. Pat. No. 4,474,893 (Reading) or U.S. Pat. No. 4,816,567 (Cabilly et al.) The antibodies may also be chemically constructed specific antibodies made according to the method disclosed in U.S. Pat. No. 4,676,980 (Segel et al.)

The preferred epitopic site of a CD74-ROS fusion polypeptide specific antibody of the invention is a peptide fragment consisting essentially of about 11 to 17 amino acids of a human CD74-ROS fusion polypeptide sequence (SEQ ID NOs: 1) which fragment encompasses the fusion junction (which occurs at residue 208 in the first and second fusion protein variants (see FIG. 1 (panel C) and FIG. 7 (bottom panel)). It will be appreciated that antibodies that specifically binding shorter or longer peptides/epitopes encompassing the fusion junction of a CD74-ROS fusion polypeptide are within the scope of the present invention.

The invention is not limited to use of antibodies, but includes equivalent molecules, such as protein binding domains or nucleic acid aptamers, which bind, in a fusion-protein or truncated-protein specific manner, to essentially the same epitope to which a CD74-ROS fusion polypeptide-specific antibody or ROS truncation point epitope-specific antibody useful in the methods of the invention binds. See, e.g., Neuberger et al., *Nature* 312: 604 (1984). Such equivalent non-antibody reagents may be suitably employed in the methods of the invention further described below.

Polyclonal antibodies useful in practicing the methods of the invention may be produced according to standard techniques by immunizing a suitable animal (e.g., rabbit, goat, etc.) with an antigen encompassing a desired fusion-protein specific epitope (e.g. the fusion junction, collecting immune serum from the animal, and separating the polyclonal antibodies from the immune serum, and purifying polyclonal antibodies having the desired specificity, in accordance with known procedures. The antigen may be a synthetic peptide antigen comprising the desired epitopic sequence, selected and constructed in accordance with well-known techniques. See, e.g., Antibodies: A Laboratory Manual, Chapter 5, p. 75-76, Harlow & Lane Eds., Cold Spring Harbor Laboratory (1988); Czernik, *Methods In Enzymology,* 201: 264-283 (1991); Merrifield, *J. Am. Chem. Soc.* 85: 21-49 (1962)). Polyclonal antibodies produced as described herein may be screened and isolated as further described below.

Monoclonal antibodies may also be beneficially employed in the methods of the invention, and may be produced in hybridoma cell lines according to the well-known technique of Kohler and Milstein. *Nature* 265: 495-97 (1975); Kohler and Milstein, *Eur. J. Immunol.* 6: 511 (1976); see also, Current Protocols in Molecular Biology, Ausubel et al. Eds. (1989). Monoclonal antibodies so produced are highly specific, and improve the selectivity and specificity of assay methods provided by the invention. For example, a solution containing the appropriate antigen (e.g. a synthetic peptide comprising the fusion junction of CD74-ROS fusion polypeptide) may be injected into a mouse and, after a sufficient time (in keeping with conventional techniques), the mouse sacrificed and spleen cells obtained. The spleen cells are then immortalized by fusing them with myeloma cells, typically in the presence of polyethylene glycol, to produce hybridoma cells. Rabbit fusion hybridomas, for example, may be produced as described in U.S. Pat. No. 5,675,063, C. Knight, Issued Oct. 7, 1997. The hybridoma cells are then grown in a suitable selection media, such as hypoxanthine-aminopterin-thymidine (HAT), and the supernatant screened for monoclonal antibodies having the desired specificity, as described below. The secreted antibody may be recovered from tissue culture supernatant by conventional methods such as precipitation, ion exchange or affinity chromatography, or the like.

Monoclonal Fab fragments may also be produced in *Escherichia coli* by recombinant techniques known to those skilled in the art. See, e.g., W. Huse, *Science* 246: 1275-81 (1989); Mullinax et al., *Proc. Nat'l Acad. Sci.* 87: 8095 (1990). If monoclonal antibodies of one isotype are preferred for a particular application, particular isotypes can be prepared directly, by selecting from the initial fusion, or prepared secondarily, from a parental hybridoma secreting a monoclonal antibody of different isotype by using the sib selection technique to isolate class-switch variants (Steplewski, et al., *Proc. Nat'l. Acad. Sci.,* 82: 8653 (1985); Spira et al., *J. Immu-*

*nol. Methods,* 74: 307 (1984)). The antigen combining site of the monoclonal antibody can be cloned by PCR and single-chain antibodies produced as phage-displayed recombinant antibodies or soluble antibodies in *E. coli* (see, e.g., ANTIBODY ENGINEERING PROTOCOLS, 1995, Humana Press, Sudhir Paul editor.)

Further still, U.S. Pat. No. 5,194,392, Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, this method involves detecting or determining a sequence of monomers which is a topographical equivalent of a ligand which is complementary to the ligand binding site of a particular receptor of interest. Similarly, U.S. Pat. No. 5,480,971, Houghten et al. (1996) discloses linear $C_1$-C-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

Antibodies useful in the methods of the invention, whether polyclonal or monoclonal, may be screened for epitope and fusion protein specificity according to standard techniques. See, e.g. Czernik et al., *Methods in Enzymology,* 201: 264-283 (1991). For example, the antibodies may be screened against a peptide library by ELISA to ensure specificity for both the desired antigen and, if desired, for reactivity only with a CD74-ROS fusion polypeptide of the invention and not with wild type CD74 or wild type ROS. The antibodies may also be tested by Western blotting against cell preparations containing target protein to confirm reactivity with the only the desired target and to ensure no appreciable binding to other fusion proteins involving ROS. The production, screening, and use of fusion protein-specific antibodies is known to those of skill in the art, and has been described. See, e.g., U.S. Patent Publication No. 20050214301, Wetzel et al., Sep. 29, 2005.

Fusion polypeptide-specific antibodies useful in the methods of the invention may exhibit some limited cross-reactivity with similar fusion epitopes in other fusion proteins or with the epitopes in wild type CD74 and wild type ROS that form the fusion junction. This is not unexpected as most antibodies exhibit some degree of cross-reactivity, and anti-peptide antibodies will often cross-react with epitopes having high homology or identity to the immunizing peptide. See, e.g., Czernik, supra. Cross-reactivity with other fusion proteins is readily characterized by Western blotting alongside markers of known molecular weight. Amino acid sequences of cross-reacting proteins may be examined to identify sites highly homologous or identical to the CD74-ROS fusion polypeptide sequence to which the antibody binds. Undesirable cross-reactivity can be removed by negative selection using antibody purification on peptide columns (e.g. selecting out antibodies that bind either wild type CD74 and/or wild type ROS).

CD74-ROS fusion polypeptide-specific antibodies of the invention that are useful in practicing the methods disclosed herein are ideally specific for human fusion polypeptide, but are not limited only to binding the human species, per se. The invention includes the production and use of antibodies that also bind conserved and highly homologous or identical epitopes in other mammalian species (e.g. mouse, rat, monkey). Highly homologous or identical sequences in other species can readily be identified by standard sequence comparisons, such as using BLAST, with the human CD74-ROS fusion polypeptide sequences disclosed herein (SEQ ID NOs: 1).

Antibodies employed in the methods of the invention may be further characterized by, and validated for, use in a particular assay format, for example FC, IHC, and/or ICC. The use of CD74-ROS fusion polypeptide-specific antibodies in such methods is further described in Section F below. Antibodies may also be advantageously conjugated to fluorescent dyes (e.g. Alexa488, PE), or labels such as quantum dots, for use in multi-parametric analyses along with other signal transduction (phospho-AKT, phospho-Erk 1/2) and/or cell marker (cytokeratin) antibodies, as further described in Section F below.

In practicing the methods of the invention, the expression and/or activity of wild type CD74 and/or wild type ROS in a given biological sample may also be advantageously examined using antibodies (either phospho-specific or total) for these wild type proteins. For example, CSF receptor phosphorylation-site specific antibodies are commercially available (see CELL SIGNALING TECHNOLOGY, INC., Beverly Mass., 2005/06 Catalogue, #'s 3151, 3155, and 3154; and Upstate Biotechnology, 2006 Catalogue, #06-457). Such antibodies may also be produced according to standard methods, as described above. The amino acid sequences of both human CD74 and ROS are published (see FIGS. 3 and 4, and referenced SwissProt Accession Nos.), as are the sequences of these proteins from other species.

Detection of wild type CD74 and wild type ROS expression and/or activation, along with CD74-ROS fusion polypeptide expression, in a biological sample (e.g. a tumor sample) can provide information on whether the fusion protein alone is driving the tumor, or whether wild type ROS is also activated and driving the tumor. Such information is clinically useful in assessing whether targeting the fusion protein or the wild type protein(s), or both, or is likely to be most beneficial in inhibiting progression of the tumor, and in selecting an appropriate therapeutic or combination thereof. Antibodies specific for the wild type ROS kinase extracellular domain, which is not present in the truncated ROS kinase disclosed herein, may be particularly useful for determining the presence/absence of the mutant ROS kinase.

It will be understood that more than one antibody may be used in the practice of the above-described methods. For example, one or more CD74-ROS fusion polypeptide-specific antibodies together with one or more antibodies specific for another kinase, receptor, or kinase substrate that is suspected of being, or potentially is, activated in a cancer in which CD74-ROS fusion polypeptide is expressed may be simultaneously employed to detect the activity of such other signaling molecules in a biological sample comprising cells from such cancer.

Those of skill in the art will appreciate that CD74-ROS fusion polypeptides of the present invention and the fusion junction epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331: 84-86 (1988)). Fusion proteins that have a disulfide-linked dimeric structure due to the IgG part can also be more efficient in binding and neutralizing other molecules than the monomeric CD74-ROS fusion polypeptide alone (Fountoulakis et al., *J Biochem* 270: 3958-3964 (1995)).

Heavy-Isotope Labeled Peptides (AQUA Peptides).

CD74-ROS fusion polypeptide-specific reagents useful in the practice of the disclosed methods may also comprise heavy-isotope labeled peptides suitable for the absolute quantification of expressed CD74-ROS fusion polypeptide in a biological sample. The production and use of AQUA peptides for the absolute quantification of proteins (AQUA) in complex mixtures has been described. See WO/03016861, "Absolute Quantification of Proteins and Modified Forms Thereof by Multistage Mass Spectrometry," Gygi et al. and also Gerber et al. *Proc. Natl. Acad. Sci. U.S.A.* 100: 6940-5 (2003) (the teachings of which are hereby incorporated herein by reference, in their entirety).

The AQUA methodology employs the introduction of a known quantity of at least one heavy-isotope labeled peptide standard (which has a unique signature detectable by LC-SRM chromatography) into a digested biological sample in order to determine, by comparison to the peptide standard, the absolute quantity of a peptide with the same sequence and protein modification in the biological sample. Briefly, the AQUA methodology has two stages: peptide internal standard selection and validation and method development; and implementation using validated peptide internal standards to detect and quantify a target protein in sample. The method is a powerful technique for detecting and quantifying a given peptide/protein within a complex biological mixture, such as a cell lysate, and may be employed, e.g., to quantify change in protein phosphorylation as a result of drug treatment, or to quantify differences in the level of a protein in different biological states.

Generally, to develop a suitable internal standard, a particular peptide (or modified peptide) within a target protein sequence is chosen based on its amino acid sequence and the particular protease to be used to digest. The peptide is then generated by solid-phase peptide synthesis such that one residue is replaced with that same residue containing stable isotopes ($^{13}C$, $^{15}N$). The result is a peptide that is chemically identical to its native counterpart formed by proteolysis, but is easily distinguishable by MS via a 7-Da mass shift. The newly synthesized AQUA internal standard peptide is then evaluated by LC-MS/MS. This process provides qualitative information about peptide retention by reverse-phase chromatography, ionization efficiency, and fragmentation via collision-induced dissociation. Informative and abundant fragment ions for sets of native and internal standard peptides are chosen and then specifically monitored in rapid succession as a function of chromatographic retention to form a selected reaction monitoring (LC-SRM) method based on the unique profile of the peptide standard.

The second stage of the AQUA strategy is its implementation to measure the amount of a protein or modified protein from complex mixtures. Whole cell lysates are typically fractionated by SDS-PAGE gel electrophoresis, and regions of the gel consistent with protein migration are excised. This process is followed by in-gel proteolysis in the presence of the AQUA peptides and LC-SRM analysis. (See Gerber et al. supra.) AQUA peptides are spiked in to the complex peptide mixture obtained by digestion of the whole cell lysate with a proteolytic enzyme and subjected to immunoaffinity purification as described above. The retention time and fragmentation pattern of the native peptide formed by digestion (e.g. trypsinization) is identical to that of the AQUA internal standard peptide determined previously; thus, LC-MS/MS analysis using an SRM experiment results in the highly specific and sensitive measurement of both internal standard and analyte directly from extremely complex peptide mixtures.

Since an absolute amount of the AQUA peptide is added (e.g. 250 fmol), the ratio of the areas under the curve can be used to determine the precise expression levels of a protein or phosphorylated form of a protein in the original cell lysate. In addition, the internal standard is present during in-gel digestion as native peptides are formed, such that peptide extraction efficiency from gel pieces, absolute losses during sample handling (including vacuum centrifugation), and variability during introduction into the LC-MS system do not affect the determined ratio of native and AQUA peptide abundances.

An AQUA peptide standard is developed for a known sequence previously identified by the IAP-LC-MS/MS method within in a target protein. If the site is modified, one AQUA peptide incorporating the modified form of the particular residue within the site may be developed, and a second AQUA peptide incorporating the unmodified form of the residue developed. In this way, the two standards may be used to detect and quantify both the modified an unmodified forms of the site in a biological sample.

Peptide internal standards may also be generated by examining the primary amino acid sequence of a protein and determining the boundaries of peptides produced by protease cleavage. Alternatively, a protein may actually be digested with a protease and a particular peptide fragment produced can then sequenced. Suitable proteases include, but are not limited to, serine proteases (e.g. trypsin, hepsin), metallo proteases (e.g. PUMP1), chymotrypsin, cathepsin, pepsin, thermolysin, carboxypeptidases, etc.

A peptide sequence within a target protein is selected according to one or more criteria to optimize the use of the peptide as an internal standard. Preferably, the size of the peptide is selected to minimize the chances that the peptide sequence will be repeated elsewhere in other non-target proteins. Thus, a peptide is preferably at least about 6 amino acids. The size of the peptide is also optimized to maximize ionization frequency. Thus, peptides longer than about 20 amino acids are not preferred. The preferred ranged is about 7 to 15 amino acids. A peptide sequence is also selected that is not likely to be chemically reactive during mass spectrometry, thus sequences comprising cysteine, tryptophan, or methionine are avoided.

A peptide sequence that does not include a modified region of the target region may be selected so that the peptide internal standard can be used to determine the quantity of all forms of the protein. Alternatively, a peptide internal standard encompassing a modified amino acid may be desirable to detect and quantify only the modified form of the target protein. Peptide standards for both modified and unmodified regions can be used together, to determine the extent of a modification in a particular sample (i.e. to determine what fraction of the total amount of protein is represented by the modified form). For example, peptide standards for both the phosphorylated and unphosphorylated form of a protein known to be phosphorylated at a particular site can be used to quantify the amount of phosphorylated form in a sample.

The peptide is labeled using one or more labeled amino acids (i.e. the label is an actual part of the peptide) or less preferably, labels may be attached after synthesis according to standard methods. Preferably, the label is a mass-altering label selected based on the following considerations: The mass should be unique to shift fragments masses produced by MS analysis to regions of the spectrum with low background; the ion mass signature component is the portion of the labeling moiety that preferably exhibits a unique ion mass signature in MS analysis; the sum of the masses of the constituent atoms of the label is preferably uniquely different than the fragments of all the possible amino acids. As a result, the labeled amino acids and peptides are readily distinguished from unlabeled ones by the ion/mass pattern in the resulting mass spectrum. Preferably, the ion mass signature component imparts a mass to a protein fragment that does not match the residue mass for any of the 20 natural amino acids.

The label should be robust under the fragmentation conditions of MS and not undergo unfavorable fragmentation. Labeling chemistry should be efficient under a range of conditions, particularly denaturing conditions, and the labeled tag preferably remains soluble in the MS buffer system of choice. The label preferably does not suppress the ionization efficiency of the protein and is not chemically reactive. The label may contain a mixture of two or more isotopically distinct species to generate a unique mass spectrometric pattern at each labeled fragment position. Stable isotopes, such as $^{2}H$, $^{13}C$, $^{15}N$, $^{17}O$, $^{18}O$, or $^{34}S$, are among preferred labels. Pairs of peptide internal standards that incorporate a different isotope label may also be prepared. Preferred amino acid residues into which a heavy isotope label may be incorporated include leucine, proline, valine, and phenylalanine.

Peptide internal standards are characterized according to their mass-to-charge (m/z) ratio, and preferably, also according to their retention time on a chromatographic column (e.g. an HPLC column). Internal standards that co-elute with unlabeled peptides of identical sequence are selected as optimal internal standards. The internal standard is then analyzed by fragmenting the peptide by any suitable means, for example by collision-induced dissociation (CID) using, e.g., argon or helium as a collision gas. The fragments are then analyzed, for example by multi-stage mass spectrometry ($MS^n$) to obtain a fragment ion spectrum, to obtain a peptide fragmentation signature. Preferably, peptide fragments have significant differences in m/z ratios to enable peaks corresponding to each fragment to be well separated, and a signature is that is unique for the target peptide is obtained. If a suitable fragment signature is not obtained at the first stage, additional stages of MS are performed until a unique signature is obtained.

Fragment ions in the MS/MS and $MS^3$ spectra are typically highly specific for the peptide of interest, and, in conjunction with LC methods, allow a highly selective means of detecting and quantifying a target peptide/protein in a complex protein mixture, such as a cell lysate, containing many thousands or tens of thousands of proteins. Any biological sample potentially containing a target protein/peptide of interest may be assayed. Crude or partially purified cell extracts are preferably employed. Generally, the sample has at least 0.01 mg of protein, typically a concentration of 0.1-10 mg/mL, and may be adjusted to a desired buffer concentration and pH.

A known amount of a labeled peptide internal standard, preferably about 10 femtomoles, corresponding to a target protein to be detected/quantified is then added to a biological sample, such as a cell lysate. The spiked sample is then digested with one or more protease(s) for a suitable time period to allow digestion. A separation is then performed (e.g. by HPLC, reverse-phase HPLC, capillary electrophoresis, ion exchange chromatography, etc.) to isolate the labeled internal standard and its corresponding target peptide from other peptides in the sample. Microcapillary LC is a preferred method.

Each isolated peptide is then examined by monitoring of a selected reaction in the MS. This involves using the prior knowledge gained by the characterization of the peptide internal standard and then requiring the MS to continuously monitor a specific ion in the MS/MS or $MS^n$ spectrum for both the peptide of interest and the internal standard. After elution, the area under the curve (AUC) for both peptide standard and target peptide peaks are calculated. The ratio of the two areas provides the absolute quantification that can be normalized for the number of cells used in the analysis and the protein's molecular weight, to provide the precise number of copies of the protein per cell. Further details of the AQUA methodology are described in Gygi et al., and Gerber et al. supra.

AQUA internal peptide standards (heavy-isotope labeled peptides) may desirably be produced, as described above, to detect any quantify any unique site (e.g. the fusion junction within a CD74-ROS fusion polypeptide) within a mutant ROS polypeptide of the invention. For example, an AQUA phosphopeptide may be prepared that corresponds to the fusion junction sequence of CD74-ROS fusion polypeptide Peptide standards for may be produced for the CD74-ROS fusion junction and such standards employed in the AQUA methodology to detect and quantify the fusion junction (i.e. the presence of CD74-ROS fusion polypeptide) in a biological sample.

For example, an exemplary AQUA peptide of the invention comprises the amino acid sequence LVGDDF, which corresponds to the three amino acids immediately flanking each side of the fusion junction in the second (short) variant of CD74-ROS fusion polypeptide. It will be appreciated that larger AQUA peptides comprising the fusion junction sequence (and additional residues downstream or upstream of it) may also be constructed. Similarly, a smaller AQUA peptide comprising less than all of the residues of such sequence (but still comprising the point of fusion junction itself) may alternatively be constructed. Such larger or shorter AQUA peptides are within the scope of the present invention, and the selection and production of preferred AQUA peptides may be carried out as described above (see Gygi et al., Gerber et al., supra.).

Nucleic Acid Probes.

Fusion-specific reagents provided by the invention also include nucleic acid probes and primers suitable for detection of a CD74-ROS polynucleotide, as described in detail in Section B above. The specific use of such probes in assays such as fluorescence in-situ hybridization (FISH) or PCR amplification is described in Section F below.

Also provided by the invention is a kit for the detection of a CD74-ROS fusion polynucleotide and/or polypeptide in a biological sample, the kit comprising at least one fusion polynucleotide- or polypeptide-specific reagent of the invention, and one or more secondary reagents. Suitable secondary reagents for employment in a kit are familiar to those of skill in the art, and include, by way of example, buffers, detectable secondary antibodies or probes, kinases, activating agents, kinase substrates, and the like.

F. Diagnostic Applications & Assay Formats.

The methods of the invention may be carried out in a variety of different assay formats known to those of skill in the art.

Immunoassays.

Immunoassays useful in the practice of the methods of the invention may be homogenous immunoassays or heterogeneous immunoassays. In a homogeneous assay the immunological reaction usually involves a mutant ROS polypeptide-specific reagent (e.g. a CD74-ROS fusion polypeptide-specific antibody), a labeled analyte, and the biological sample of interest. The signal arising from the label is modified, directly or indirectly, upon the binding of the antibody to the labeled analyte. Both the immunological reaction and detection of the extent thereof are carried out in a homogeneous solution. Immunochemical labels that may be employed include free radicals, radio-isotopes, fluorescent dyes, enzymes, bacteriophages, coenzymes, and so forth. Semi-conductor nanocrystal labels, or "quantum dots", may also be advantageously employed, and their preparation and use has been well described. See generally, K. Barovsky, *Nanotech. Law & Bus.* 1(2): Article 14 (2004) and patents cited therein.

In a heterogeneous assay approach, the reagents are usually the biological sample, a mutant ROS kinase polypeptide-specific reagent (e.g., an antibody), and suitable means for producing a detectable signal. Biological samples as further described below may be used. The antibody is generally immobilized on a support, such as a bead, plate or slide, and contacted with the sample suspected of containing the antigen in a liquid phase. The support is then separated from the liquid phase and either the support phase or the liquid phase is examined for a detectable signal employing means for producing such signal. The signal is related to the presence of the analyte in the biological sample. Means for producing a detectable signal include the use of radioactive labels, fluorescent labels, enzyme labels, quantum dots, and so forth. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are the radioimmunoassay, immunofluorescence methods, enzyme-linked immunoassays, and the like.

Immunoassay formats and variations thereof, which may be useful for carrying out the methods disclosed herein, are well known in the art. See generally E. Maggio, Enzyme-Immunoassay, (1980) (CRC Press, Inc., Boca Raton, Fla.); see also, e.g., U.S. Pat. No. 4,727,022 (Skold et al., "Methods for Modulating Ligand-Receptor Interactions and their Application"); U.S. Pat. No. 4,659,678 (Forrest et al., "Immunoassay of Antigens"); U.S. Pat. No. 4,376,110 (David et al., "Immunometric Assays Using Monoclonal Antibodies"). Conditions suitable for the formation of reagent-antibody complexes are well known to those of skill in the art. See id. CD74-ROS fusion polypeptide-specific monoclonal antibodies may be used in a "two-site" or "sandwich" assay, with a single hybridoma cell line serving as a source for both the labeled monoclonal antibody and the bound monoclonal antibody. Such assays are described in U.S. Pat. No. 4,376,110. The concentration of detectable reagent should be sufficient such that the binding of CD74-ROS fusion polypeptide is detectable compared to background.

Antibodies useful in the practice of the methods disclosed herein may be conjugated to a solid support suitable for a diagnostic assay (e.g., beads, plates, slides or wells formed from materials such as latex or polystyrene) in accordance with known techniques, such as precipitation. Antibodies or other CD74-ROS fusion polypeptide-binding reagents may likewise be conjugated to detectable groups such as radiolabels (e.g., $^{35}$S, $^{125}$I, $^{131}$I, enzyme labels (e.g., horseradish peroxidase, alkaline phosphatase), and fluorescent labels (e.g., fluorescein) in accordance with known techniques.

Cell-based assays, such flow cytometry (FC), immuno-histochemistry (IHC), or immunofluorescence (IF) are particularly desirable in practicing the methods of the invention, since such assay formats are clinically-suitable, allow the detection of mutant ROS polypeptide expression in vivo, and avoid the risk of artifact changes in activity resulting from manipulating cells obtained from, e.g. a tumor sample in order to obtain extracts. Accordingly, in some preferred embodiment, the methods of the invention are implemented in a flow-cytometry (FC), immuno-histochemistry (IHC), or immunofluorescence (IF) assay format.

Flow cytometry (FC) may be employed to determine the expression of mutant ROS polypeptide in a mammalian tumor before, during, and after treatment with a drug targeted at inhibiting ROS kinase activity. For example, tumor cells from a fine needle aspirate may be analyzed by flow cytometry for CD74-ROS fusion polypeptide expression and/or activation, as well as for markers identifying cancer cell types, etc., if so desired. Flow cytometry may be carried out according to standard methods. See, e.g. Chow et al., *Cytometry* (*Communications in Clinical Cytometry*) 46: 72-78 (2001). Briefly and by way of example, the following protocol for cytometric analysis may be employed: fixation of the cells with 2% paraformaldehyde for 10 minutes at 37° C. followed by permeabilization in 90% methanol f0 minutes on ice. Cells may then be stained with the primary CD74-ROS fusion polypeptide-specific antibody, washed and labeled with a fluorescent-labeled secondary antibody. The cells would then be analyzed on a flow cytometer (e.g. a Beckman Coulter FC500) according to the specific protocols of the instrument used. Such an analysis would identify the level of expressed CD74-ROS fusion polypeptide in the tumor. Similar analysis after treatment of the tumor with a ROS-inhibiting therapeutic would reveal the responsiveness of a CD74-ROS fusion polypeptide-expressing tumor to the targeted inhibitor of ROS kinase.

Immunohistochemical (IHC) staining may be also employed to determine the expression and/or activation status of mutant ROS kinase polypeptide in a mammalian cancer (e.g. NSCLC) before, during, and after treatment with a drug targeted at inhibiting ROS kinase activity. IHC may be carried out according to well-known techniques. See, e.g., Antibodies: A Laboratory Manual, Chapter 10, Harlow & Lane Eds., Cold Spring Harbor Laboratory (1988). Briefly, and by way of example, paraffin-embedded tissue (e.g. tumor tissue from a biopsy) is prepared for immunohistochemical staining by deparaffinizing tissue sections with xylene followed by ethanol; hydrating in water then PBS; unmasking antigen by heating slide in sodium citrate buffer; incubating sections in hydrogen peroxide; blocking in blocking solution; incubating slide in primary anti-CD74-ROS fusion polypeptide antibody and secondary antibody; and finally detecting using ABC avidin/biotin method according to manufacturer's instructions.

Immunofluorescence (IF) assays may be also employed to determine the expression and/or activation status of CD74-ROS fusion polypeptide in a mammalian cancer before, during, and after treatment with a drug targeted at inhibiting ROS kinase activity. IF may be carried out according to well-known techniques. See, e.g., J. M. polak and S. Van Noorden (1997) Introduction to Immunocytochemistry, 2nd Ed.; Royal Microscopy Society Microscopy Handbook 37, BioScientific/Springer-Verlag. Briefly, and by way of example, patient samples may be fixed in paraformaldehyde followed by methanol, blocked with a blocking solution such as horse serum, incubated with the primary antibody against CD74-ROS fusion polypeptide followed by a secondary antibody labeled with a fluorescent dye such as Alexa 488 and analyzed with an epifluorescent microscope.

Antibodies employed in the above-described assays may be advantageously conjugated to fluorescent dyes (e.g. Alexa488, PE), or other labels, such as quantum dots, for use in multi-parametric analyses along with other signal transduction (EGFR, phospho-AKT, phospho-Erk 1/2) and/or cell marker (cytokeratin) antibodies.

A variety of other protocols, including enzyme-linked immunosorbent assay (ELISA), radio-immunoassay (RIA), and fluorescent-activated cell sorting (FACS), for measuring mutant ROS kinase polypeptides are known in the art and provide a basis for diagnosing altered or abnormal levels of CD74-ROS fusion polypeptide expression. Normal or standard values for CD74-ROS fusion polypeptide expression are established by combining body fluids or cell extracts taken from normal mammalian subjects, preferably human, with antibody to CD74-ROS fusion polypeptide under conditions suitable for complex formation. The amount of standard complex formation may be quantified by various methods, but preferably by photometric means. Quantities of CD74-ROS fusion polypeptide expressed in subject, control, and disease samples from biopsied tissues are compared with the standard values. Deviation between standard and subject values establishes the parameters for diagnosing disease.

Peptide & Nucleotide Assays.

Similarly, AQUA peptides for the detection/quantification of expressed mutant ROS polypeptide in a biological sample comprising cells from a tumor may be prepared and used in standard AQUA assays, as described in detail in Section E above. Accordingly, in some preferred embodiments of the methods of the invention, the CD74-ROS fusion polypeptide-specific reagent comprises a heavy isotope labeled phosphopeptide (AQUA peptide) corresponding to a peptide sequence comprising the fusion junction of CD74-ROS fusion polypeptide, as described above in Section E.

Mutant ROS kinase polypeptide-specific reagents useful in practicing the methods of the invention may also be mRNA, oligonucleotide or DNA probes that can directly hybridize to, and detect, fusion or truncated polypeptide expression transcripts in a biological sample. Such probes are discussed in detail in Section B above. Briefly, and by way of example, formalin-fixed, paraffin-embedded patient samples may be probed with a fluorescein-labeled RNA probe followed by washes with formamide, SSC and PBS and analysis with a fluorescent microscope.

Polynucleotides encoding mutant ROS kinase polypeptide may also be used for diagnostic purposes. The polynucleotides that may be used include oligonucleotide sequences, antisense RNA and DNA molecules, and PNAs. The polynucleotides may be used to detect and quantitate gene expression in biopsied tissues in which expression of CD74-ROS fusion polypeptide or truncated ROS polypeptide may be correlated with disease. The diagnostic assay may be used to distinguish between absence, presence, and excess expression of CD74-ROS fusion polypeptide, and to monitor regulation of CD74-ROS fusion polypeptide levels during therapeutic intervention.

In one preferred embodiment, hybridization with PCR probes which are capable of detecting polynucleotide sequences, including genomic sequences, encoding CD74-ROS fusion polypeptide or truncated ROS kinase polypeptide or closely related molecules, may be used to identify nucleic acid sequences that encode mutant ROS polypeptide. The construction and use of such probes is described in Section B above. The specificity of the probe, whether it is made from a highly specific region, e.g., 10 unique nucleotides in the fusion junction, or a less specific region, e.g., the 3' coding region, and the stringency of the hybridization or amplification (maximal, high, intermediate, or low) will determine whether the probe identifies only naturally occurring sequences encoding mutant ROS kinase polypeptide, alleles, or related sequences.

Probes may also be used for the detection of related sequences, and should preferably contain at least 50% of the nucleotides from any of the mutant ROS polypeptide encoding sequences. The hybridization probes of the subject invention may be DNA or RNA and derived from the nucleotide sequences of SEQ ID NOs: 2, most preferably encompassing the fusion junction, or from genomic sequence including promoter, enhancer elements, and introns of the naturally occurring CD74 and ROS polypeptides, as further described in Section B above.

A CD74-ROS fusion polynucleotide or truncated ROS polynucleotide of the invention may be used in Southern or northern analysis, dot blot, or other membrane-based technologies; in PCR technologies; or in dip stick, pin, ELISA or chip assays utilizing fluids or tissues from patient biopsies to detect altered mutant ROS kinase polypeptide expression. Such qualitative or quantitative methods are well known in the art. In a particular aspect, the nucleotide sequences encoding mutant ROS polypeptide may be useful in assays that detect activation or induction of various cancers, including cancers of the lung including NSCLC. Mutant ROS polynucleotides may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding CD74-ROS fusion polypeptide or truncated ROS kinase polypeptide in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease characterized by expression of mutant ROS polypeptide, a normal or standard profile for expression is established. This may be accomplished by combining body fluids or cell extracts taken from normal subjects, either animal or human, with a sequence, or a fragment thereof, which encodes CD74-ROS fusion polypeptide or truncated ROS kinase polypeptide, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

Additional diagnostic uses for mutant ROS polynucleotides of the invention may involve the use of polymerase chain reaction (PCR), another preferred assay format that is standard to those of skill in the art. See, e.g., MOLECULAR CLONING, A LABORATORY MANUAL, 2nd. edition, Sambrook, J., Fritsch, E. F. and Maniatis, T., eds., Cold Spring Harbor Laboratory Press, Cold Spring Harbor, N.Y. (1989). PCR oligomers may be chemically synthesized, generated enzymatically, or produced from a recombinant source. Oligomers will preferably consist of two nucleotide sequences, one with sense orientation (5' to 3') and another with antisense (3' to 5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of CD74-ROS fusion polypeptide or truncated ROS kinase polypeptide include radiolabeling or biotinylating nucleotides, coamplification of a control nucleic acid, and standard curves onto which the experimental results are interpolated (Melby et al., *J. Immunol. Methods,* 159: 235-244 (1993); Duplaa et al. Anal. Biochem. 229-236 (1993)). The speed of quantitation of multiple samples may be accelerated by running the assay in an ELISA format where the oligomer of interest is presented in various dilutions and a spectrophotometric or colorimetric response gives rapid quantitation.

In another embodiment of the invention, the mutant ROS polynucleotides of the invention may be used to generate hybridization probes which are useful for mapping the naturally occurring genomic sequence. The sequences may be mapped to a particular chromosome or to a specific region of the chromosome using well known techniques. Such techniques include fluorescence in-situ hybridization (FISH), FACS, or artificial chromosome constructions, such as yeast artificial chromosomes, bacterial artificial chromosomes, bacterial P1 constructions or single chromosome cDNA libraries, as reviewed in Price, C. M., *Blood Rev.* 7: 127-134 (1993), and Trask, B. J., *Trends Genet.* 7: 149-154 (1991).

In one preferred embodiment, FISH is employed (as described in Verma et al. HUMAN CHROMOSOMES: A MANUAL OF BASIC TECHNIQUES, Pergamon Press, New York, N.Y. (1988)) and may be correlated with other physical chromosome mapping techniques and genetic map data. Examples of genetic map data can be found in the 1994 Genome Issue of Science (265: 1981f). Correlation between the location of the gene encoding CD74-ROS fusion polypeptide or truncated ROS polypeptide on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22-23 (Gatti et al., *Nature* 336: 577-580 (1988)), any sequences mapping to that area may represent associated or regulatory genes for further investigation. The nucleotide sequence of the subject invention may also be used to detect differences in the chromosomal location due to translocation, inversion, etc., among normal, carrier, or affected individuals.

Biological Samples

Biological samples useful in the practice of the methods of the invention may be obtained from any mammal in which a cancer characterized by the presence of a CD74-ROS fusion polypeptide is or might be present or developing. In one embodiment, the mammal is a human, and the human may be a candidate for a ROS-inhibiting therapeutic, for the treatment of a lung cancer, e.g. NSCLC. The human candidate may be a patient currently being treated with, or considered for treatment with, a ROS kinase inhibitor. In another embodiment, the mammal is large animal, such as a horse or cow, while in other embodiments, the mammal is a small animal, such as a dog or cat, all of which are known to develop cancers, including lung cancers.

Any biological sample comprising cells (or extracts of cells) from a mammalian cancer is suitable for use in the methods of the invention. In one embodiment, the biological sample comprises cells obtained from a tumor biopsy. The biopsy may be obtained, according to standard clinical techniques, from primary tumors occurring in an organ of a mammal, or by secondary tumors that have metastasized in other tissues. In another embodiment, the biological sample comprises cells obtained from a fine needle aspirate taken from a tumor, and techniques for obtaining such aspirates are well known in the art (see Cristallini et al., *Acta Cytol.* 36(3): 416-22 (1992))

The biological sample may also comprise cells obtained from an effusion, such as a pleural effusion. Pleural effusions (liquid that forms outside the lung in the thoracic cavity and which contains cancerous cells) are known to form in many patients with advanced lung cancer (including NSCLC), and the presence of such effusion is predictive of a poor outcome and short survival time. Standard techniques for obtaining pleural effusion samples have been described and are well known in the art (see Sahn, *Clin Chest Med.* 3(2): 443-52 (1982)). Circulating tumor cells may also be obtained from serum using tumor markers, cytokeratin protein markers or other methods of negative selection as described (see Ma et al., *Anticancer Res.* 23(1A): 49-62 (2003)). Serum and bone marrow samples may be particularly preferred for patients with leukemia. Aberrant expression of ROS has been observed in a glioblastoma. See Charest et al., supra.

A biological sample may comprise cells (or cell extracts) from a cancer in which CD74-ROS fusion polypeptide or truncated ROS kinase polypeptide is expressed and/or activated but wild type ROS kinase is not. Alternatively, the sample may comprise cells from a cancer in which both mutant ROS polypeptide and wild type ROS kinase are expressed and/or activated, or in which wild type ROS kinase and/or CD74 are expressed and/or active, but mutant ROS polypeptide is not.

Cellular extracts of the foregoing biological samples may be prepared, either crude or partially (or entirely) purified, in accordance with standard techniques, and used in the methods of the invention. Alternatively, biological samples comprising whole cells may be utilized in preferred assay formats such as immunohistochemistry (IHC), flow cytometry (FC), and immunofluorescence (IF), as further described above. Such whole-cell assays are advantageous in that they minimize manipulation of the tumor cell sample and thus reduce the risks of altering the in vivo signaling/activation state of the cells and/or introducing artifact signals. Whole cell assays are also advantageous because they characterize expression and signaling only in tumor cells, rather than a mixture of tumor and normal cells.

In practicing the disclosed method for determining whether a compound inhibits progression of a tumor characterized by a CD74-ROS translocation and/or fusion polypeptide, biological samples comprising cells from mammalian xenografts (or bone marrow transplants) may also be advantageously employed. Preferred xenografts (or transplant recipients) are small mammals, such as mice, harboring human tumors (or leukemias) that express a mutant ROS kinase polypeptide. Xenografts harboring human tumors are well known in the art (see Kal, *Cancer Treat Res.* 72: 155-69 (1995)) and the production of mammalian xenografts harboring human tumors is well described (see Winograd et al., *In Vivo.* 1(1): 1-13 (1987)). Similarly the generation and use of bone marrow transplant models is well described (see, e.g., Schwaller, et al., *EMBO J.* 17: 5321-333 (1998); Kelly et al., *Blood* 99: 310-318 (2002)). By "cancer characterized by" a CD74-ROS translocation and/or fusion polypeptide is meant a cancer in which such mutant ROS gene and/or expressed polypeptide are present, as compared to a cancer in which such translocation and/or fusion polypeptide are not present.

In assessing mutant ROS polynucleotide presence or polypeptide expression in a biological sample comprising cells from a mammalian cancer tumor, a control sample representing a cell in which such translocation and/or fusion protein do not occur may desirably be employed for comparative purposes. Ideally, the control sample comprises cells from a subset of the particular cancer (e.g. NSCLC) that is representative of the subset in which the mutation (e.g. CD74-ROS translocation) does not occur and/or the fusion polypeptide is not expressed. Comparing the level in the control sample versus the test biological sample thus identifies whether the mutant polynucleotide and/or polypeptide is/are present. Alternatively, since CD74-ROS fusion polynucleotide and/or polypeptide may not be present in the majority of cancers, any tissue that similarly does not express mutant ROS polypeptide (or harbor the mutant polynucleotide) may be employed as a control.

The methods described below will have valuable diagnostic utility for cancers characterized by mutant ROS polynucleotide and/or polypeptide, and treatment decisions pertaining to the same. For example, biological samples may be obtained from a subject that has not been previously diagnosed as having a cancer characterized by since a CD74-ROS translocation and/or fusion polypeptide, nor has yet undergone treatment for such cancer, and the method is employed to diagnostically identify a tumor in such subject as belonging to a subset of tumors (e.g. NSCLC tumors) in which mutant ROS polynucleotide and/or polypeptide is present/expressed.

Alternatively, a biological sample may be obtained from a subject that has been diagnosed as having a cancer driven by one type of kinase, such as EFGR, and has been receiving therapy, such as EGFR inhibitor therapy (e.g. Tarceva™, Iressa™) for treatment of such cancer, and the method of the invention is employed to identify whether the subject's tumor is also characterized by a CD74-ROS translocation and/or fusion polypeptide, and is therefore likely to fully respond to the existing therapy and/or whether alternative or additional ROS kinase-inhibiting therapy is desirable or warranted. The methods of the invention may also be employed to monitor the progression or inhibition of a mutant ROS polypeptide-expressing cancer following treatment of a subject with a composition comprising a ROS kinase-inhibiting therapeutic or combination of therapeutics.

Such diagnostic assay may be carried out subsequent to or prior to preliminary evaluation or surgical surveillance procedures. The identification method of the invention may be advantageously employed as a diagnostic to identify patients having cancer, such as NSCLC, driven by the CD74-ROS fusion protein, which patients would be most likely to respond to therapeutics targeted at inhibiting ROS kinase activity. The ability to select such patients would also be useful in the clinical evaluation of efficacy of future ROS-targeted therapeutics as well as in the future prescription of such drugs to patients.

Diagnostics.

The ability to selectively identify cancers in which a CD74-ROS translocation and/or fusion polypeptide is/are present enables important new methods for accurately identifying such tumors for diagnostic purposes, as well as obtaining information useful in determining whether such a tumor is likely to respond to a ROS-inhibiting therapeutic composition, or likely to be partially or wholly non-responsive to an inhibitor targeting a different kinase when administered as a single agent for the treatment of the cancer.

Accordingly, in one embodiment, the invention provides a method for detecting the presence of a mutant ROS polynucleotide and/or polypeptide in a cancer, the method comprising the steps of: (a) obtaining a biological sample from a patient having cancer; and (b) utilizing at least one reagent that detects a mutant ROS polynucleotide or polypeptide of the invention to determine whether a CD74-ROS fusion polynucleotide and/or polypeptide is/are present in the biological sample.

In some preferred embodiments, the cancer is a lung cancer, such as non-small cell lung carcinoma (NSCLC). In other preferred embodiments, the presence of a mutant ROS kinase polypeptide identifies a cancer that is likely to respond to a composition comprising at least one ROS kinase-inhibiting therapeutic.

In some preferred embodiments, the diagnostic methods of the invention are implemented in a flow-cytometry (FC), immuno-histochemistry (IHC), or immuno-fluorescence (IF) assay format. In another preferred embodiment, the activity of the CD74-ROS fusion polypeptide is detected. In other preferred embodiments, the diagnostic methods of the invention are implemented in a fluorescence in situ hybridization (FISH) or polymerase chain reaction (PCR) assay format.

The invention further provides a method for determining whether a compound inhibits the progression of a cancer characterized by a CD74-ROS fusion polynucleotide or polypeptide, said method comprising the step of determining whether said compound inhibits the expression and/or activity of said CD74-ROS fusion in said cancer. In one preferred embodiment, inhibition of expression and/or activity of the CD74-ROS fusion polypeptide is determined using at least one reagent that detects an CD74-ROS fusion polynucleotide or polypeptide of the invention. Compounds suitable for inhibition of ROS kinase activity are discussed in more detail in Section G below.

Mutant ROS polynucleotide probes and polypeptide-specific reagents useful in the practice of the methods of the invention are described in further detail in sections B and D above. In one preferred embodiment, the CD74-ROS fusion polypeptide-specific reagent comprises a fusion polypeptide-specific antibody. In another preferred embodiment, the fusion polypeptide-specific reagent comprises a heavy-isotope labeled phosphopeptide (AQUA peptide) corresponding to the fusion junction of CD74-ROS fusion polypeptide The methods of the invention described above may also optionally comprise the step of determining the level of expression or activation of other kinases, such as wild type ROS and EGFR, or other downstream signaling molecules in said biological sample. Profiling both CD74-ROS fusion polypeptide expression/activation and expression/activation of other kinases and pathways in a given biological sample can provide valuable information on which kinase(s) and pathway(s) is/are driving the disease, and which therapeutic regime is therefore likely to be of most benefit.

Compound Screening.

The discovery of the novel CD74-ROS fusion polypeptides described herein also enables the development of new compounds that inhibit the activity of these mutant ROS proteins, particularly their ROS kinase activity. Accordingly, the invention also provides, in part, a method for determining whether a compound inhibits the progression of a cancer characterized by a CD74-ROS fusion polynucleotide and/or polypeptide, said method comprising the step of determining whether said compound inhibits the expression and/or activity of said CD74-ROS fusion polypeptide in said cancer. In one preferred embodiment, inhibition of expression and/or activity of the CD74-ROS fusion polypeptide is determined using at least one reagent that detects a mutant ROS polynucleotide and/or mutant ROS polypeptide of the invention. Preferred reagents of the invention have been described above. Compounds suitable for the inhibition of ROS kinase activity are described in more detail in Section G below.

The compound may, for example, be a kinase inhibitor, such as a small molecule or antibody inhibitor. It may be a pan-kinase inhibitor with activity against several different kinases, or a kinase-specific inhibitor. ROS kinase-inhibiting compounds are discussed in further detail in Section G below. Patient biological samples may be taken before and after treatment with the inhibitor and then analyzed, using methods described above, for the biological effect of the inhibitor on ROS kinase activity, including the phosphorylation of downstream substrate protein. Such a pharmacodynamic assay may be useful in determining the biologically active dose of the drug that may be preferable to a maximal tolerable dose. Such information would also be useful in submissions for drug approval by demonstrating the mechanism of drug action. Identifying compounds with such desired inhibitory characteristics is further described in Section G below.

G. Therapeutic Inhibition of Cancers.

In accordance with the present invention, it has now been shown that the CD74-ROS fusion polypeptide occurs in at least one subgroup of human NSCLC. Accordingly, the progression of a mammalian cancer (e.g. NSCLC) in which CD74-ROS fusion protein is expressed may be inhibited, in vivo, by inhibiting the activity of ROS kinase in such cancer. ROS activity in cancers characterized by expression of a mutant ROS kinase may be inhibited by contacting the cancer (e.g. a tumor) with a ROS kinase-inhibiting therapeutic. Accordingly, the invention provides, in part, a method for inhibiting the progression of a CD74-ROS fusion polypeptide-expressing cancer by inhibiting the expression and/or activity of ROS kinase in the cancer.

A ROS kinase-inhibiting therapeutic may be any composition comprising at least one compound, biological or chemical, which inhibits, directly or indirectly, the expression and/or activity of ROS kinase in vivo, including the exemplary classes of compounds described below. Such compounds include therapeutics that act directly on ROS kinase itself, or on proteins or molecules that modify the activity of ROS, or that act indirectly by inhibiting the expression of ROS. Such compositions also include compositions comprising only a single ROS kinase inhibiting compound, as well as compositions comprising multiple therapeutics (including those against other RTKs), which may also include a non-specific therapeutic agent like a chemotherapeutic agent or general transcription inhibitor.

Small-Molecule Inhibitors.

In some preferred embodiments, a ROS-inhibiting therapeutic useful in the practice of the methods of the invention is a targeted, small molecule inhibitor. Small molecule targeted inhibitors are a class of molecules that typically inhibit the activity of their target enzyme by specifically, and often irreversibly, binding to the catalytic site of the enzyme, and/or binding to an ATP-binding cleft or other binding site within the enzyme that prevents the enzyme from adopting a conformation necessary for its activity. An exemplary small-molecule targeted kinase inhibitor is Gleevec® (Imatinib, STI-571), which inhibits CSF1R and BCR-ABL, and its properties have been well described. See Dewar et al., *Blood* 105(8): 3127-32 (2005).

Small molecule inhibitors may be rationally designed using X-ray crystallographic or computer modeling of ROS kinase three-dimensional structure, or may found by high throughput screening of compound libraries for inhibition of ROS. Such methods are well known in the art, and have been described. Specificity of ROS inhibition may be confirmed, for example, by examining the ability of such compound to inhibit ROS activity, but not other kinase activity, in a panel of kinases, and/or by examining the inhibition of ROS activity in a biological sample comprising NSCLC tumor cells, as described above. Such screening methods are further described below.

Antibody Inhibitors.

ROS kinase-inhibiting therapeutics useful in the methods of the invention may also be targeted antibodies that specifically bind to critical catalytic or binding sites or domains required for ROS activity, and inhibit the kinase by blocking access of ligands, substrates or secondary molecules to a and/or preventing the enzyme from adopting a conformation necessary for its activity. The production, screening, and therapeutic use of humanized target-specific antibodies has been well-described. See Merluzzi et al., *Adv Clin Path.* 4(2): 77-85 (2000). Commercial technologies and systems, such as Morphosys, Inc.'s Human Combinatorial Antibody Library (HuCAL®), for the high-throughput generation and screening of humanized target-specific inhibiting antibodies are available.

The production of various anti-receptor kinase targeted antibodies and their use to inhibit activity of the targeted receptor has been described. See, e.g. U.S. Patent Publication No. 20040202655, "Antibodies to IGF-I Receptor for the Treatment of Cancers," Oct. 14, 2004, Morton et al.; U.S. Patent Publication No. 20040086503, "Human anti-Epidermal Growth Factor Receptor Single-Chain Antibodies," Apr. 15, 2004, Raisch et al.; U.S. Patent Publication No. 20040033543, "Treatment of Renal Carcinoma Using Antibodies Against the EGFr," Feb. 19, 2004, Schwab et. al. Standardized methods for producing, and using, receptor tyrosine kinase activity-inhibiting antibodies are known in the art. See, e.g., European Patent No. EP1423428, "Antibodies that Block Receptor Tyrosine Kinase Activation, Methods of Screening for and Uses Thereof," Jun. 2, 2004, Borges et al.

Phage display approaches may also be employed to generate ROS-specific antibody inhibitors, and protocols for bacteriophage library construction and selection of recombinant antibodies are provided in the well-known reference text CURRENT PROTOCOLS IN IMMUNOLOGY, Colligan et al. (Eds.), John Wiley & Sons, Inc. (1992-2000), Chapter 17, Section 17.1. See also U.S. Pat. No. 6,319,690, Nov. 20, 2001, Little et al.; U.S. Pat. No. 6,300,064, Oct. 9, 2001, Knappik et al.; U.S. Pat. No. 5,840,479, Nov. 24, 1998, Little et al.; U.S. Patent Publication No. 20030219839, Nov. 27, 2003, Bowdish et al.

A library of antibody fragments displayed on the surface of bacteriophages may be produced (see, e.g. U.S. Pat. No. 6,300,064, Oct. 9, 2001, Knappik et al.) and screened for binding to a soluble dimeric form of a receptor protein tyrosine kinase (like ROS). An antibody fragment that binds to the soluble dimeric form of the RTK used for screening is identified as a candidate molecule for blocking constitutive activation of the target RTK in a cell. See European Patent No. EP1423428, Borges et al., supra.

ROS-binding targeted antibodies identified in screening of antibody libraries as describe above may then be further screened for their ability to block the activity of ROS, both in vitro kinase assay and in vivo in cell lines and/or tumors. ROS inhibition may be confirmed, for example, by examining the ability of such antibody therapeutic to inhibit ROS kinase activity, but not other kinase activity, in a panel of kinases, and/or by examining the inhibition of ROS activity in a biological sample comprising cancer cells, as described above. Methods for screening such compounds for ROS kinase inhibition are further described above.

Indirect Inhibitors.

ROS-inhibiting compounds useful in the practice of the disclosed methods may also be compounds that indirectly inhibit ROS activity by inhibiting the activity of proteins or molecules other than ROS kinase itself. Such inhibiting therapeutics may be targeted inhibitors that modulate the activity of key regulatory kinases that phosphorylate or de-phosphorylate (and hence activate or deactivate) ROS itself, or interfere with binding of ligands. As with other receptor tyrosine kinases, ROS regulates downstream signaling through a network of adaptor proteins and downstream kinases. As a result, induction of cell growth and survival by ROS activity may be inhibited by targeting these interacting or downstream proteins.

ROS kinase activity may also be indirectly inhibited by using a compound that inhibits the binding of an activating molecule necessary for ROS to adopt its active conformation. For example, the production and use of anti-PDGF antibodies has been described. See U.S. Patent Publication No. 20030219839, "Anti-PDGF Antibodies and Methods for Producing Engineered Antibodies," Bowdish et al. Inhibition of ligand (PDGF) binding to the receptor directly down-regulates the receptor activity.

Indirect inhibitors of ROS activity may be rationally designed using X-ray crystallographic or computer modeling of ROS three dimensional structure, or may found by high throughput screening of compound libraries for inhibition of key upstream regulatory enzymes and/or necessary binding molecules, which results in inhibition of ROS kinase activity. Such approaches are well known in the art, and have been described. ROS inhibition by such therapeutics may be confirmed, for example, by examining the ability of the compound to inhibit ROS activity, but not other kinase activity, in a panel of kinases, and/or by examining the inhibition of ROS activity in a biological sample comprising cancer cells, e.g. NSCLC cells, as described above. Methods for identifying compounds that inhibit a cancer characterized by a CD74-ROS translocation and/or fusion polypeptide, and/or truncated ROS polynucleotide and/or polypeptide, are further described below.

Anti-Sense and/or Transcription Inhibitors.

ROS inhibiting therapeutics may also comprise anti-sense and/or transcription inhibiting compounds that inhibit ROS kinase activity by blocking transcription of the gene encoding ROS and/or the CD74-ROS fusion gene. The inhibition of various receptor kinases, including VEGFR, EGFR, and IGFR, and FGFR, by antisense therapeutics for the treatment of cancer has been described. See, e.g., U.S. Pat. Nos. 6,734,017; 6,710,174, 6,617,162; 6,340,674; 5,783,683; 5,610,288.

Antisense oligonucleotides may be designed, constructed, and employed as therapeutic agents against target genes in accordance with known techniques. See, e.g. Cohen, *J., Trends in Pharmacol. Sci.* 10(11): 435-437 (1989); Marcus-Sekura, *Anal. Biochem.* 172: 289-295 (1988); Weintraub, H., *Sci. AM.* pp. 40-46 (1990); Van Der Krol et al., *BioTechniques* 6(10): 958-976 (1988); Skorski et al., *Proc. Natl. Acad. Sci. USA* (1994) 91: 4504-4508. Inhibition of human carcinoma growth in vivo using an antisense RNA inhibitor of EGFR has recently been described. See U.S. Patent Publication No. 20040047847, "Inhibition of Human Squamous Cell Carcinoma Growth In vivo by Epidermal Growth Factor Receptor Antisense RNA Transcribed from a Pol III Promoter," Mar. 11, 2004, He et al. Similarly, a ROS-inhibiting therapeutic comprising at least one antisense oligonucleotide against a mammalian ROS gene (see FIG. 4 (SEQ ID NO: 8) or CD74-ROS fusion polynucleotide or truncated ROS polynucleotide (see FIG. 2 (SEQ ID NOs: 2) or truncated may be prepared according to methods described above. Pharmaceutical compositions comprising ROS-inhibiting antisense compounds may be prepared and administered as further described below.

Small Interfering RNA.

Small interfering RNA molecule (siRNA) compositions, which inhibit translation, and hence activity, of ROS through the process of RNA interference, may also be desirably employed in the methods of the invention. RNA interference, and the selective silencing of target protein expression by introduction of exogenous small double-stranded RNA molecules comprising sequence complimentary to mRNA encoding the target protein, has been well described. See, e.g. U.S. Patent Publication No. 20040038921, "Composition and Method for Inhibiting Expression of a Target Gene," Feb. 26, 2004, Kreutzer et al.; U.S. Patent Publication No. 20020086356, "RNA Sequence-Specific Mediators of RNA Interference," Jun. 12, 2003, Tuschl et al.; U.S. Patent Publication 20040229266, "RNA Interference Mediating Small RNA Molecules," Nov. 18, 2004, Tuschl et. al.

For example, as described in Example 3, siRNA-mediated silencing of expression of the CD74-ROS fusion protein may be effected in a human NSCLC cell line expressing the fusion protein.

Double-stranded RNA molecules (dsRNA) have been shown to block gene expression in a highly conserved regulatory mechanism known as RNA interference (RNAi). Briefly, the RNAse III Dicer processes dsRNA into small interfering RNAs (siRNA) of approximately 22 nucleotides, which serve as guide sequences to induce target-specific mRNA cleavage by an RNA-induced silencing complex RISC (see Hammond et al., *Nature* (2000) 404: 293-296). RNAi involves a catalytic-type reaction whereby new siRNAs are generated through successive cleavage of longer dsRNA. Thus, unlike antisense, RNAi degrades target RNA in a non-stoichiometric manner. When administered to a cell or organism, exogenous dsRNA has been shown to direct the sequence-specific degradation of endogenous messenger RNA (mRNA) through RNAi.

A wide variety of target-specific siRNA products, including vectors and systems for their expression and use in mammalian cells, are now commercially available. See, e.g. Promega, Inc. (www.promega.com); Dharmacon, Inc. (www.dharmacon.com). Detailed technical manuals on the design, construction, and use of dsRNA for RNAi are available. See, e.g. Dharmacon's "RNAi Technical Reference & Application Guide"; Promega's "RNAi: A Guide to Gene Silencing." ROS-inhibiting siRNA products are also commercially available, and may be suitably employed in the method of the invention. See, e.g. Dharmacon, Inc., Lafayette, Colo. (Cat Nos. M-003162-03, MU-003162-03, D-003162-07 thru-10 (siGENOME™ SMARTselection and SMARTpool® siRNAs).

It has recently been established that small dsRNA less than 49 nucleotides in length, and preferably 19-25 nucleotides, comprising at least one sequence that is substantially identical to part of a target mRNA sequence, and which dsRNA optimally has at least one overhang of 1-4 nucleotides at an end, are most effective in mediating RNAi in mammals. See U.S. Patent Publication No. 20040038921, Kreutzer et al., supra; U.S. Patent Publication No. 20040229266, Tuschl et al., supra. The construction of such dsRNA, and their use in pharmaceutical preparations to silence expression of a target protein, in vivo, are described in detail in such publications.

If the sequence of the gene to be targeted in a mammal is known, 21-23 nt RNAs, for example, can be produced and tested for their ability to mediate RNAi in a mammalian cell, such as a human or other primate cell. Those 21-23 nt RNA molecules shown to mediate RNAi can be tested, if desired, in an appropriate animal model to further assess their in vivo effectiveness. Target sites that are known, for example target sites determined to be effective target sites based on studies with other nucleic acid molecules, for example ribozymes or antisense, or those targets known to be associated with a disease or condition such as those sites containing mutations or deletions, can be used to design siRNA molecules targeting those sites as well.

Alternatively, the sequences of effective dsRNA can be rationally designed/predicted screening the target mRNA of interest for target sites, for example by using a computer folding algorithm. The target sequence can be parsed in silico into a list of all fragments or subsequences of a particular length, for example 23 nucleotide fragments, using a custom Perl script or commercial sequence analysis programs such as Oligo, MacVector, or the GCG Wisconsin Package.

Various parameters can be used to determine which sites are the most suitable target sites within the target RNA sequence. These parameters include but are not limited to secondary or tertiary RNA structure, the nucleotide base composition of the target sequence, the degree of homology between various regions of the target sequence, or the relative position of the target sequence within the RNA transcript. Based on these determinations, any number of target sites within the RNA transcript can be chosen to screen siRNA molecules for efficacy, for example by using in vitro RNA cleavage assays, cell culture, or animal models. See, e.g., U.S. Patent Publication No. 20030170891, Sep. 11, 2003, McSwiggen J. An algorithm for identifying and selecting RNAi target sites has also recently been described. See U.S. Patent Publication No. 20040236517, "Selection of Target Sites for Antisense Attack of RNA," Nov. 25, 2004, Drlica et al.

Commonly used gene transfer techniques include calcium phosphate, DEAE-dextran, electroporation and microinjection and viral methods (Graham et al. (1973) *Virol.* 52: 456; McCutchan et al., (1968), *J. Natl. Cancer Inst.* 41: 351; Chu et al. (1987), *Nucl. Acids Res.* 15: 1311; Fraley et al. (1980), *J. Biol. Chem.* 255: 0431; Capecchi (1980), *Cell* 22: 479). DNA may also be introduced into cells using cationic liposomes (Feigner et al. (1987), *Proc. Natl. Acad. Sci. USA* 84: 7413). Commercially available cationic lipid formulations include Tfx 50 (Promega) or Lipofectamin 200 (Life Technologies). Alternatively, viral vectors may be employed to deliver dsRNA to a cell and mediate RNAi. See U.S. Patent Publication No. 20040023390, "siRNA-mediated Gene Silencing with Viral Vectors," Feb. 4, 2004, Davidson et al.

Transfection and vector/expression systems for RNAi in mammalian cells are commercially available and have been well described. See, e.g. Dharmacon, Inc., DharmaFECT™ system; Promega, Inc., siSTRIKE™ U6 Hairpin system; see also Gou et al. (2003) *FEBS.* 548, 113-118; Sui, G. et al. A DNA vector-based RNAi technology to suppress gene expression in mammalian cells (2002) *Proc. Natl. Acad. Sci.* 99, 5515-5520; Yu et al. (2002) *Proc. Natl. Acad. Sci.* 99, 6047-6052; Paul, C. et al. (2002) *Nature Biotechnology* 19, 505-508; McManus et al. (2002) *RNA* 8, 842-850.

siRNA interference in a mammal using prepared dsRNA molecules may then be effected by administering a pharmaceutical preparation comprising the dsRNA to the mammal. The pharmaceutical composition is administered in a dosage sufficient to inhibit expression of the target gene. dsRNA can typically be administered at a dosage of less than 5 mg dsRNA per kilogram body weight per day, and is sufficient to inhibit or completely suppress expression of the target gene. In general a suitable dose of dsRNA will be in the range of 0.01 to 2.5 milligrams per kilogram body weight of the recipient per day, preferably in the range of 0.1 to 200 micrograms per kilogram body weight per day, more preferably in the range of 0.1 to 100 micrograms per kilogram body weight per day, even more preferably in the range of 1.0 to 50 micrograms per kilogram body weight per day, and most preferably in the range of 1.0 to 25 micrograms per kilogram body weight per day. A pharmaceutical composition comprising the dsRNA is administered once daily, or in multiple sub-doses, for example, using sustained release formulations well known in the art. The preparation and administration of such pharmaceutical compositions may be carried out accordingly to standard techniques, as further described below.

Such dsRNA may then be used to inhibit ROS expression and activity in a cancer, by preparing a pharmaceutical preparation comprising a therapeutically-effective amount of such dsRNA, as described above, and administering the preparation to a human subject having a cancer expressing CD74-ROS fusion protein or truncated ROS kinase polypeptide, for example, via direct injection to the tumor. The similar inhibition of other receptor tyrosine kinases, such as VEGFR and EGFR using siRNA inhibitors has recently been described. See U.S. Patent Publication No. 20040209832, Oct. 21, 2004, McSwiggen et al.; U.S. Patent Publication No. 20030170891, Sep. 11, 2003, McSwiggen; U.S. Patent Publication No. 20040175703, Sep. 9, 2004, Kreutzer et al.

Therapeutic Compositions; Administration.

ROS kinase-inhibiting therapeutic compositions useful in the practice of the methods of the invention may be administered to a mammal by any means known in the art including, but not limited to oral or peritoneal routes, including intravenous, intramuscular, intraperitoneal, subcutaneous, transdermal, airway (aerosol), rectal, vaginal and topical (including buccal and sublingual) administration.

For oral administration, a ROS-inhibiting therapeutic will generally be provided in the form of tablets or capsules, as a powder or granules, or as an aqueous solution or suspension. Tablets for oral use may include the active ingredients mixed with pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredients is mixed with water or an oil such as peanut oil, liquid paraffin or olive oil. For intramuscular, intraperitoneal, subcutaneous and intravenous use, the pharmaceutical compositions of the invention will generally be provided in sterile aqueous solutions or suspensions, buffered to an appropriate pH and isotonicity. Suitable aqueous vehicles include Ringer's solution and isotonic sodium chloride. The carrier may consists exclusively of an aqueous buffer ("exclusively" means no auxiliary agents or encapsulating substances are present which might affect or mediate uptake of the ROS-inhibiting therapeutic). Such substances include, for example, micellar structures, such as liposomes or capsids, as described below. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

ROS kinase-inhibiting therapeutic compositions may also include encapsulated formulations to protect the therapeutic (e.g. a dsRNA compound) against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811; PCT publication WO 91/06309; and European patent publication EP-A-43075. An encapsulated formulation may comprise a viral coat protein. The viral coat protein may be derived from or associated with a virus, such as a polyoma virus, or it may be partially or entirely artificial. For example, the coat protein may be a Virus Protein 1 and/or Virus Protein 2 of the polyoma virus, or a derivative thereof.

ROS-inhibiting compositions can also comprise a delivery vehicle, including liposomes, for administration to a subject, carriers and diluents and their salts, and/or can be present in pharmaceutically acceptable formulations. For example, methods for the delivery of nucleic acid molecules are described in Akhtar et al., 1992, *Trends Cell Bio.*, 2, 139; DELIVERY STRATEGIES FOR ANTISENSE OLIGONUCLEOTIDE THERAPEUTICS, ed. Akbtar, 1995, Maurer et al., 1999, *Mol. Membr. Biol.*, 16, 129-140; Hofland and Huang, 1999, *Handb. Exp. Pharmacol.*, 137, 165-192; and Lee et al., 2000, *ACS Symp. Ser.*, 752, 184-192. Beigelman et al., U.S. Pat. No. 6,395,713 and Sullivan et al., PCT WO 94/02595 further describe the general methods for delivery of nucleic acid molecules. These protocols can be utilized for the delivery of virtually any nucleic acid molecule.

ROS-inhibiting therapeutics can be administered to a mammalian tumor by a variety of methods known to those of skill in the art, including, but not restricted to, encapsulation in liposomes, by iontophoresis, or by incorporation into other vehicles, such as hydrogels, cyclodextrins, biodegradable nanocapsules, and bioadhesive microspheres, or by proteinaceous vectors (O'Hare and Normand, International PCT Publication No. WO 00/53722). Alternatively, the therapeutic/vehicle combination is locally delivered by direct injection or by use of an infusion pump. Direct injection of the composition, whether subcutaneous, intramuscular, or intradermal, can take place using standard needle and syringe methodologies, or by needle-free technologies such as those described in Conry et al., 1999, *Clin. Cancer Res.*, 5, 2330-2337 and Barry et al., International PCT Publication No. WO 99/3 1262.

Pharmaceutically acceptable formulations of ROS kinase-inhibitory therapeutics include salts of the above described compounds, e.g., acid addition salts, for example, salts of hydrochloric, hydrobromic, acetic acid, and benzene sulfonic acid. A pharmacological composition or formulation refers to a composition or formulation in a form suitable for administration, e.g., systemic administration, into a cell or patient, including for example a human. Suitable forms, in part, depend upon the use or the route of entry, for example oral, transdermal, or by injection. Such forms should not prevent the composition or formulation from reaching a target cell. For example, pharmacological compositions injected into the blood stream should be soluble. Other factors are known in the art, and include considerations such as toxicity and forms that prevent the composition or formulation from exerting its effect.

Administration routes that lead to systemic absorption (i.e. systemic absorption or accumulation of drugs in the blood stream followed by distribution throughout the entire body), are desirable and include, without limitation: intravenous, subcutaneous, intraperitoneal, inhalation, oral, intrapulmonary and intramuscular. Each of these administration routes exposes the ROS-inhibiting therapeutic to an accessible diseased tissue or tumor. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation that can facilitate the association of drug with the surface of cells, such as, lymphocytes and macrophages is also useful. This approach can provide enhanced delivery of the drug to target cells by taking advantage of the specificity of macrophage and lymphocyte immune recognition of abnormal cells, such as cancer cells.

By "pharmaceutically acceptable formulation" is meant, a composition or formulation that allows for the effective distribution of the nucleic acid molecules of the instant invention in the physical location most suitable for their desired activity. Nonlimiting examples of agents suitable for formulation with the nucleic acid molecules of the instant invention include: P-glycoprotein inhibitors (such as Pluronic P85), which can enhance entry of drugs into the CNS (Jolliet-Riant and Tillement, 1999, *Fundam. Clin. Pharmacol.*, 13, 16-26); biodegradable polymers, such as poly (DL-lactide-coglycolide) microspheres for sustained release delivery after intracerebral implantation (Emerich et al, 1999, *Cell Transplant*, 8, 47-58) (Alkermes, Inc. Cambridge, Mass.); and loaded nanoparticles, such as those made of polybutylcyanoacrylate, which can deliver drugs across the blood brain barrier and can alter neuronal uptake mechanisms (Prog Neuro-psychopharmacol Biol Psychiatry, 23, 941-949, 1999). Other non-limiting examples of delivery strategies for the ROS-inhibiting compounds useful in the method of the invention include material described in Boado et al., 1998, *J. Pharm. Sci.*, 87, 1308-1315; Tyler et al., 1999, *FEBS Lett.*, 421, 280-284; Pardridge et al., 1995, *PNAS USA.*, 92, 5592-5596; Boado, 1995, *Adv. Drug Delivery Rev.*, 15, 73-107; Aldrian-Herrada et al., 1998, *Nucleic Acids Res.*, 26, 4910-4916; and Tyler et al., 1999, *PNAS USA.*, 96, 7053-7058.

Therapeutic compositions comprising surface-modified liposomes containing poly (ethylene glycol) lipids (PEG-modified, or long-circulating liposomes or stealth liposomes)

may also be suitably employed in the methods of the invention. These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. *Chem. Rev.* 1995, 95, 2601-2627; Ishiwata et al., *Chem. Pharm. Bull.* 1995, 43, 1005-1011). Such liposomes have been shown to accumulate selectively in tumors, presumably by extravasation and capture in the neovascularized target tissues (Lasic et al., *Science* 1995, 267, 1275-1276; Oku et al., 1995, *Biochim. Biophys. Acta,* 1238, 86-90). The long-circulating liposomes enhance the pharmacokinetics and pharmacodynamics of DNA and RNA, particularly compared to conventional cationic liposomes which are known to accumulate in tissues of the MPS (Liu et al., *J. Biol. Chem.* 1995, 42, 24864-24870; Choi et al., International PCT Publication No. WO 96/10391; Ansell et al., International PCT Publication No. WO 96/10390; Holland et al., International PCT Publication No. WO 96/10392). Long-circulating liposomes are also likely to protect drugs from nuclease degradation to a greater extent compared to cationic liposomes, based on their ability to avoid accumulation in metabolically aggressive MPS tissues such as the liver and spleen.

Therapeutic compositions may include a pharmaceutically effective amount of the desired compounds in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985). For example, preservatives, stabilizers, dyes and flavoring agents can be provided. These include sodium benzoate, sorbic acid and esters of p-hydroxybenzoic acid. In addition, antioxidants and suspending agents can be used.

A pharmaceutically effective dose is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors that those skilled in the medical arts will recognize. Generally, an amount between 0.1 mg/kg and 100 mg/kg body weight/day of active ingredients is administered dependent upon potency of the negatively charged polymer.

Dosage levels of the order of from about 0.1 mg to about 140 mg per kilogram of body weight per day are useful in the treatment of the above-indicated conditions (about 0.5 mg to about 7 g per patient per day). The amount of active ingredient that can be combined with the carrier materials to produce a single dosage form varies depending upon the host treated and the particular mode of administration. Dosage unit forms generally contain between from about 1 mg to about 500 mg of an active ingredient. It is understood that the specific dose level for any particular patient depends upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water.

A ROS-inhibiting therapeutic useful in the practice of the invention may comprise a single compound as described above, or a combination of multiple compounds, whether in the same class of inhibitor (i.e. antibody inhibitor), or in different classes (i.e antibody inhibitors and small-molecule inhibitors). Such combination of compounds may increase the overall therapeutic effect in inhibiting the progression of a fusion protein-expressing cancer. For example, the therapeutic composition may a small molecule inhibitor, such as STI-571 (Gleevec®) alone, or in combination with other Gleevec® analogues targeting ROS activity and/or small molecule inhibitors of EGFR, such as Tarceva™ or Iressa™. The therapeutic composition may also comprise one or more non-specific chemotherapeutic agent in addition to one or more targeted inhibitors. Such combinations have recently been shown to provide a synergistic tumor killing effect in many cancers. The effectiveness of such combinations in inhibiting ROS activity and tumor growth in vivo can be assessed as described below.

Identification of Mutant ROS Kinase-Inhibiting Compounds.

The invention also provides, in part, a method for determining whether a compound inhibits the progression of a cancer characterized by a CD74-ROS translocation and/or fusion polypeptide, by determining whether the compound inhibits the activity of CD74-ROS fusion polypeptide in the cancer. In some preferred embodiments, inhibition of activity of ROS is determined by examining a biological sample comprising cells from bone marrow, blood, or a tumor. In another preferred embodiment, inhibition of activity of ROS is determined using at least one mutant ROS polynucleotide or polypeptide-specific reagent of the invention.

The tested compound may be any type of therapeutic or composition as described above. Methods for assessing the efficacy of a compound, both in vitro and in vivo, are well established and known in the art. For example, a composition may be tested for ability to inhibit ROS in vitro using a cell or cell extract in which ROS kinase is activated. A panel of compounds may be employed to test the specificity of the compound for ROS (as opposed to other targets, such as EGFR or PDGFR).

Another technique for drug screening which may be used provides for high throughput screening of compounds having suitable binding affinity to a protein of interest, as described in published PCT application WO84/03564. In this method, as applied to mutant ROS polypeptides, large numbers of different small test compounds are synthesized on a solid substrate, such as plastic pins or some other surface. The test compounds are reacted with mutant ROS polypeptide, or fragments thereof, and washed. Bound mutant polypeptide (e.g. CD74-ROS fusion polypeptide) is then detected by methods well known in the art. Purified mutant ROS polypeptide can also be coated directly onto plates for use in the aforementioned drug screening techniques. Alternatively, non-neutralizing antibodies can be used to capture the peptide and immobilize it on a solid support.

A compound found to be an effective inhibitor of ROS activity in vitro may then be examined for its ability to inhibit the progression of a cancer expressing CD74-ROS fusion polypeptide, in vivo, using, for example, mammalian xenografts harboring human NSCLC tumors that are driven by CD74-ROS fusion protein. In this procedure, cell lines known to be driven by CD74-ROS fusion protein are placed subcutaneously in the mouse. The cells then grow into a tumor mass that may be visually monitored. The mouse may then be treated with the drug. The effect of the drug treatment on tumor size may be externally observed. The mouse is then sacrificed and the tumor removed for analysis by IHC and Western blot. Similarly, mammalian bone marrow transplants may be prepared, by standard methods, to examine drug response in hematological tumors expressing a mutant ROS kinase. In this way, the effects of the drug may be observed in a biological setting most closely resembling a patient. The drug's ability to alter signaling in the tumor cells or surrounding stromal cells may be determined by analysis with phosphorylation-specific antibodies. The drug's effectiveness in inducing cell death or inhibition of cell proliferation may also be observed by analysis with apoptosis specific markers such as cleaved caspase 3 and cleaved PARP.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred.

The teachings of all references cited above and below are hereby incorporated herein by reference. The following Examples are provided only to further illustrate the invention, and are not intended to limit its scope, except as provided in the claims appended hereto. The present invention encompasses modifications and variations of the methods taught herein which would be obvious to one of ordinary skill in the art.

Example 1

Identification of ROS Kinase Activity from NSCLC Patients by Global Phosphopeptide Profiling The global phosphorylation profile of kinase activation in several human NSCLC patients, including CS042, were examined using a recently described and powerful technique for the isolation and mass spectrometric characterization of modified peptides from complex mixtures (the "IAP" technique, see Rush et al., supra). The IAP technique was performed using a phosphotyrosine-specific antibody (Cell Signaling Technology, Inc., Beverly, Mass., 2003/04 Cat. #9411) to isolate, and subsequently characterize, phosphotyrosine-containing peptides from extracts of the NSCLC cell lines.

Specifically, the IAP approach was employed go facilitate the identification of activated tyrosine kinases in the NSCLC patients, in order to identify novel drivers of this disease.

Phosphopeptide Immunoprecipitation.

A total of 0.5 g tumor tissue was homogenized and lysed in urea lysis buffer (20 mM HEPES pH 8.0, 9M urea, 1 mM sodium vanadate, 2.5 mM sodium pyrophosphate, 1 mM beta-glycerophosphate) at $1.25\times10^8$ cells/ml and sonicated. Sonicated lysates were cleared by centrifugation at 20,000×g, and proteins were reduced and alkylated as described previously (see Rush et al., *Nat. Biotechnol.* 23(1): 94-101 (2005)). Samples were diluted with 20 mM HEPES pH 8.0 to a final urea concentration of 2M. Trypsin (1 mg/ml in 0.001 M HCl) was added to the clarified lysate at 1:100 v/v. Samples were digested overnight at room temperature.

Following digestion, lysates were acidified to a final concentration of 1% TFA. Peptide purification was carried out using Sep-Pak $C_{18}$ columns as described previously (see Rush et al., supra.). Following purification, all elutions (8%, 12%, 15%, 18%, 22%, 25%, 30%, 35% and 40% acetonitrile in 0.1% TFA) were combined and lyophilized. Dried peptides were resuspended in 1.4 ml MOPS buffer (50 mM MOPS/NaOH pH 7.2, 10 mM $Na_2HPO_4$, 50 mM NaCl) and insoluble material removed by centrifugation at 12,000×g for 10 minutes.

The phosphotyrosine monoclonal antibody P-Tyr-100 (Cell Signaling Technology) from ascites fluid was coupled non-covalently to protein G agarose beads (Roche) at 4 mg/ml beads overnight at 4° C. After coupling, antibody-resin was washed twice with PBS and three times with MOPS buffer. Immobilized antibody (40 μl, 160 μg) was added as a 1:1 slurry in MOPS IP buffer to the solubilized peptide fraction, and the mixture was incubated overnight at 4° C. The immobilized antibody beads were washed three times with MOPS buffer and twice with $ddH_2O$. Peptides were eluted twice from beads by incubation with 40 μl of 0.1% TFA for 20 minutes each, and the fractions were combined.

Analysis by LC-MS/MS Mass Spectrometry.

Peptides in the IP eluate (40 μl) were concentrated and separated from eluted antibody using Stop and Go extraction tips (StageTips) (see Rappsilber et al., *Anal. Chem.,* 75(3): 663-70 (2003)). Peptides were eluted from the microcolumns with 1 μl of 60% MeCN, 0.1% TFA into 7.6 μl of 0.4% acetic acid/0.005% heptafluorobutyric acid (HFBA). The sample was loaded onto a 10 cm×75 μm PicoFrit capillary column (New Objective) packed with Magic C18 AQ reversed-phase resin (Michrom Bioresources) using a Famos autosampler with an inert sample injection valve (Dionex). The column was developed with a 45-min linear gradient of acetonitrile in 0.4% acetic acid, 0.005% HFBA delivered at 280 nl/min (Ultimate, Dionex).

Tandem mass spectra were collected in a data-dependent manner with an LCQ Deca XP Plus ion trap mass spectrometer (ThermoFinnigan), using a top-four method, a dynamic exclusion repeat count of 1, and a repeat duration of 0.5 min.

Database Analysis & Assignments.

MS/MS spectra were evaluated using TurboSequest (ThermoFinnigan) (in the Sequest Browser package (v. 27, rev. 12) supplied as part of BioWorks 3.0). Individual MS/MS spectra were extracted from the raw data file using the Sequest Browser program CreateDta, with the following settings: bottom MW, 700; top MW, 4,500; minimum number of ions, 20; minimum TIC, $4\times10^5$; and precursor charge state, unspecified. Spectra were extracted from the beginning of the raw data file before sample injection to the end of the eluting gradient. The IonQuest and VuDta programs were not used to further select MS/MS spectra for Sequest analysis. MS/MS spectra were evaluated with the following TurboSequest parameters: peptide mass tolerance, 2.5; fragment ion tolerance, 0.0; maximum number of differential amino acids per modification, 4; mass type parent, average; mass type fragment, average; maximum number of internal cleavage sites, 10; neutral losses of water and ammonia from b and y ions were considered in the correlation analysis. Proteolytic enzyme was specified except for spectra collected from elastase digests.

Searches were done against the NCBI human database released on Aug. 24, 2004 containing 27,175 proteins allowing oxidized methionine (M+16) and phosphorylation (Y+80) as dynamic modifications.

In proteomics research, it is desirable to validate protein identifications based solely on the observation of a single peptide in one experimental result, in order to indicate that the protein is, in fact, present in a sample. This has led to the development of statistical methods for validating peptide assignments, which are not yet universally accepted, and guidelines for the publication of protein and peptide identification results (see Can et al., *Mol. Cell. Proteomics* 3: 531-533 (2004)), which were followed in this Example. However, because the immunoaffinity strategy separates phosphorylated peptides from unphosphorylated peptides, observing just one phosphopeptide from a protein is a common result, since many phosphorylated proteins have only one tyrosine-phosphorylated site.

For this reason, it is appropriate to use additional criteria to validate phosphopeptide assignments. Assignments are likely to be correct if any of these additional criteria are met: (i) the same sequence is assigned to co-eluting ions with different charge states, since the MS/MS spectrum changes markedly with charge state; (ii) the site is found in more than one peptide sequence context due to sequence overlaps from incomplete proteolysis or use of proteases other than trypsin; (iii) the site is found in more than one peptide sequence context due to homologous but not identical protein isoforms; (iv) the site is found in more than one peptide sequence context due to homologous but not identical proteins among species; and (v) sites validated by MS/MS analysis of synthetic phosphopeptides corresponding to assigned sequences, since the ion trap mass spectrometer produces highly reproducible MS/MS spectra. The last criterion is routinely employed to confirm novel site assignments of particular interest.

All spectra and all sequence assignments made by Sequest were imported into a relational database. Assigned sequences were accepted or rejected following a conservative, two-step process. In the first step, a subset of high-scoring sequence assignments was selected by filtering for XCorr values of at least 1.5 for a charge state of +1, 2.2 for +2, and 3.3 for +3, allowing a maximum RSp value of 10. Assignments in this subset were rejected if any of the following criteria were satisfied: (i) the spectrum contained at least one major peak (at least 10% as intense as the most intense ion in the spectrum) that could not be mapped to the assigned sequence as an a, b, or y ion, as an ion arising from neutral-loss of water or ammonia from a b or y ion, or as a multiply protonated ion; (ii) the spectrum did not contain a series of b or y ions equivalent to at least six uninterrupted residues; or (iii) the sequence was not observed at least five times in all the studies we have conducted (except for overlapping sequences due to incomplete proteolysis or use of proteases other than trypsin). In the second step, assignments with below-threshold scores were accepted if the low-scoring spectrum showed a high degree of similarity to a high-scoring spectrum collected in another study, which simulates a true reference library-searching strategy. All spectra supporting the final list of assigned sequences (not shown here) were reviewed by at least three scientists to establish their credibility.

The foregoing IAP analysis identified many tyrosine phosphorylated proteins, the majority of which are novel. Among tyrosine phosphorylated kinases were several of those detected are not normally detected by MS analysis in other NSCLC cell lines (unpublished data), including ROS kinase.

Example 2

Isolation & Sequencing of CD74-ROS Fusion Gene

Given the presence of the activated form of ROS kinase detected in a NSCLC patient, 5' rapid amplification of cDNA ends on the sequence encoding the kinase domain of ROS was conducted in order to determine whether a chimeric ROS transcript was present.

Rapid Amplification of Complementary DNA Ends

RNeasy Mini Kit (Qiagen) was used to extract RNA from C5045 cell line. DNA was extracted with the use of DNeasy Tissue Kit (Qiagen). Rapid amplification of cDNA ends was performed with the use of 5' RACE system (Invitrogen) with primers ROS-GSP1 for cDNA synthesis and ROS-GSP2 and ROS-GSP3 for a nested PCR reaction.

PCR Assay

For RT-PCR, first-strand cDNA was synthesized from 2.5 μg of total RNA with the use of SuperScript™ III first-strand synthesis system (Invitrogen) with oligo $(dT)_{20}$. Then, the CD74-ROS fusion gene was amplified with the use of primer pairs CD74-F1 and ROS-GSP3:

```
ROS-GSP1:
ACCCTTCTCGGTTCTTCGTTTCCA     (SEQ ID NO: 7)

ROS-GSP2:
GCAGCTCAGCCAACTCTTTGTCTT     (SEQ ID NO: 8)

ROS-GSP3:
TGCCAGACAAAGGTCAGTGGGATT     (SEQ ID NO: 9)

CD74-F1:
GCAGAATGCCACCAAGTATGGCAA     (SEQ ID NO: 10)
```

Sequence analysis of the resultant product revealed that the c-terminal of ROS was fused to CD74 gene N-terminus (see FIG. 1, panel B and C). The CD74-ROS fusion gene was in-frame and fused the first 208 amino acids of CD74 to the last 495 amino acids of ROS (see FIG. 1, panel B), resulting in a fusion protein. CD74 was located on chromosome 5q32, whereas ROS was on chromosome 6q22. Thus, the fusion gene was created by t(5; 6)(q32; q22).

The fusion of CD74 and ROS was confirmed by reverse-transcriptase-PCR on RNA. See FIG. 5

Example 3

Detection of CD74-ROS Fusion Protein Expression in a Human Cancer Sample Using FISH Assay The presence of the CD74-ROS fusion protein in human NSCLC tumor samples was detected using a fluorescence in situ hybridization (FISH) assay, as previously described. See, e.g., Verma et al. HUMAN CHROMOSOMES: A MANUAL OF BASIC TECHNIQUES, Pergamon Press, New York, N.Y. (1988). Over 200 paraffin-embedded human NSCLC tumor samples were examined.

For analyzing rearrangements involving ROS, a dual color break-apart probe was designed. A proximal probe (BAC clone RP1-179P9) and two distal probes (BAC clone RP11-323017, RP1-94G16) were labeled with Spectrum Orange dUTP or Spectrum Green dUTP, respectively. Labeling of the probes by nick translation and interphase FISH using FFPE tissue sections were done according to the manufactures instructions (Vysis) with the following modifications. In brief, paraffin embedded tissue sections were re-hydrated and subjected to microwave antigen retrieval in 0.01M Citrate buffer (pH 6.0) for 11 minutes. Sections were digested with Protease (4 mg/ml Pepsin, 2000-3000 U/mg) for 25 minutes at 37° C., dehydrated and hybridized with the FISH probe set at 37° C. for 18 hours. After washing, 4',6-diamidino-2-phenylindole (DAPI; mg/ml) in Vectashield mounting medium (Vector Laboratories, Burlingame, Calif.) was applied for nuclear counterstaining.

The ROS rearrangement probe contains two differently labeled probes on opposite sides of the breakpoint of the ROS gene in the wild type sequence (see FIG. 4B and FIG. 1). When hybridized, the native ROS region will appear as an orange/green fusion signal, while rearrangement at this locus (as occurs in the CD74-ROS fusion protein) will result in separate orange and green signals.

The FISH analysis revealed a low incidence of this ROS mutation in the sample population studied. Two out of 123 tumors or 1.6% of tumors contained the fusion mutation. However, given the high incidence of NSCLC worldwide (over 151,00 new cases in the U.S. annually, alone), there are expected to be a significant number of patients that harbor this mutant ROS, which patients may benefit from a ROS-inhibiting therapeutic regime.

Example 4

Detection of Mutant ROS Kinase Expression in a Human Cancer Sample Using PCR Assay The presence of truncated ROS kinase and/or CD74-ROS fusion protein in a human cancer sample may be detected using either genomic or reverse transcriptase (RT) polymerase chain reaction (PCR), previously described. See, e.g., Cools et al., *N. Engl. J. Med.* 348: 1201-1214 (2003).

Briefly and by way of example, tumor or pleural effusion samples may be obtained from a patient having NSCLC using standard techniques. PCR probes against truncated ROS kinase or CD74-ROS fusion protein are constructed. RNeasy Mini Kit (Qiagen) may be used to extract RNA from the tumor or pleural effusion samples. DNA may be extracted with the use of DNeasy Tissue Kit (Qiagen). For RT-PCR, first-strand cDNA is synthesized from, e.g., 2.5 μg of total RNA with the use, for example, of SuperScript™ III first-strand synthesis system (Invitrogen) with oligo $(dT)_{20}$. Then, the CD74-ROS fusion gene is amplified with the use of primer pairs, e.g. CD74-F1 and ROS-GSP3.

Such an analysis will identify a patient having a cancer characterized by expression of the truncated ROS kinase (and/or CD74-ROS fusion protein), which patient is a candidate for treatment using a ROS-inhibiting therapeutic.

What is claimed is:

1. An isolated cDNA comprising a nucleotide sequence at least 95% identical to a sequence selected from the group consisting of:

(a) a nucleotide sequence encoding a CD74-ROS fusion polypeptide comprising the amino acid sequence of SEQ ID NO: 1;

(b) a nucleotide sequence encoding a CD74-ROS fusion polypeptide, said nucleotide sequence comprising the nucleotide sequence of SEQ ID NO: 2;

(c) a nucleotide sequence encoding a CD74-ROS fusion polypeptide comprising residues 1-208 of SEQ ID NO: 3 and residues 1945-2222 of SEQ ID NO: 5;

(d) a nucleotide sequence comprising nucleotides 1-624 of SEQ ID NO: 4 and nucleotides 6032-6865 of SEQ ID NO: 6; and (e) a nucleotide sequence complementary to the full length of any of the nucleotide sequences of (a)-(d).

2. A method for detecting the presence of a CD74-ROS fusion polynucleotide in a cancer, said method comprising:

detecting the presence of a CD74-ROS fusion polynucleotide in a biological sample from a human patient having cancer, wherein said biological sample comprise cancer cells, and wherein said CD74-ROS fusion polynucleotide comprises a nucleotide sequence at least 95% identical to a sequence selected from the group consisting of:

(i) a nucleotide sequence encoding a CD74-ROS fusion polypeptide comprising the amino acid sequence of SEQ ID NO: 1;

(ii) a nucleotide sequence encoding a CD74-ROS fusion polypeptide, said nucleotide sequence comprising the nucleotide sequence of SEQ ID NO: 2;

(iii) a nucleotide sequence encoding a CD74-ROS fusion polypeptide comprising residues 1-208 of SEQ ID NO: 3 and residues 1945-2222 of SEQ ID NO: 5;

(iv) a nucleotide sequence comprising nucleotides 1-624 of SEQ ID NO: 4 nucleotides 6032-6865 of SEQ ID NO: 6; and (v) a nucleotide sequence complementary to the full length sequence of any of the nucleotide sequences of (i)-(iv);

wherein said detecting comprises performing a fluorescence in situ hybridization (FISH) assay, a polymerase chain reaction (PCR) assay, or nucleic acid sequencing.

3. The method of claim 2, wherein said cancer is lung cancer.

4. The method of claim 3, wherein said lung cancer is non-small cell lung carcinoma (NSCLC).

5. The method of claim 2, wherein the method is implemented in a format selected from the group consisting of fluorescence in situ hybridization (FISH) and polymerase chain reaction (PCR) assay.

6. The method of claim 2, wherein said detecting comprises nucleic acid sequencing.

7. The method of claim 2, wherein said polynucleotide is DNA.

8. The method of claim 2, wherein said polynucleotide is RNA.

9. The method of claim 2, wherein said biological sample is a tumor biopsy sample, a pleural effusion sample, or a blood sample.

10. The method of claim 2, wherein said CD74-ROS fusion polynucleotide comprises a nucleotide sequence at least 95% identical with a nucleotide sequence which encodes a CD74-ROS fusion polypeptide comprising the amino acid sequence of SEQ ID NO: 1.

11. The method of claim 10, wherein said CD74-ROS fusion polynucleotide comprises a nucleotide sequence which encodes a CD74-ROS fusion polypeptide comprising the amino acid sequence of SEQ ID NO: 1.

12. The method of claim 2, wherein said detecting comprises performing a FISH assay.

13. The method of claim 12, wherein said biological sample is a tumor biopsy sample, a pleural effusion sample, or a blood sample.

14. The method of claim 12, wherein said CD74-ROS fusion polynucleotide comprises a nucleotide sequence at least 95% identical with a nucleotide sequence which encodes a CD74-ROS fusion polypeptide comprising the amino acid sequence of SEQ ID NO: 1.

15. The method of claim 12, wherein said CD74-ROS fusion polynucleotide comprises a nucleotide sequence which encodes a CD74-ROS fusion polypeptide comprising the amino acid sequence of SEQ ID NO: 1.

16. A method, comprising:

performing a polynucleotide amplification reaction with polynucleotides from a biological sample of a human subject having cancer, said biological sample comprising cancer cells, wherein said amplification reaction utilizes a pair of primers, wherein (i) the first primer of the primer pair hybridizes under stringent conditions to a polynucleotide consisting of nucleotides 1-636 of SEQ ID NO: 4 or a complement thereof, and the second primer of the primer pair hybridizes under said stringent conditions to a polynucleotide consisting of nucleotides 5756-7368 of SEQ ID NO: 6 or a complement thereof, wherein said stringent conditions comprise overnight incubation at 42° C. in a solution comprising 50% formamide, 5×SSC, 50 mM sodium phosphate pH7.6, 5× Denhardt's solution, 10% dextran sulfate and 20 μg/ml denatured, sheared salmon sperm DNA, followed by washing in 0.1×SSC at 65° C., or (ii) the first primer of the primer pair is at least 95% identical to a fragment of a polynucleotide consisting of nucleotides 1-636 of SEQ ID NO: 4 or a complement thereof, and the second primer of the primer pair is at least 95% identical to a fragment of a polynucleotide consisting of nucleotides 5756-7368 of SEQ ID NO: 6 or a complement thereof, and detecting the presence or absence of an amplification product thereby determining the presence or absence of a CD74-ROS fusion polynucleotide in said sample.

17. The method of claim 16, wherein said polynucleotides are DNA.

18. The method of claim 16, wherein said polynucleotides are RNA.

19. The method of claim 16, wherein said biological sample is a tumor biopsy sample, a pleural effusion sample, or a blood sample.

20. The method of claim 16, wherein said cancer is lung cancer.

21. The method of claim 20, wherein said lung cancer is non-small cell lung carcinoma (NSCLC).

* * * * *

SEQUENCE LISTING

```
<160> NUMBER OF SEQ ID NOS: 13

<210> SEQ ID NO 1
<211> LENGTH: 703
<212> TYPE: PRT
<213> ORGANISM: Homo sapiens

<400> SEQUENCE: 1

Met His Arg Arg Arg Ser Arg Ser Cys Arg Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Ala Pro Glu Ser Lys Cys Ser Arg Gly Ala
        35                  40                  45

Leu Tyr Thr Gly Phe Ser Ile Leu Val Thr Leu Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Ser Gln Asn Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Leu Pro Gln Gly Pro Met
        115                 120                 125

Gln Asn Ala Thr Lys Tyr Gly Asn Met Thr Glu Asp His Val Met His
    130                 135                 140

Leu Leu Gln Asn Ala Asp Pro Leu Lys Val Tyr Pro Pro Leu Lys Gly
145                 150                 155                 160

Ser Phe Pro Glu Asn Leu Arg His Leu Lys Asn Thr Met Glu Thr Ile
                165                 170                 175

Asp Trp Lys Val Phe Glu Ser Trp Met His His Trp Leu Leu Phe Glu
            180                 185                 190

Met Ser Arg His Ser Leu Glu Gln Lys Pro Thr Asp Ala Pro Pro Lys
        195                 200                 205

Asp Asp Phe Trp Ile Pro Glu Thr Ser Phe Ile Leu Thr Ile Ile Val
    210                 215                 220

Gly Ile Phe Leu Val Val Thr Ile Pro Leu Thr Phe Val Trp His Arg
```

```
225                 230                 235                 240

Arg Leu Lys Asn Gln Lys Ser Ala Lys Glu Gly Val Thr Val Leu Ile
                245                 250                 255

Asn Glu Asp Lys Glu Leu Ala Glu Leu Arg Gly Leu Ala Ala Gly Val
            260                 265                 270

Gly Leu Ala Asn Ala Cys Tyr Ala Ile His Thr Leu Pro Thr Gln Glu
        275                 280                 285

Glu Ile Glu Asn Leu Pro Ala Phe Pro Arg Glu Lys Leu Thr Leu Arg
    290                 295                 300

Leu Leu Leu Gly Ser Gly Ala Phe Gly Glu Val Tyr Glu Gly Thr Ala
305                 310                 315                 320

Val Asp Ile Leu Gly Val Gly Ser Gly Glu Ile Lys Val Ala Val Lys
                325                 330                 335

Thr Leu Lys Lys Gly Ser Thr Asp Gln Glu Lys Ile Glu Phe Leu Lys
            340                 345                 350

Glu Ala His Leu Met Ser Lys Phe Asn His Pro Asn Ile Leu Lys Gln
        355                 360                 365

Leu Gly Val Cys Leu Leu Asn Glu Pro Gln Tyr Ile Ile Leu Glu Leu
    370                 375                 380

Met Glu Gly Gly Asp Leu Leu Thr Tyr Leu Arg Lys Ala Arg Met Ala
385                 390                 395                 400

Thr Phe Tyr Gly Pro Leu Leu Thr Leu Val Asp Leu Val Asp Leu Cys
                405                 410                 415

Val Asp Ile Ser Lys Gly Cys Val Tyr Leu Glu Arg Met His Phe Ile
            420                 425                 430

His Arg Asp Leu Ala Ala Arg Asn Cys Leu Val Ser Val Lys Asp Tyr
        435                 440                 445

Thr Ser Pro Arg Ile Val Lys Ile Gly Asp Phe Gly Leu Ala Arg Asp
    450                 455                 460

Ile Tyr Lys Asn Asp Tyr Tyr Arg Lys Arg Gly Glu Gly Leu Leu Pro
465                 470                 475                 480

Val Arg Trp Met Ala Pro Glu Ser Leu Met Asp Gly Ile Phe Thr Thr
                485                 490                 495

Gln Ser Asp Val Trp Ser Phe Gly Ile Leu Ile Trp Glu Ile Leu Thr
            500                 505                 510

Leu Gly His Gln Pro Tyr Pro Ala His Ser Asn Leu Asp Val Leu Asn
        515                 520                 525

Tyr Val Gln Thr Gly Gly Arg Leu Glu Pro Pro Arg Asn Cys Pro Asp
    530                 535                 540

Asp Leu Trp Asn Leu Met Thr Gln Cys Trp Ala Gln Glu Pro Asp Gln
545                 550                 555                 560

Arg Pro Thr Phe His Arg Ile Gln Asp Gln Leu Gln Leu Phe Arg Asn
                565                 570                 575

Phe Phe Leu Asn Ser Ile Tyr Lys Ser Arg Asp Glu Ala Asn Asn Ser
            580                 585                 590

Gly Val Ile Asn Glu Ser Phe Glu Gly Glu Asp Gly Asp Val Ile Cys
        595                 600                 605

Leu Asn Ser Asp Asp Ile Met Pro Val Ala Leu Met Glu Thr Lys Asn
    610                 615                 620

Arg Glu Gly Leu Asn Tyr Met Val Leu Ala Thr Glu Cys Gly Gln Gly
625                 630                 635                 640

Glu Glu Lys Ser Glu Gly Pro Leu Gly Ser Gln Glu Ser Glu Ser Cys
                645                 650                 655
```

```
Gly Leu Arg Lys Glu Glu Lys Glu Pro His Ala Asp Lys Asp Phe Cys
            660                 665                 670

Gln Glu Lys Gln Val Ala Tyr Cys Pro Ser Gly Lys Pro Glu Gly Leu
        675                 680                 685

Asn Tyr Ala Cys Leu Thr His Ser Gly Tyr Gly Asp Gly Ser Asp
    690                 695                 700


<210> SEQ ID NO 2
<211> LENGTH: 2112
<212> TYPE: DNA
<213> ORGANISM: Homo sapiens

<400> SEQUENCE: 2

atgcacagga ggagaagcag gagctgtcgg gaagatcaga agccagtcat ggatgaccag     60

cgcgacctta tctccaacaa tgagcaactg cccatgctgg gccggcgccc tggggccccg    120

gagagcaagt gcagccgcgg agccctgtac acaggctttt ccatcctggt gactctgctc    180

ctcgctggcc aggccaccac cgcctacttc ctgtaccagc agcagggccg gctggacaaa    240

ctgacagtca cctcccagaa cctgcagctg gagaacctgc gcatgaagct tcccaagcct    300

cccaagcctg tgagcaagat gcgcatggcc accccgctgc tgatgcaggc gctgcccatg    360

ggagccctgc cccaggggcc catgcagaat gccaccaagt atggcaacat gacagaggac    420

catgtgatgc acctgctcca gaatgctgac cccctgaagg tgtacccgcc actgaagggg    480

agcttcccgg agaacctgag acaccttaag aacaccatgg agaccataga ctggaaggtc    540

tttgagagct ggatgcacca ttggctcctg tttgaaatga gcaggcactc cttggagcaa    600

aagcccactg acgctccacc gaaagatgat tttggatac cagaaacaag tttcatactt    660

actattatag ttggaatatt tctggttgtt acaatcccac tgacctttgt ctggcataga    720

agattaaaga atcaaaaaag tgccaaggaa ggggtgacag tgcttataaa cgaagacaaa    780

gagttggctg agctgcgagg tctggcagcc ggagtaggcc tggctaatgc ctgctatgca    840

atacatactc ttccaaccca agaggagatt gaaaatcttc ctgccttccc tcgggaaaaa    900

ctgactctgc gtctcttgct gggaagtgga gcctttggag aagtgtatga aggaacagca    960

gtggacatct taggagttgg aagtggagaa atcaaagtag cagtgaagac tttgaagaag   1020

ggttccacag accaggagaa gattgaattc ctgaaggagg cacatctgat gagcaaattt   1080

aatcatccca acattctgaa gcagcttgga gtttgtctgc tgaatgaacc ccaatacatt   1140

atcctggaac tgatggaggg aggagacctt cttacttatt tgcgtaaagc ccggatggca   1200

acgttttatg gtcctttact caccttggtt gaccttgtag acctgtgtgt agatatttca   1260

aaaggctgtg tctacttgga acggatgcat ttcattcaca gggatctggc agctagaaat   1320

tgccttgttt ccgtgaaaga ctataccagt ccacggatag tgaagattgg agactttgga   1380

ctcgccagag acatctataa aaatgattac tatagaaaga gaggggaagg cctgctccca   1440

gttcggtgga tggctccaga aagtttgatg gatggaatct tcactactca atctgatgta   1500

tggtcttttg gaattctgat ttgggagatt ttaactcttg gtcatcagcc ttatccagct   1560

cattccaacc ttgatgtgtt aaactatgtg caaacaggag ggagactgga gccaccaaga   1620

aattgtcctg atgatctgtg gaatttaatg acccagtgct gggctcaaga acccgaccaa   1680

agacctactt ttcatagaat tcaggaccaa cttcagttat tcagaaattt tttcttaaat   1740

agcatttata agtccagaga tgaagcaaac aacagtggag tcataaatga aagctttgaa   1800

ggtgaagatg gcgatgtgat ttgtttgaat tcagatgaca ttatgccagt tgctttaatg   1860
```

```
gaaacgaaga accgagaagg gttaaactat atggtacttg ctacagaatg tggccaaggt   1920

gaagaaaagt ctgagggtcc tctaggctcc caggaatctg aatcttgtgg tctgaggaaa   1980

gaagagaagg aaccacatgc agacaaagat ttctgccaag aaaaacaagt ggcttactgc   2040

ccttctggca agcctgaagg cctgaactat gcctgtctca ctcacagtgg atatggagat   2100

gggtctgatt aa                                                       2112


<210> SEQ ID NO 3
<211> LENGTH: 296
<212> TYPE: PRT
<213> ORGANISM: Homo sapiens

<400> SEQUENCE: 3

Met His Arg Arg Arg Ser Arg Ser Cys Arg Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Ala Pro Glu Ser Lys Cys Ser Arg Gly Ala
        35                  40                  45

Leu Tyr Thr Gly Phe Ser Ile Leu Val Thr Leu Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Ser Gln Asn Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Leu Pro Gln Gly Pro Met
        115                 120                 125

Gln Asn Ala Thr Lys Tyr Gly Asn Met Thr Glu Asp His Val Met His
    130                 135                 140

Leu Leu Gln Asn Ala Asp Pro Leu Lys Val Tyr Pro Pro Leu Lys Gly
145                 150                 155                 160

Ser Phe Pro Glu Asn Leu Arg His Leu Lys Asn Thr Met Glu Thr Ile
                165                 170                 175

Asp Trp Lys Val Phe Glu Ser Trp Met His His Trp Leu Leu Phe Glu
            180                 185                 190

Met Ser Arg His Ser Leu Glu Gln Lys Pro Thr Asp Ala Pro Pro Lys
        195                 200                 205

Val Leu Thr Lys Cys Gln Glu Glu Val Ser His Ile Pro Ala Val His
    210                 215                 220

Pro Gly Ser Phe Arg Pro Lys Cys Asp Glu Asn Gly Asn Tyr Leu Pro
225                 230                 235                 240

Leu Gln Cys Tyr Gly Ser Ile Gly Tyr Cys Trp Cys Val Phe Pro Asn
                245                 250                 255

Gly Thr Glu Val Pro Asn Thr Arg Ser Arg Gly His His Asn Cys Ser
            260                 265                 270

Glu Ser Leu Glu Leu Glu Asp Pro Ser Ser Gly Leu Gly Val Thr Lys
        275                 280                 285

Gln Asp Leu Gly Pro Ala Pro Leu
    290                 295


<210> SEQ ID NO 4
<211> LENGTH: 899
```

```
<212> TYPE: DNA
<213> ORGANISM: Homo sapiens

<400> SEQUENCE: 4

cagggtccca gatgcacagg aggagaagca ggagctgtcg ggaagatcag aagccagtca      60

tggatgacca gcgcgacctt atctccaaca atgagcaact gcccatgctg ggccggcgcc     120

ctggggcccc ggagagcaag tgcagccgcg gagccctgta cacaggcttt tccatcctgg     180

tgactctgct cctcgctggc caggccacca ccgcctactt cctgtaccag cagcagggcc     240

ggctggacaa actgacagtc acctcccaga acctgcagct ggagaacctg cgcatgaagc     300

ttcccaagcc tcccaagcct gtgagcaaga tgcgcatggc caccccgctg ctgatgcagg     360

cgctgcccat gggagccctg ccccaggggc ccatgcagaa tgccaccaag tatggcaaca     420

tgacagagga ccatgtgatg cacctgctcc agaatgctga cccccctgaag gtgtacccgc     480

cactgaaggg gagcttcccg gagaacctga gacaccttaa gaacaccatg gagaccatag     540

actggaaggt ctttgagagc tggatgcacc attggctcct gtttgaaatg agcaggcact     600

ccttggagca aaagcccact gacgctccac cgaaagtact gaccaagtgc caggaagagg     660

tcagccacat ccctgctgtc cacccgggtt cattcaggcc caagtgcgac gagaacggca     720

actatctgcc actccagtgc tatgggagca tcggctactg ctggtgtgtc ttccccaacg     780

gcacggaggt ccccaacacc agaagccgcg ggcaccataa ctgcagtgag tcactggaac     840

tggaggaccc gtcttctggg ctgggtgtga ccaagcagga tctgggccca gctcctttg      899


<210> SEQ ID NO 5
<211> LENGTH: 2347
<212> TYPE: PRT
<213> ORGANISM: Homo sapiens

<400> SEQUENCE: 5

Met Lys Asn Ile Tyr Cys Leu Ile Pro Lys Leu Val Asn Phe Ala Thr
1               5                   10                  15

Leu Gly Cys Leu Trp Ile Ser Val Val Gln Cys Thr Val Leu Asn Ser
            20                  25                  30

Cys Leu Lys Ser Cys Val Thr Asn Leu Gly Gln Gln Leu Asp Leu Gly
        35                  40                  45

Thr Pro His Asn Leu Ser Glu Pro Cys Ile Gln Gly Cys His Phe Trp
    50                  55                  60

Asn Ser Val Asp Gln Lys Asn Cys Ala Leu Lys Cys Arg Glu Ser Cys
65                  70                  75                  80

Glu Val Gly Cys Ser Ser Ala Glu Gly Ala Tyr Glu Glu Glu Val Leu
                85                  90                  95

Glu Asn Ala Asp Leu Pro Thr Ala Pro Phe Ala Ser Ser Ile Gly Ser
            100                 105                 110

His Asn Met Thr Leu Arg Trp Lys Ser Ala Asn Phe Ser Gly Val Lys
        115                 120                 125

Tyr Ile Ile Gln Trp Lys Tyr Ala Gln Leu Leu Gly Ser Trp Thr Tyr
    130                 135                 140

Thr Lys Thr Val Ser Arg Pro Ser Tyr Val Val Lys Pro Leu His Pro
145                 150                 155                 160

Phe Thr Glu Tyr Ile Phe Arg Val Val Trp Ile Phe Thr Ala Gln Leu
                165                 170                 175

Gln Leu Tyr Ser Pro Pro Ser Pro Ser Tyr Arg Thr His Pro His Gly
            180                 185                 190
```

```
Val Pro Glu Thr Ala Pro Leu Ile Arg Asn Ile Glu Ser Ser Ser Pro
        195                 200                 205

Asp Thr Val Glu Val Ser Trp Asp Pro Pro Gln Phe Pro Gly Gly Pro
    210                 215                 220

Ile Leu Gly Tyr Asn Leu Arg Leu Ile Ser Lys Asn Gln Lys Leu Asp
225                 230                 235                 240

Ala Gly Thr Gln Arg Thr Ser Phe Gln Phe Tyr Ser Thr Leu Pro Asn
                245                 250                 255

Thr Ile Tyr Arg Phe Ser Ile Ala Ala Val Asn Glu Val Gly Glu Gly
            260                 265                 270

Pro Glu Ala Glu Ser Ser Ile Thr Thr Ser Ser Ser Ala Val Gln Gln
        275                 280                 285

Glu Glu Gln Trp Leu Phe Leu Ser Arg Lys Thr Ser Leu Arg Lys Arg
    290                 295                 300

Ser Leu Lys His Leu Val Asp Glu Ala His Cys Leu Arg Leu Asp Ala
305                 310                 315                 320

Ile Tyr His Asn Ile Thr Gly Ile Ser Val Asp Val His Gln Gln Ile
                325                 330                 335

Val Tyr Phe Ser Glu Gly Thr Leu Ile Trp Ala Lys Lys Ala Ala Asn
            340                 345                 350

Met Ser Asp Val Ser Asp Leu Arg Ile Phe Tyr Arg Gly Ser Gly Leu
        355                 360                 365

Ile Ser Ser Ile Ser Ile Asp Trp Leu Tyr Gln Arg Met Tyr Phe Ile
    370                 375                 380

Met Asp Glu Leu Val Cys Val Cys Asp Leu Glu Asn Cys Ser Asn Ile
385                 390                 395                 400

Glu Glu Ile Thr Pro Pro Ser Ile Ser Ala Pro Gln Lys Ile Val Ala
                405                 410                 415

Asp Ser Tyr Asn Gly Tyr Val Phe Tyr Leu Leu Arg Asp Gly Ile Tyr
            420                 425                 430

Arg Ala Asp Leu Pro Val Pro Ser Gly Arg Cys Ala Glu Ala Val Arg
        435                 440                 445

Ile Val Glu Ser Cys Thr Leu Lys Asp Phe Ala Ile Lys Pro Gln Ala
    450                 455                 460

Lys Arg Ile Ile Tyr Phe Asn Asp Thr Ala Gln Val Phe Met Ser Thr
465                 470                 475                 480

Phe Leu Asp Gly Ser Ala Ser His Leu Ile Leu Pro Arg Ile Pro Phe
                485                 490                 495

Ala Asp Val Lys Ser Phe Ala Cys Glu Asn Asn Asp Phe Leu Val Thr
            500                 505                 510

Asp Gly Lys Val Ile Phe Gln Gln Asp Ala Leu Ser Phe Asn Glu Phe
        515                 520                 525

Ile Val Gly Cys Asp Leu Ser His Ile Glu Glu Phe Gly Phe Gly Asn
    530                 535                 540

Leu Val Ile Phe Gly Ser Ser Ser Gln Leu His Pro Leu Pro Gly Arg
545                 550                 555                 560

Pro Gln Glu Leu Ser Val Leu Phe Gly Ser His Gln Ala Leu Val Gln
                565                 570                 575

Trp Lys Pro Pro Ala Leu Ala Ile Gly Ala Asn Val Ile Leu Ile Ser
            580                 585                 590

Asp Ile Ile Glu Leu Phe Glu Leu Gly Pro Ser Ala Trp Gln Asn Trp
        595                 600                 605

Thr Tyr Glu Val Lys Val Ser Thr Gln Asp Pro Pro Glu Val Thr His
```

-continued

```
    610                 615                 620

Ile Phe Leu Asn Ile Ser Gly Thr Met Leu Asn Val Pro Glu Leu Gln
625                 630                 635                 640

Ser Ala Met Lys Tyr Lys Val Ser Val Arg Ala Ser Ser Pro Lys Arg
                645                 650                 655

Pro Gly Pro Trp Ser Glu Pro Ser Val Gly Thr Thr Leu Val Pro Ala
            660                 665                 670

Ser Glu Pro Pro Phe Ile Met Ala Val Lys Glu Asp Gly Leu Trp Ser
        675                 680                 685

Lys Pro Leu Asn Ser Phe Gly Pro Gly Glu Phe Leu Ser Ser Asp Ile
    690                 695                 700

Gly Asn Val Ser Asp Met Asp Trp Tyr Asn Asn Ser Leu Tyr Tyr Ser
705                 710                 715                 720

Asp Thr Lys Gly Asp Val Phe Val Trp Leu Leu Asn Gly Thr Asp Ile
                725                 730                 735

Ser Glu Asn Tyr His Leu Pro Ser Ile Ala Gly Ala Gly Ala Leu Ala
            740                 745                 750

Phe Glu Trp Leu Gly His Phe Leu Tyr Trp Ala Gly Lys Thr Tyr Val
        755                 760                 765

Ile Gln Arg Gln Ser Val Leu Thr Gly His Thr Asp Ile Val Thr His
    770                 775                 780

Val Lys Leu Leu Val Asn Asp Met Val Val Asp Ser Val Gly Gly Tyr
785                 790                 795                 800

Leu Tyr Trp Thr Thr Leu Tyr Ser Val Glu Ser Thr Arg Leu Asn Gly
                805                 810                 815

Glu Ser Ser Leu Val Leu Gln Thr Gln Pro Trp Phe Ser Gly Lys Lys
            820                 825                 830

Val Ile Ala Leu Thr Leu Asp Leu Ser Asp Gly Leu Leu Tyr Trp Leu
        835                 840                 845

Val Gln Asp Ser Gln Cys Ile His Leu Tyr Thr Ala Val Leu Arg Gly
    850                 855                 860

Gln Ser Thr Gly Asp Thr Thr Ile Thr Glu Phe Ala Ala Trp Ser Thr
865                 870                 875                 880

Ser Glu Ile Ser Gln Asn Ala Leu Met Tyr Tyr Ser Gly Arg Leu Phe
                885                 890                 895

Trp Ile Asn Gly Phe Arg Ile Ile Thr Thr Gln Glu Ile Gly Gln Lys
            900                 905                 910

Thr Ser Val Ser Val Leu Glu Pro Ala Arg Phe Asn Gln Phe Thr Ile
        915                 920                 925

Ile Gln Thr Ser Leu Lys Pro Leu Pro Gly Asn Phe Ser Phe Thr Pro
    930                 935                 940

Lys Val Ile Pro Asp Ser Val Gln Glu Ser Ser Phe Arg Ile Glu Gly
945                 950                 955                 960

Asn Ala Ser Ser Phe Gln Ile Leu Trp Asn Gly Pro Pro Ala Val Asp
                965                 970                 975

Trp Gly Val Val Phe Tyr Ser Val Glu Phe Ser Ala His Ser Lys Phe
            980                 985                 990

Leu Ala Ser Glu Gln His Ser Leu  Pro Val Phe Thr Val  Glu Gly Leu
        995                 1000                1005

Glu Pro  Tyr Ala Leu Phe Asn  Leu Ser Val Thr Pro  Tyr Thr Tyr
    1010                1015                1020

Trp Gly  Lys Gly Pro Lys Thr  Ser Leu Ser Leu Arg  Ala Pro Glu
    1025                1030                1035
```

```
Thr Val  Pro Ser Ala Pro Glu  Asn Pro Arg Ile Phe  Ile Leu Pro
    1040                 1045                 1050

Ser Gly  Lys Cys Cys Asn Lys  Asn Glu Val Val Val  Glu Phe Arg
    1055                 1060                 1065

Trp Asn  Lys Pro Lys His Glu  Asn Gly Val Leu Thr  Lys Phe Glu
    1070                 1075                 1080

Ile Phe  Tyr Asn Ile Ser Asn  Gln Ser Ile Thr Asn  Lys Thr Cys
    1085                 1090                 1095

Glu Asp  Trp Ile Ala Val Asn  Val Thr Pro Ser Val  Met Ser Phe
    1100                 1105                 1110

Gln Leu  Glu Gly Met Ser Pro  Arg Cys Phe Ile Ala  Phe Gln Val
    1115                 1120                 1125

Arg Ala  Phe Thr Ser Lys Gly  Pro Gly Pro Tyr Ala  Asp Val Val
    1130                 1135                 1140

Lys Ser  Thr Thr Ser Glu Ile  Asn Pro Phe Pro His  Leu Ile Thr
    1145                 1150                 1155

Leu Leu  Gly Asn Lys Ile Val  Phe Leu Asp Met Asp  Gln Asn Gln
    1160                 1165                 1170

Val Val  Trp Thr Phe Ser Ala  Glu Arg Val Ile Ser  Ala Val Cys
    1175                 1180                 1185

Tyr Thr  Ala Asp Asn Glu Met  Gly Tyr Tyr Ala Glu  Gly Asp Ser
    1190                 1195                 1200

Leu Phe  Leu Leu His Leu His  Asn Arg Ser Ser Ser  Glu Leu Phe
    1205                 1210                 1215

Gln Asp  Ser Leu Val Phe Asp  Ile Thr Val Ile Thr  Ile Asp Trp
    1220                 1225                 1230

Ile Ser  Arg His Leu Tyr Phe  Ala Leu Lys Glu Ser  Gln Asn Gly
    1235                 1240                 1245

Met Gln  Val Phe Asp Val Asp  Leu Glu His Lys Val  Lys Tyr Pro
    1250                 1255                 1260

Arg Glu  Val Lys Ile His Asn  Arg Asn Ser Thr Ile  Ile Ser Phe
    1265                 1270                 1275

Ser Val  Tyr Pro Leu Leu Ser  Arg Leu Tyr Trp Thr  Glu Val Ser
    1280                 1285                 1290

Asn Phe  Gly Tyr Gln Met Phe  Tyr Tyr Ser Ile Ile  Ser His Thr
    1295                 1300                 1305

Leu His  Arg Ile Leu Gln Pro  Thr Ala Thr Asn Gln  Gln Asn Lys
    1310                 1315                 1320

Arg Asn  Gln Cys Ser Cys Asn  Val Thr Glu Phe Glu  Leu Ser Gly
    1325                 1330                 1335

Ala Met  Ala Ile Asp Thr Ser  Asn Leu Glu Lys Pro  Leu Ile Tyr
    1340                 1345                 1350

Phe Ala  Lys Ala Gln Glu Ile  Trp Ala Met Asp Leu  Glu Gly Cys
    1355                 1360                 1365

Gln Cys  Trp Arg Val Ile Thr  Val Pro Ala Met Leu  Ala Gly Lys
    1370                 1375                 1380

Thr Leu  Val Ser Leu Thr Val  Asp Gly Asp Leu Ile  Tyr Trp Ile
    1385                 1390                 1395

Ile Thr  Ala Lys Asp Ser Thr  Gln Ile Tyr Gln Ala  Lys Lys Gly
    1400                 1405                 1410

Asn Gly  Ala Ile Val Ser Gln  Val Lys Ala Leu Arg  Ser Arg His
    1415                 1420                 1425
```

```
Ile Leu  Ala Tyr Ser Ser Val  Met Gln Pro Phe Pro  Asp Lys Ala
    1430                 1435                 1440

Phe Leu  Ser Leu Ala Ser Asp  Thr Val Glu Pro Thr  Ile Leu Asn
    1445                 1450                 1455

Ala Thr  Asn Thr Ser Leu Thr  Ile Arg Leu Pro Leu  Ala Lys Thr
    1460                 1465                 1470

Asn Leu  Thr Trp Tyr Gly Ile  Thr Ser Pro Thr Pro  Thr Tyr Leu
    1475                 1480                 1485

Val Tyr  Tyr Ala Glu Val Asn  Asp Arg Lys Asn Ser  Ser Asp Leu
    1490                 1495                 1500

Lys Tyr  Arg Ile Leu Glu Phe  Gln Asp Ser Ile Ala  Leu Ile Glu
    1505                 1510                 1515

Asp Leu  Gln Pro Phe Ser Thr  Tyr Met Ile Gln Ile  Ala Val Lys
    1520                 1525                 1530

Asn Tyr  Tyr Ser Asp Pro Leu  Glu His Leu Pro Pro  Gly Lys Glu
    1535                 1540                 1545

Ile Trp  Gly Lys Thr Lys Asn  Gly Val Pro Glu Ala  Val Gln Leu
    1550                 1555                 1560

Ile Asn  Thr Thr Val Arg Ser  Asp Thr Ser Leu Ile  Ile Ser Trp
    1565                 1570                 1575

Arg Glu  Ser His Lys Pro Asn  Gly Pro Lys Glu Ser  Val Arg Tyr
    1580                 1585                 1590

Gln Leu  Ala Ile Ser His Leu  Ala Leu Ile Pro Glu  Thr Pro Leu
    1595                 1600                 1605

Arg Gln  Ser Glu Phe Pro Asn  Gly Arg Leu Thr Leu  Leu Val Thr
    1610                 1615                 1620

Arg Leu  Ser Gly Gly Asn Ile  Tyr Val Leu Lys Val  Leu Ala Cys
    1625                 1630                 1635

His Ser  Glu Glu Met Trp Cys  Thr Glu Ser His Pro  Val Thr Val
    1640                 1645                 1650

Glu Met  Phe Asn Thr Pro Glu  Lys Pro Tyr Ser Leu  Val Pro Glu
    1655                 1660                 1665

Asn Thr  Ser Leu Gln Phe Asn  Trp Lys Ala Pro Leu  Asn Val Asn
    1670                 1675                 1680

Leu Ile  Arg Phe Trp Val Glu  Leu Gln Lys Trp Lys  Tyr Asn Glu
    1685                 1690                 1695

Phe Tyr  His Val Lys Thr Ser  Cys Ser Gln Gly Pro  Ala Tyr Val
    1700                 1705                 1710

Cys Asn  Ile Thr Asn Leu Gln  Pro Tyr Thr Ser Tyr  Asn Val Arg
    1715                 1720                 1725

Val Val  Val Val Tyr Lys Thr  Gly Glu Asn Ser Thr  Ser Leu Pro
    1730                 1735                 1740

Glu Ser  Phe Lys Thr Lys Ala  Gly Val Pro Asn Lys  Pro Gly Ile
    1745                 1750                 1755

Pro Lys  Leu Leu Glu Gly Ser  Lys Asn Ser Ile Gln  Trp Glu Lys
    1760                 1765                 1770

Ala Glu  Asp Asn Gly Cys Arg  Ile Thr Tyr Tyr Ile  Leu Glu Ile
    1775                 1780                 1785

Arg Lys  Ser Thr Ser Asn Asn  Leu Gln Asn Gln Asn  Leu Arg Trp
    1790                 1795                 1800

Lys Met  Thr Phe Asn Gly Ser  Cys Ser Ser Val Cys  Thr Trp Lys
    1805                 1810                 1815

Ser Lys  Asn Leu Lys Gly Ile  Phe Gln Phe Arg Val  Val Ala Ala
```

```
    1820                1825                1830

Asn Asn  Leu Gly Phe Gly Glu  Tyr Ser Gly Ile Ser  Glu Asn Ile
    1835                1840                1845

Ile Leu  Val Gly Asp Asp Phe  Trp Ile Pro Glu Thr  Ser Phe Ile
    1850                1855                1860

Leu Thr  Ile Ile Val Gly Ile  Phe Leu Val Val Thr  Ile Pro Leu
    1865                1870                1875

Thr Phe  Val Trp His Arg Arg  Leu Lys Asn Gln Lys  Ser Ala Lys
    1880                1885                1890

Glu Gly  Val Thr Val Leu Ile  Asn Glu Asp Lys Glu  Leu Ala Glu
    1895                1900                1905

Leu Arg  Gly Leu Ala Ala Gly  Val Gly Leu Ala Asn  Ala Cys Tyr
    1910                1915                1920

Ala Ile  His Thr Leu Pro Thr  Gln Glu Glu Ile Glu  Asn Leu Pro
    1925                1930                1935

Ala Phe  Pro Arg Glu Lys Leu  Thr Leu Arg Leu Leu  Leu Gly Ser
    1940                1945                1950

Gly Ala  Phe Gly Glu Val Tyr  Glu Gly Thr Ala Val  Asp Ile Leu
    1955                1960                1965

Gly Val  Gly Ser Gly Glu Ile  Lys Val Ala Val Lys  Thr Leu Lys
    1970                1975                1980

Lys Gly  Ser Thr Asp Gln Glu  Lys Ile Glu Phe Leu  Lys Glu Ala
    1985                1990                1995

His Leu  Met Ser Lys Phe Asn  His Pro Asn Ile Leu  Lys Gln Leu
    2000                2005                2010

Gly Val  Cys Leu Leu Asn Glu  Pro Gln Tyr Ile Ile  Leu Glu Leu
    2015                2020                2025

Met Glu  Gly Gly Asp Leu Leu  Thr Tyr Leu Arg Lys  Ala Arg Met
    2030                2035                2040

Ala Thr  Phe Tyr Gly Pro Leu  Leu Thr Leu Val Asp  Leu Val Asp
    2045                2050                2055

Leu Cys  Val Asp Ile Ser Lys  Gly Cys Val Tyr Leu  Glu Arg Met
    2060                2065                2070

His Phe  Ile His Arg Asp Leu  Ala Ala Arg Asn Cys  Leu Val Ser
    2075                2080                2085

Val Lys  Asp Tyr Thr Ser Pro  Arg Ile Val Lys Ile  Gly Asp Phe
    2090                2095                2100

Gly Leu  Ala Arg Asp Ile Tyr  Lys Asn Asp Tyr Tyr  Arg Lys Arg
    2105                2110                2115

Gly Glu  Gly Leu Leu Pro Val  Arg Trp Met Ala Pro  Glu Ser Leu
    2120                2125                2130

Met Asp  Gly Ile Phe Thr Thr  Gln Ser Asp Val Trp  Ser Phe Gly
    2135                2140                2145

Ile Leu  Ile Trp Glu Ile Leu  Thr Leu Gly His Gln  Pro Tyr Pro
    2150                2155                2160

Ala His  Ser Asn Leu Asp Val  Leu Asn Tyr Val Gln  Thr Gly Gly
    2165                2170                2175

Arg Leu  Glu Pro Pro Arg Asn  Cys Pro Asp Asp Leu  Trp Asn Leu
    2180                2185                2190

Met Thr  Gln Cys Trp Ala Gln  Glu Pro Asp Gln Arg  Pro Thr Phe
    2195                2200                2205

His Arg  Ile Gln Asn Gln Leu  Gln Leu Phe Arg Asn  Phe Phe Leu
    2210                2215                2220
```

```
Asn Ser  Ile Tyr Gln Cys Arg  Asp Glu Ala Asn Asn  Ser Gly Val
    2225                 2230                 2235

Ile Asn  Glu Ser Phe Glu Gly  Glu Asp Gly Asp Val  Ile Cys Leu
    2240                 2245                 2250

Asn Ser  Asp Asp Ile Met Pro  Val Val Leu Met Glu  Thr Lys Asn
    2255                 2260                 2265

Arg Glu  Gly Leu Asn Tyr Met  Val Leu Ala Thr Glu  Cys Gly Gln
    2270                 2275                 2280

Gly Glu  Glu Lys Ser Glu Gly  Pro Leu Gly Ser Gln  Glu Ser Glu
    2285                 2290                 2295

Ser Cys  Gly Leu Arg Lys Glu  Glu Lys Glu Pro His  Ala Asp Lys
    2300                 2305                 2310

Asp Phe  Cys Gln Glu Lys Gln  Val Ala Tyr Cys Pro  Ser Gly Lys
    2315                 2320                 2325

Pro Glu  Gly Leu Asn Tyr Ala  Cys Leu Thr His Ser  Gly Tyr Gly
    2330                 2335                 2340

Asp Gly  Ser Asp
    2345
```

<210> SEQ ID NO 6
<211> LENGTH: 7368
<212> TYPE: DNA
<213> ORGANISM: Homo sapiens

<400> SEQUENCE: 6

```
caagctttca agcattcaaa ggtctaaatg aaaaaggcta agtattattt caaaaggcaa     60

gtatatccta atatagcaaa acaaacaaag caaaatccat cagctactcc tccaattgaa    120

gtgatgaagc ccaaataatt catatagcaa aatggagaaa attagaccgg ccatctaaaa    180

atctgccatt ggtgaagtga tgaagaacat ttactgtctt attccgaagc ttgtcaattt    240

tgcaactctt ggctgcctat ggatttctgt ggtgcagtgt acagttttaa atagctgcct    300

aaagtcgtgt gtaactaatc tgggccagca gcttgacctt ggcacaccac ataatctgag    360

tgaaccgtgt atccaaggat gtcacttttg gaactctgta gatcagaaaa actgtgcttt    420

aaagtgtcgg gagtcgtgtg aggttggctg tagcagcgcg gaaggtgcat atgaagagga    480

agtactggaa aatgcagacc taccaactgc tccctttgct tcttccattg gaagccacaa    540

tatgacatta cgatggaaat ctgcaaactt ctctggagta aaatacatca ttcagtggaa    600

atatgcacaa cttctgggaa gctggactta tactaagact gtgtccagac cgtcctatgt    660

ggtcaagccc ctgcacccct tcactgagta cattttccga gtggtttgga tcttcacagc    720

gcagctgcag ctctactccc ctccaagtcc cagttacagg actcatcctc atggagttcc    780

tgaaactgca cctttgatta ggaatattga gagctcaagt cccgacactg tggaagtcag    840

ctgggatcca cctcaattcc caggtggacc tattttgggt tataacttaa ggctgatcag    900

caaaaatcaa aaattagatg cagggacaca gagaaccagt ttccagtttt actccacttt    960

accaaatact atctacaggt tttctattgc agcagtaaat gaagttggtg agggtccaga   1020

agcagaatct agtattacca cttcatcttc agcagttcaa caagaggaac agtggctctt   1080

tttatccaga aaaacttctc taagaaagag atctttaaaa catttagtag atgaagcaca   1140

ttgccttcgg ttggatgcta tataccataa tattacagga atatctgttg atgtccacca   1200

gcaaattgtt tatttctctg aaggaactct catatgggcg aagaaggctg ccaacatgtc   1260

tgatgtatct gacctgagaa ttttttacag aggttcagga ttaatttctt ctatctccat   1320
```

```
agattggctt tatcaaagaa tgtatttcat catggatgaa ctggtatgtg tctgtgattt   1380
agagaactgc tcaaacatcg aggaaattac tccaccctct attagtgcac ctcaaaaaat   1440
tgtggctgat tcatacaatg ggtatgtctt ttacctcctg agagatggca tttatagagc   1500
agaccttcct gtaccatctg gccggtgtgc agaagctgtg cgtattgtgg agagttgcac   1560
gttaaaggac tttgcaatca agccacaagc caagcgaatc atttacttca atgacactgc   1620
ccaagtcttc atgtcaacat ttctggatgg ctctgcttcc catctcatcc tacctcgcat   1680
ccccctttgct gatgtgaaaa gttttgcttg tgaaaacaat gactttcttg tcacagatgg   1740
caaggtcatt ttccaacagg atgctttgtc ttttaatgaa ttcatcgtgg gatgtgacct   1800
gagtcacata gaagaatttg ggtttggtaa cttggtcatc tttggctcat cctcccagct   1860
gcaccctctg ccaggccgcc cgcaggagct ttcggtgctg tttggctctc accaggctct   1920
tgttcaatgg aagcctcctg cccttgccat aggagccaat gtcatcctga tcagtgatat   1980
tattgaactc tttgaattag gcccttctgc ctggcagaac tggacctatg aggtgaaagt   2040
atccacccaa gaccctcctg aagtcactca tattttcttg aacataagtg gaaccatgct   2100
gaatgtacct gagctgcaga gtgctatgaa atacaaggtt tctgtgagag caagttctcc   2160
aaagaggcca ggcccctggt cagagccctc agtgggtact accctggtgc cagctagtga   2220
accaccattt atcatggctg tgaaagaaga tgggctttgg agtaaaccat taaatagctt   2280
tggcccagga gagttcttat cctctgatat aggaaatgtg tcagacatgg attggtataa   2340
caacagcctc tactacagtg acacgaaagg cgacgttttt gtgtggctgc tgaatgggac   2400
ggatatctca gagaattatc acctacccag cattgcagga gcaggggctt tagcttttga   2460
gtggctgggt cactttctct actgggctgg aaagacatat gtgatacaaa ggcagtctgt   2520
gttgacggga cacacagaca ttgttaccca cgtgaagcta ttggtgaatg acatggtggt   2580
ggattcagtt ggtggatatc tctactggac cacactctat tcagtggaaa gcaccagact   2640
aaatggggaa agttcccttg tactacagac acagccttgg ttttctggga aaaaggtaat   2700
tgctctaact ttagacctca gtgatgggct cctgtattgg ttggttcaag acagtcaatg   2760
tattcacctg tacacagctg ttcttcgggg acagagcact ggggatacca ccatcacaga   2820
atttgcagcc tggagtactt ctgaaatttc ccagaatgca ctgatgtact atagtggtcg   2880
gctgttctgg atcaatggct ttaggattat cacaactcaa gaaataggtc agaaaaccag   2940
tgtctctgtt ttggaaccag ccagatttaa tcagttcaca attattcaga catcccttaa   3000
gcccctgcca gggaactttt cctttacccc taaggttatt ccagattctg ttcaagagtc   3060
ttcatttagg attgaaggaa atgcttcaag ttttcaaatc ctgtggaatg gtccccctgc   3120
ggtagactgg ggtgtagttt tctacagtgt agaatttagt gctcattcta agttcttggc   3180
tagtgaacaa cactctttac ctgtatttac tgtggaagga ctggaacctt atgccttatt   3240
taatctttct gtcactcctt atacctactg ggaaagggc cccaaaacat ctctgtcact   3300
tcgagcacct gaaacagttc catcagcacc agagaacccc agaatattta tattaccaag   3360
tggaaaatgc tgcaacaaga atgaagttgt ggtggaattt aggtggaaca aacctaagca   3420
tgaaaatggg gtgttaacaa aatttgaaat tttctacaat atatccaatc aaagtattac   3480
aaacaaaaca tgtgaagact ggattgctgt caatgtcact ccctcagtga tgtcttttca   3540
acttgaaggc atgagtccca gatgctttat tgccttccag gttagggcct ttacatctaa   3600
ggggccagga ccatatgctg acgttgtaaa gtctacaaca tcagaaatca acccatttcc   3660
```

```
tcacctcata actcttcttg gtaacaagat agttttttta gatatggatc aaaatcaagt   3720
tgtgtggacg ttttcagcag aaagagttat cagtgccgtt tgctacacag ctgataatga   3780
gatgggatat tatgctgaag ggactcact ctttcttctg cacttgcaca atcgctctag    3840
ctctgagctt ttccaagatt cactggtttt tgatatcaca gttattacaa ttgactggat   3900
ttcaaggcac ctctactttg cactgaaaga atcacaaaat ggaatgcaag tatttgatgt   3960
tgatcttgaa cacaaggtga aatatcccag agaggtgaag attcacaata ggaattcaac   4020
aataatttct ttttctgtat atcctctttt aagtcgcttg tattggacag aagtttccaa   4080
ttttggctac cagatgttct actacagtat tatcagtcac accttgcacc gaattctgca   4140
acccacagct acaaaccaac aaaacaaaag gaatcaatgt tcttgtaatg tgactgaatt   4200
tgagttaagt ggagcaatgg ctattgatac ctctaaccta gagaaaccat tgatatactt   4260
tgccaaagca caagagatct gggcaatgga tctggaaggc tgtcagtgtt ggagagttat   4320
cacagtacct gctatgctcg caggaaaaac ccttgttagc ttaactgtgg atggagatct   4380
tatatactgg atcatcacag caaaggacag cacacagatt tatcaggcaa agaaaggaaa   4440
tggggccatc gtttcccagg tgaaggccct aaggagtagg catatcttgg cttacagttc   4500
agttatgcag ccttttccag ataaagcgtt tctgtctcta gcttcagaca ctgtggaacc   4560
aactatactt aatgccacta acactagcct cacaatcaga ttacctctgg ccaagacaaa   4620
cctcacatgg tatggcatca ccagccctac tccaacatac ctggtttatt atgcagaagt   4680
taatgacagg aaaaacagct ctgacttgaa atatagaatt ctggaatttc aggacagtat   4740
agctcttatt gaagatttac aaccattttc aacatacatg atacagatag ctgtaaaaaa   4800
ttattattca gatcctttgg aacatttacc accaggaaaa gagatttggg gaaaaactaa   4860
aaatggagta ccagaggcag tgcagctcat taatacaact gtgcggtcag acaccagcct   4920
cattatatct tggagagaat ctcacaagcc aaatggacct aaagaatcag tccgttatca   4980
gttggcaatc tcacacctgg ccctaattcc tgaaactcct ctaagacaaa gtgaatttcc   5040
aaatggaagg ctcactctcc ttgttactag actgtctggt ggaaatattt atgtgttaaa   5100
ggttcttgcc tgccactctg aggaaatgtg gtgtacagag agtcatcctg tcactgtgga   5160
aatgtttaac acaccagaga aaccttattc cttggttcca gagaacacta gtttgcaatt   5220
taattggaag gctccattga atgttaacct catcagattt tgggttgagc tacagaagtg   5280
gaaatacaat gagttttacc atgttaaaac ttcatgcagc caaggtcctg cttatgtctg   5340
taatatcaca aatctacaac cttatacttc atataatgtc agagtagtgg tggtttataa   5400
gacgggagaa aatagcacct cacttccaga aagctttaag acaaaagctg gagtcccaaa   5460
taaaccaggc attcccaaat tactagaagg gagtaaaaat tcaatacagt gggagaaagc   5520
tgaagataat ggatgtagaa ttacatacta tatccttgag ataagaaaga gcacttcaaa   5580
taatttacag aaccagaatt taaggtggaa gatgacattt aatggatcct gcagtagtgt   5640
ttgcacatgg aagtccaaaa acctgaaagg aatatttcag ttcagagtag tagctgcaaa   5700
taatctaggg tttggtgaat atagtggaat cagtgagaat attatattag ttggagatga   5760
tttttggata ccagaaacaa gtttcatact tactattata gttggaatat ttctggttgt   5820
tacaatccca ctgacctttg tctggcatag aagattaaag aatcaaaaaa gtgccaagga   5880
aggggtgaca gtgcttataa acgaagacaa agagttggct gagctgcgag gtctggcagc   5940
cggagtaggc ctggctaatg cctgctatgc aatacatact cttccaaccc aagaggagat   6000
tgaaaatctt cctgccttcc ctcgggaaaa actgactctg cgtctcttgc tgggaagtgg   6060
```

agcctttgga gaagtgtatg aaggaacagc agtggacatc ttaggagttg gaagtggaga 6120
aatcaaagta gcagtgaaga ctttgaagaa gggttccaca gaccaggaga agattgaatt 6180
cctgaaggag gcacatctga tgagcaaatt taatcatccc aacattctga agcagcttgg 6240
agtttgtctg ctgaatgaac cccaatacat tatcctggaa ctgatggagg gaggagacct 6300
tcttacttat ttgcgtaaag cccggatggc aacgttttat ggtcctttac tcaccttggt 6360
tgaccttgta gacctgtgtg tagatatttc aaaaggctgt gtctacttgg aacggatgca 6420
tttcattcac agggatctgg cagctagaaa ttgccttgtt tccgtgaaag actataccag 6480
tccacggata gtgaagattg gagactttgg actcgccaga gacatctata aaaatgatta 6540
ctatagaaag agaggggaag gcctgctccc agttcggtgg atggctccag aaagtttgat 6600
ggatggaatc ttcactactc aatctgatgt atggtctttt ggaattctga tttgggagat 6660
tttaactctt ggtcatcagc cttatccagc tcattccaac cttgatgtgt taaactatgt 6720
gcaaacagga gggagactgg agccaccaag aaattgtcct gatgatctgt ggaatttaat 6780
gacccagtgc tgggctcaag aacccgacca aagacctact tttcatagaa ttcaggacca 6840
acttcagtta ttcagaaatt ttttcttaaa tagcatttat aagtccagag atgaagcaaa 6900
caacagtgga gtcataaatg aaagctttga aggtgaagat ggcgatgtga tttgtttgaa 6960
ttcagatgac attatgccag ttgctttaat ggaaacgaag aaccgagaag ggttaaacta 7020
tatggtactt gctacagaat gtggccaagg tgaagaaaag tctgagggtc ctctaggctc 7080
ccaggaatct gaatcttgtg gtctgaggaa agaagagaag gaaccacatg cagacaaaga 7140
tttctgccaa gaaaaacaag tggcttactg cccttctggc aagcctgaag gcctgaacta 7200
tgcctgtctc actcacagtg gatatggaga tgggtctgat taatagcgtt gtttgggaaa 7260
tagagagttg agataaacac tctcattcag tagttactga aagaaaactc tgctagaatg 7320
ataaatgtca tggtggtcta taactccaaa taaacaatgc aacgttcc 7368

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
acccttctcg gttcttcgtt tcca 24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
gcagctcagc caactctttg tctt 24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic primer

```
<400> SEQUENCE: 9

tgccagacaa aggtcagtgg gatt                                            24


<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

gcagaatgcc accaagtatg gcaa                                            24


<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Arg Leu Ile Glu Asp Ala Glu Tyr Ala Ala Arg Gly
1               5                   10


<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Val Gly Asp Asp Phe
1               5


<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13

tttttttttt tttttttttt                                                 20
```